US012629506B2

(12) United States Patent
Fedor et al.

(10) Patent No.: US 12,629,506 B2
(45) Date of Patent: *May 19, 2026

(54) LOW-PROFILE SINGLE AND DUAL VASCULAR ACCESS DEVICE

(71) Applicant: C. R. Bard, Inc., Franklin Lakes, NJ (US)

(72) Inventors: Brenda L. F. Fedor, Holladay, UT (US); Jason R. Stats, Layton, UT (US); Ian N. Thomas, West Bountiful, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 828 days.

This patent is subject to a terminal disclaimer.

(21) Appl. No.: 17/890,184

(22) Filed: Aug. 17, 2022

(65) Prior Publication Data

US 2022/0395678 A1 Dec. 15, 2022

Related U.S. Application Data

(63) Continuation of application No. 15/809,879, filed on Nov. 10, 2017, now Pat. No. 11,420,033, which is a
(Continued)

(51) Int. Cl.
| | |
|---|---|
| *A61M 39/02* | (2006.01) |
| *A61B 17/34* | (2006.01) |
| *A61M 1/36* | (2006.01) |

(52) U.S. Cl.
CPC ..... *A61M 39/0208* (2013.01); *A61B 17/3423* (2013.01); *A61M 1/3659* (2014.02);
(Continued)

(58) Field of Classification Search
CPC ............ A61M 39/0208; A61M 1/3659; A61M 2039/0211; A61M 2039/0232;
(Continued)

(56) References Cited

U.S. PATENT DOCUMENTS

| | | | |
|---|---|---|---|
| 3,951,147 | A | 4/1976 | Tucker et al. |
| 4,184,489 | A | 1/1980 | Burd |
| | | (Continued) | |

FOREIGN PATENT DOCUMENTS

| | | |
|---|---|---|
| CA | 1261698 A | 9/1989 |
| CA | 2318089 A1 | 7/1999 |
| | (Continued) | |

OTHER PUBLICATIONS

"Merge". Merriam-Webster Dictionary. https://www.merriam-webster.com/dictionary/merge. Access May 13, 2021. (Year: 2021).
(Continued)

*Primary Examiner* — Theodore J Stigell
(74) *Attorney, Agent, or Firm* — Rutan & Tucker LLP

(57) ABSTRACT

A low-profile access port for subcutaneous implantation within a patient is disclosed. The access port includes a receiving cup that provides a relatively large subcutaneous target to enable catheter-bearing needle access to the port without difficulty. In one embodiment, a low-profile access port comprises a body including a conduit with an inlet port at a proximal end, and a receiving cup. The receiving cup is funnel shaped to direct a catheter-bearing needle into the conduit via the inlet port. The conduit is defined by the body and extends from the inlet port to an outlet defined by a stem. A bend in the conduit enables catheter advancement past the bend while preventing needle advancement. A valve/seal assembly is also disposed in the conduit and enables passage of the catheter therethrough while preventing fluid backflow. The body includes radiopaque indicia configured to enable identification of the access port via x-ray imaging.

13 Claims, 37 Drawing Sheets

Related U.S. Application Data continuation-in-part of application No. 14/162,113, filed on Jan. 23, 2014, now Pat. No. 10,463,845.

(60) Provisional application No. 62/552,681, filed on Aug. 31, 2017, provisional application No. 62/421,131, filed on Nov. 11, 2016, provisional application No. 61/755,913, filed on Jan. 23, 2013.

(52) U.S. Cl.
CPC ................ *A61M 2039/0211* (2013.01); *A61M 2039/0232* (2013.01); *A61M 2039/0235* (2013.01); *A61M 2039/0238* (2013.01); *Y10T 29/49826* (2015.01)

(58) Field of Classification Search
CPC .. A61M 2039/0235; A61M 2039/0238; A61B 17/3423; Y10T 29/49826
See application file for complete search history.

(56) References Cited

U.S. PATENT DOCUMENTS

| | | | |
|---|---|---|---|
| 4,222,374 A | 9/1980 | Sampson et al. | |
| 4,400,169 A | 8/1983 | Stephen | |
| 4,447,237 A | 5/1984 | Frisch et al. | |
| 4,496,349 A | 1/1985 | Cosentino | |
| 4,543,088 A | 9/1985 | Bootman et al. | |
| 4,559,039 A | 12/1985 | Ash et al. | |
| 4,569,675 A | 2/1986 | Prosl et al. | |
| 4,673,394 A | 6/1987 | Fenton, Jr. et al. | |
| 4,675,004 A | 6/1987 | Hadford et al. | |
| 4,692,146 A | 9/1987 | Hilger | |
| 4,695,273 A | 9/1987 | Brown | |
| 4,704,103 A | 11/1987 | Stober et al. | |
| 4,710,174 A | 12/1987 | Moden et al. | |
| 4,751,926 A | 6/1988 | Sasaki | |
| 4,762,517 A | 8/1988 | McIntyre et al. | |
| 4,767,410 A | 8/1988 | Moden et al. | |
| 4,772,270 A | 9/1988 | Wiita et al. | |
| 4,772,276 A | 9/1988 | Wiita et al. | |
| 4,778,452 A | 10/1988 | Moden et al. | |
| 4,790,826 A | 12/1988 | Elftman | |
| 4,802,885 A | 2/1989 | Weeks et al. | |
| 4,804,054 A | 2/1989 | Howson et al. | |
| 4,820,273 A | 4/1989 | Reinicke | |
| 4,861,341 A | 8/1989 | Woodburn | |
| 4,886,501 A | 12/1989 | Johnston et al. | |
| 4,892,518 A | 1/1990 | Cupp et al. | |
| 4,897,081 A | 1/1990 | Poirier et al. | |
| 4,904,241 A | 2/1990 | Bark | |
| 4,915,690 A | 4/1990 | Cone et al. | |
| 4,929,236 A | 5/1990 | Sampson | |
| 4,963,133 A | 10/1990 | Whipple | |
| 4,978,338 A | 12/1990 | Melsky et al. | |
| 4,997,424 A | 3/1991 | Little | |
| 5,013,298 A | 5/1991 | Moden et al. | |
| 5,041,098 A | 8/1991 | Loiterman et al. | |
| 5,045,060 A | 9/1991 | Melsky et al. | |
| 5,045,064 A | 9/1991 | Idriss | |
| 5,053,013 A | 10/1991 | Ensminger et al. | |
| 5,057,084 A * | 10/1991 | Ensminger ........ | A61M 39/0208 604/167.04 |
| 5,084,015 A | 1/1992 | Moriuchi | |
| 5,090,954 A | 2/1992 | Geary | |
| 5,108,377 A | 4/1992 | Cone et al. | |
| 5,137,529 A | 8/1992 | Watson et al. | |
| 5,147,321 A | 9/1992 | Slonina et al. | |
| 5,147,483 A | 9/1992 | Melsky et al. | |
| 5,158,547 A | 10/1992 | Doan et al. | |
| 5,167,633 A | 12/1992 | Mann et al. | |
| 5,167,638 A | 12/1992 | Felix et al. | |
| 5,171,228 A | 12/1992 | McDonald | |
| 5,178,612 A | 1/1993 | Fenton, Jr. | |
| 5,180,365 A | 1/1993 | Ensminger et al. | |
| 5,185,003 A | 2/1993 | Brethauer | |
| 5,201,715 A | 4/1993 | Masters | |
| 5,203,771 A | 4/1993 | Melker et al. | |
| 5,213,574 A | 5/1993 | Tucker | |
| D337,637 S | 7/1993 | Tucker | |
| 5,226,879 A | 7/1993 | Ensminger et al. | |
| 5,263,930 A | 11/1993 | Ensminger | |
| 5,266,071 A | 11/1993 | Elftman | |
| 5,281,199 A | 1/1994 | Ensminger et al. | |
| 5,281,205 A | 1/1994 | McPherson | |
| 5,312,355 A | 5/1994 | Lee | |
| 5,318,545 A | 6/1994 | Tucker | |
| 5,336,194 A | 8/1994 | Polaschegg et al. | |
| 5,350,360 A * | 9/1994 | Ensminger ........ | A61M 39/0208 604/288.03 |
| 5,360,407 A | 11/1994 | Leonard et al. | |
| 5,387,192 A | 2/1995 | Glantz et al. | |
| 5,395,324 A | 3/1995 | Hinrichs et al. | |
| 5,399,168 A | 3/1995 | Wadsworth, Jr. et al. | |
| 5,405,325 A | 4/1995 | Labs | |
| 5,409,463 A | 4/1995 | Thomas et al. | |
| 5,417,656 A | 5/1995 | Ensminger et al. | |
| 5,421,814 A | 6/1995 | Geary | |
| 5,423,334 A | 6/1995 | Jordan | |
| 5,441,504 A | 8/1995 | Pohndorf et al. | |
| 5,476,451 A | 12/1995 | Ensminger et al. | |
| 5,503,630 A | 4/1996 | Ensminger et al. | |
| 5,514,103 A | 5/1996 | Srisathapat et al. | |
| 5,520,643 A * | 5/1996 | Ensminger ........ | A61M 39/0208 604/245 |
| 5,527,277 A | 6/1996 | Ensminger et al. | |
| 5,527,278 A | 6/1996 | Ensminger et al. | |
| 5,531,684 A | 7/1996 | Ensminger et al. | |
| 5,542,923 A | 8/1996 | Ensminger et al. | |
| 5,554,117 A | 9/1996 | Ensminger et al. | |
| 5,556,381 A | 9/1996 | Ensminger et al. | |
| 5,558,641 A | 9/1996 | Glantz et al. | |
| 5,562,617 A | 10/1996 | Finch, Jr. et al. | |
| 5,562,618 A | 10/1996 | Cai et al. | |
| 5,575,770 A | 11/1996 | Melsky et al. | |
| 5,578,070 A | 11/1996 | Utterberg | |
| 5,607,393 A | 3/1997 | Ensminger et al. | |
| 5,613,945 A | 3/1997 | Cai et al. | |
| 5,620,419 A | 4/1997 | Lui et al. | |
| 5,632,729 A | 5/1997 | Cai et al. | |
| 5,647,855 A | 7/1997 | Trooskin | |
| 5,695,490 A | 12/1997 | Flaherty et al. | |
| 5,702,363 A | 12/1997 | Flaherty | |
| 5,704,915 A | 1/1998 | Melsky et al. | |
| 5,713,858 A | 2/1998 | Heruth et al. | |
| 5,718,682 A | 2/1998 | Tucker | |
| 5,725,507 A | 3/1998 | Petrick | |
| 5,741,228 A | 4/1998 | Lambrecht et al. | |
| 5,743,873 A | 4/1998 | Cai et al. | |
| 5,758,667 A | 6/1998 | Slettenmark | |
| 5,769,823 A | 6/1998 | Otto | |
| 5,792,104 A | 8/1998 | Speckman et al. | |
| 5,810,789 A | 9/1998 | Powers et al. | |
| 5,833,654 A | 11/1998 | Powers et al. | |
| 5,848,989 A | 12/1998 | Villani | |
| 5,906,596 A | 5/1999 | Tallarida | |
| 5,908,414 A | 6/1999 | Otto et al. | |
| 5,913,998 A | 6/1999 | Butler et al. | |
| 5,925,017 A | 7/1999 | Kriesel et al. | |
| 5,931,829 A | 8/1999 | Burbank et al. | |
| 5,944,688 A | 8/1999 | Lois | |
| 5,947,953 A | 9/1999 | Ash et al. | |
| 5,951,512 A | 9/1999 | Dalton | |
| 5,954,687 A | 9/1999 | Baudino | |
| 5,954,691 A | 9/1999 | Prosl | |
| 5,968,011 A | 10/1999 | Larsen et al. | |
| 5,989,206 A | 11/1999 | Prosl et al. | |
| 5,989,216 A | 11/1999 | Johnson et al. | |
| 5,989,239 A | 11/1999 | Finch et al. | |
| 6,007,516 A | 12/1999 | Burbank et al. | |
| 6,013,051 A | 1/2000 | Nelson | |
| 6,013,058 A | 1/2000 | Prosl et al. | |
| 6,022,335 A | 2/2000 | Ramadan | |
| 6,039,712 A | 3/2000 | Fogarty et al. | |

(56) References Cited

U.S. PATENT DOCUMENTS

| | | | |
|---|---|---|---|
| 6,042,569 A | 3/2000 | Finch, Jr. et al. |
| 6,053,901 A | 4/2000 | Finch, Jr. et al. |
| 6,056,717 A | 5/2000 | Finch et al. |
| 6,086,555 A | 7/2000 | Eliasen et al. |
| 6,090,067 A | 7/2000 | Carter |
| 6,090,068 A | 7/2000 | Chanut |
| 6,102,884 A | 8/2000 | Squitieri |
| 6,120,492 A | 9/2000 | Finch et al. |
| 6,190,349 B1 | 2/2001 | Ash et al. |
| 6,190,352 B1 | 2/2001 | Haarala et al. |
| 6,206,851 B1 | 3/2001 | Prosl |
| 6,213,973 B1 | 4/2001 | Eliasen et al. |
| D445,175 S | 7/2001 | Bertheas |
| 6,287,293 B1 | 9/2001 | Jones et al. |
| 6,332,874 B1 | 12/2001 | Eliasen et al. |
| 6,350,251 B1 | 2/2002 | Prosl et al. |
| 6,352,521 B1 | 3/2002 | Prosl |
| 6,398,764 B1 | 6/2002 | Finch, Jr. et al. |
| 6,436,084 B1 | 8/2002 | Finch et al. |
| 6,438,397 B1 | 8/2002 | Bosquet et al. |
| 6,459,917 B1 | 10/2002 | Gowda et al. |
| 6,478,783 B1 | 11/2002 | Moorehead |
| 6,482,197 B2 | 11/2002 | Finch et al. |
| 6,494,867 B1 | 12/2002 | Elver et al. |
| 6,506,182 B2 | 1/2003 | Estabrook et al. |
| 6,527,754 B1 | 3/2003 | Tallarida et al. |
| 6,540,717 B2 | 4/2003 | Sherry |
| 6,562,023 B1 | 5/2003 | Marrs et al. |
| 6,565,525 B1 | 5/2003 | Burbank et al. |
| 6,582,409 B1 | 6/2003 | Squitieri |
| 6,607,504 B2 | 8/2003 | Haarala et al. |
| 6,620,118 B1 | 9/2003 | Prosl et al. |
| 6,695,832 B2 | 2/2004 | Schon et al. |
| 6,699,218 B2 | 3/2004 | Flaherty et al. |
| 6,719,749 B1 | 4/2004 | Schweikert et al. |
| 6,726,711 B1 | 4/2004 | Langenbach et al. |
| 6,758,841 B2 | 7/2004 | Haarala et al. |
| 6,783,522 B2 | 8/2004 | Fischell |
| 6,852,106 B2 | 2/2005 | Watson et al. |
| 6,881,211 B2 | 4/2005 | Schweikert et al. |
| 6,929,631 B1 | 8/2005 | Brugger et al. |
| 6,960,185 B2 | 11/2005 | Adaniya et al. |
| 6,962,580 B2 | 11/2005 | Adams et al. |
| 6,997,914 B2 | 2/2006 | Smith et al. |
| 7,018,374 B2 | 3/2006 | Schon et al. |
| 7,056,316 B1 | 6/2006 | Burbank et al. |
| 7,070,591 B2 | 7/2006 | Adams et al. |
| 7,083,648 B2 | 8/2006 | Yu et al. |
| 7,108,686 B2 | 9/2006 | Burke et al. |
| 7,131,962 B1 | 11/2006 | Estabrook et al. |
| 7,223,257 B2 | 5/2007 | Shubayev et al. |
| 7,261,705 B2 | 8/2007 | Edoga et al. |
| 7,311,702 B2 | 12/2007 | Tallarida et al. |
| 7,322,953 B2 | 1/2008 | Redinger |
| D562,443 S | 2/2008 | Zinn et al. |
| 7,347,843 B2 | 3/2008 | Adams et al. |
| 7,351,233 B2 | 4/2008 | Parks |
| 7,396,359 B1 | 7/2008 | Derowe et al. |
| D574,950 S | 8/2008 | Zawacki et al. |
| D578,203 S | 10/2008 | Bizup |
| 7,445,614 B2 | 11/2008 | Bunodiere et al. |
| D582,032 S | 12/2008 | Bizup et al. |
| 7,497,850 B2 | 3/2009 | Halili |
| D612,479 S | 3/2010 | Zawacki et al. |
| 7,699,821 B2 | 4/2010 | Nowak |
| 7,704,225 B2 | 4/2010 | Kantrowitz |
| 7,708,722 B2 | 5/2010 | Glenn |
| 7,713,251 B2 | 5/2010 | Tallarida et al. |
| 7,731,680 B2 | 6/2010 | Patton |
| 7,762,999 B2 | 7/2010 | Byrum |
| 7,824,365 B2 | 11/2010 | Haarala et al. |
| 7,846,139 B2 | 12/2010 | Zinn et al. |
| 7,850,666 B2 | 12/2010 | Schon et al. |
| 7,909,804 B2 | 3/2011 | Stats |
| 7,959,615 B2 | 6/2011 | Stats et al. |

| | | | |
|---|---|---|---|
| 7,972,315 B2 | 7/2011 | Birk et al. |
| 7,981,094 B2 | 7/2011 | Chelak |
| D650,475 S | 12/2011 | Smith et al. |
| 8,075,536 B2 | 12/2011 | Gray et al. |
| 8,079,990 B2 | 12/2011 | Powley et al. |
| 8,147,455 B2 | 4/2012 | Butts et al. |
| 8,152,792 B1 | 4/2012 | Kornel |
| 8,257,325 B2 | 9/2012 | Schweikert et al. |
| 8,277,425 B2 | 10/2012 | Girard et al. |
| 8,328,768 B2 | 12/2012 | Quigley et al. |
| 8,337,464 B2 | 12/2012 | Young et al. |
| 8,337,465 B2 | 12/2012 | Young et al. |
| 8,337,470 B2 | 12/2012 | Prasad et al. |
| 8,343,108 B2 | 1/2013 | Rosenberg et al. |
| 8,364,230 B2 | 1/2013 | Simpson et al. |
| 8,377,034 B2 | 2/2013 | Tallarida et al. |
| 8,425,416 B2 | 4/2013 | Brister et al. |
| 8,425,476 B2 | 4/2013 | Glenn |
| 8,480,560 B2 | 7/2013 | Vendely |
| 8,550,981 B2 | 10/2013 | Woodruff et al. |
| 8,574,204 B2 | 11/2013 | Bourne et al. |
| RE44,639 E | 12/2013 | Squitieri |
| 8,622,980 B2 | 1/2014 | Zinn |
| 8,690,815 B2 | 4/2014 | Porter et al. |
| 8,690,816 B2 | 4/2014 | Dakin et al. |
| 8,738,151 B2 | 5/2014 | Nelson |
| 8,979,806 B2 | 3/2015 | Saab |
| 9,033,931 B2 | 5/2015 | Young et al. |
| 9,061,129 B2 | 6/2015 | Lauer |
| 9,072,880 B2 | 7/2015 | Phillips et al. |
| 9,072,881 B2 | 7/2015 | Dalton et al. |
| 9,078,982 B2 | 7/2015 | Lane et al. |
| 9,089,395 B2 | 7/2015 | Honaryar |
| 9,095,665 B2 | 8/2015 | Pages et al. |
| 9,138,563 B2 | 9/2015 | Glenn |
| 9,168,365 B2 | 10/2015 | Bourne et al. |
| 9,174,037 B2 | 11/2015 | Schutz et al. |
| 9,179,901 B2 | 11/2015 | Young et al. |
| 9,180,248 B2 | 11/2015 | Moberg et al. |
| 9,474,888 B2 | 10/2016 | Wiley et al. |
| 9,579,496 B2 | 2/2017 | Evans et al. |
| 9,707,339 B2 | 7/2017 | Chartrand et al. |
| 9,987,467 B2 | 6/2018 | Jochum |
| 10,207,095 B2 | 2/2019 | Barron et al. |
| 10,272,236 B2 | 4/2019 | Davey |
| 10,463,845 B2 | 11/2019 | Stats et al. |
| D870,264 S | 12/2019 | Fedor et al. |
| D885,557 S | 5/2020 | Fedor et al. |
| 10,967,152 B2 | 4/2021 | Korkuch |
| 11,090,466 B1 | 8/2021 | Nicholson |
| 11,420,033 B2 * | 8/2022 | Fedor .............. A61M 39/0208 |
| 11,464,960 B2 | 10/2022 | Fedor et al. |
| 2001/0041870 A1 | 11/2001 | Gillis et al. |
| 2001/0056266 A1 | 12/2001 | Tallarida et al. |
| 2002/0099326 A1 | 7/2002 | Wilson et al. |
| 2003/0023208 A1 | 1/2003 | Osypka et al. |
| 2003/0181878 A1 | 9/2003 | Tallarida et al. |
| 2004/0054352 A1 | 3/2004 | Adams et al. |
| 2004/0073196 A1 | 4/2004 | Adams et al. |
| 2004/0199129 A1 | 10/2004 | DiMatteo |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2005/0075614 A1 | 4/2005 | Bunodiere et al. |
| 2005/0113806 A1 | 5/2005 | De Carvalho et al. |
| 2005/0131352 A1 | 6/2005 | Conlon et al. |
| 2005/0148956 A1 | 7/2005 | Conlon et al. |
| 2005/0148957 A1 | 7/2005 | Girard et al. |
| 2005/0171502 A1 | 8/2005 | Daly et al. |
| 2005/0203484 A1 | 9/2005 | Nowak |
| 2005/0209573 A1 | 9/2005 | Brugger et al. |
| 2005/0256451 A1 | 11/2005 | Adams et al. |
| 2005/0277899 A1 | 12/2005 | Conlon et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0173424 A1 | 8/2006 | Conlon |
| 2006/0178617 A1 | 8/2006 | Adams et al. |
| 2006/0178647 A1 | 8/2006 | Stats |

(56)                    References Cited

U.S. PATENT DOCUMENTS

| | | |
|---|---|---|
| 2006/0184142 A1 | 8/2006 | Schon et al. |
| 2006/0217659 A1 | 9/2006 | Patton |
| 2006/0217673 A1 | 9/2006 | Schulze et al. |
| 2006/0224129 A1 | 10/2006 | Beasley et al. |
| 2006/0247584 A1 | 11/2006 | Sheetz et al. |
| 2006/0264898 A1 | 11/2006 | Beasley et al. |
| 2006/0271012 A1 | 11/2006 | Canaud et al. |
| 2006/0293626 A1 | 12/2006 | Byrum et al. |
| 2007/0049806 A1 | 3/2007 | Adams et al. |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0083156 A1 | 4/2007 | Muto et al. |
| 2007/0161958 A1 | 7/2007 | Glenn |
| 2007/0179456 A1 | 8/2007 | Glenn |
| 2007/0208313 A1 | 9/2007 | Conlon et al. |
| 2007/0219510 A1 | 9/2007 | Zinn et al. |
| 2007/0232997 A1 | 10/2007 | Glenn |
| 2007/0233017 A1 | 10/2007 | Zinn et al. |
| 2007/0233018 A1 | 10/2007 | Bizup et al. |
| 2007/0255234 A1 | 11/2007 | Haase et al. |
| 2007/0270770 A1 | 11/2007 | Bizup |
| 2007/0276344 A1 | 11/2007 | Bizup et al. |
| 2007/0282308 A1 | 12/2007 | Bell |
| 2008/0048855 A1 | 2/2008 | Berger |
| 2008/0086075 A1 | 4/2008 | Isik et al. |
| 2008/0108942 A1 | 5/2008 | Brister et al. |
| 2008/0114308 A1 | 5/2008 | di Palma et al. |
| 2008/0132946 A1 | 6/2008 | Mueller |
| 2008/0208236 A1 | 8/2008 | Hobbs et al. |
| 2008/0249509 A1 | 10/2008 | Glenn |
| 2008/0281279 A1 | 11/2008 | Hoendervoogt et al. |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1* | 1/2009 | Bizup ............... A61M 39/0208 |
| | | 604/288.02 |
| 2009/0076466 A1 | 3/2009 | Quebbemann et al. |
| 2009/0099526 A1* | 4/2009 | Powley ............. A61M 39/0208 |
| | | 604/175 |
| 2009/0105688 A1 | 4/2009 | McIntyre et al. |
| 2009/0118683 A1* | 5/2009 | Hanson ............. A61M 39/0208 |
| | | 604/288.03 |
| 2009/0156928 A1 | 6/2009 | Evans et al. |
| 2009/0192467 A1 | 7/2009 | Hansen et al. |
| 2009/0204074 A1 | 8/2009 | Powers et al. |
| 2009/0221976 A1 | 9/2009 | Linden |
| 2009/0259164 A1 | 10/2009 | Pages et al. |
| 2010/0042073 A1 | 2/2010 | Oster et al. |
| 2010/0121283 A1 | 5/2010 | Hamatake et al. |
| 2010/0121313 A1 | 5/2010 | Goode et al. |
| 2010/0298684 A1 | 11/2010 | Leach et al. |
| 2011/0034886 A1 | 2/2011 | Elbe et al. |
| 2011/0118677 A1 | 5/2011 | Wiley et al. |
| 2011/0257577 A1 | 10/2011 | Lane et al. |
| 2011/0264058 A1 | 10/2011 | Linden et al. |
| 2011/0319728 A1 | 12/2011 | Petisce et al. |
| 2012/0172711 A1 | 7/2012 | Kerr et al. |
| 2012/0283518 A1 | 11/2012 | Hart |
| 2013/0030348 A1 | 1/2013 | Lauer |
| 2013/0046224 A1 | 2/2013 | Ravenscroft et al. |
| 2013/0150767 A1 | 6/2013 | Tsyrulnykov et al. |
| 2013/0150811 A1 | 6/2013 | Horgan |
| 2014/0024998 A1 | 1/2014 | Prosl et al. |
| 2014/0207086 A1 | 7/2014 | Stats et al. |
| 2014/0243789 A1 | 8/2014 | Mehta et al. |
| 2015/0190622 A1 | 7/2015 | Saab |
| 2015/0196704 A1 | 7/2015 | Adler |
| 2015/0231369 A1 | 8/2015 | Gray et al. |
| 2015/0250933 A1 | 9/2015 | Kerkhoffs et al. |
| 2015/0258322 A1 | 9/2015 | Young et al. |
| 2015/0265280 A1 | 9/2015 | Blatter et al. |
| 2015/0273201 A1 | 10/2015 | Tallarida et al. |
| 2015/0290446 A1 | 10/2015 | Wiley et al. |
| 2015/0306300 A1 | 10/2015 | Phillips et al. |
| 2015/0327844 A1 | 11/2015 | Hong et al. |
| 2016/0001055 A1 | 1/2016 | Bourne et al. |
| 2016/0067470 A1 | 3/2016 | Silva Pires e Albuquerque |
| 2017/0143890 A1 | 5/2017 | Nardeo |
| 2018/0078751 A1 | 3/2018 | Fedor et al. |
| 2019/0070399 A1 | 3/2019 | Casiello et al. |
| 2019/0232035 A1 | 8/2019 | Fedor et al. |
| 2020/0323557 A1 | 10/2020 | Chavan et al. |
| 2022/0401703 A1 | 12/2022 | Gooch et al. |
| 2023/0032423 A1 | 2/2023 | Fedor et al. |
| 2024/0269448 A1 | 8/2024 | Densley et al. |

FOREIGN PATENT DOCUMENTS

| | | |
|---|---|---|
| CA | 2551680 A1 | 7/2005 |
| CN | 102271737 A | 12/2011 |
| EP | 0229729 A2 | 7/1987 |
| EP | 0366814 A1 | 5/1990 |
| EP | 0 809 523 A1 | 12/1997 |
| EP | 1047473 A1 | 11/2000 |
| EP | 1056506 A1 | 12/2000 |
| EP | 810893 B1 | 7/2002 |
| EP | 2179763 A1 | 4/2010 |
| EP | 2948121 B1 | 11/2017 |
| JP | H05-506591 A | 9/1993 |
| JP | H07-148206 A | 6/1995 |
| JP | H08-501008 A | 2/1996 |
| JP | 2008-531226 A | 8/2008 |
| NO | 1998017337 A1 | 4/1998 |
| WO | 1991/012838 A1 | 9/1991 |
| WO | 1993005730 A1 | 4/1993 |
| WO | 1994005246 A1 | 3/1994 |
| WO | 96/25196 A1 | 8/1996 |
| WO | 1996029112 A1 | 9/1996 |
| WO | 1997001370 A1 | 1/1997 |
| WO | 1997006845 A1 | 2/1997 |
| WO | 1999034859 A1 | 7/1999 |
| WO | 99/42166 A1 | 8/1999 |
| WO | 2000033901 A1 | 6/2000 |
| WO | 2000044424 A1 | 8/2000 |
| WO | 2000053245 A1 | 9/2000 |
| WO | 2001026713 A1 | 4/2001 |
| WO | 01/80926 A2 | 11/2001 |
| WO | 2002038460 A1 | 5/2002 |
| WO | 2002066595 A1 | 8/2002 |
| WO | 2003066126 A2 | 8/2003 |
| WO | 2004004800 A2 | 1/2004 |
| WO | 2004071555 A2 | 8/2004 |
| WO | 2004091434 A2 | 10/2004 |
| WO | 2004093970 A1 | 11/2004 |
| WO | 2005068009 A1 | 7/2005 |
| WO | 2006064753 A1 | 6/2006 |
| WO | 2006078915 A2 | 7/2006 |
| WO | 2006096686 A1 | 9/2006 |
| WO | 2006/116438 A2 | 11/2006 |
| WO | 2006130133 A1 | 12/2006 |
| WO | 2006134100 A1 | 12/2006 |
| WO | 2007079024 A2 | 7/2007 |
| WO | 2007082003 A2 | 7/2007 |
| WO | 2007087460 A2 | 8/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008048361 A1 | 4/2008 |
| WO | 2008063226 A2 | 5/2008 |
| WO | 2008140901 A1 | 11/2008 |
| WO | 2008157763 A1 | 12/2008 |
| WO | 2009002839 A1 | 12/2008 |
| WO | 2009/012385 A1 | 1/2009 |
| WO | 2009035582 A1 | 3/2009 |
| WO | 2009046439 A2 | 4/2009 |
| WO | 2009108669 A1 | 9/2009 |
| WO | 2012064881 A2 | 5/2012 |
| WO | 2014017986 A1 | 1/2014 |
| WO | 2014116810 A1 | 7/2014 |
| WO | 2015179862 A1 | 11/2015 |

(56)          References Cited

FOREIGN PATENT DOCUMENTS

| WO | 2019/200304 | A1 | 10/2019 |
| WO | 2021/061095 | A1 | 4/2021 |
| WO | 2021078488 | A1 | 4/2021 |
| WO | 2022235276 | A1 | 11/2022 |
| WO | 2023077276 | A1 | 5/2023 |

OTHER PUBLICATIONS

Canaud, B. et. al. "Dialock: a new vascular access device for extracorporeal renal replacement therapy. Preliminary clinical results" —Mar. 1999.
CN 201480005902.2 filed Jul. 23, 2015 Office Action dated Jan. 20, 2016.
CN 201480005902.2 filed Jul. 23, 2015 Office Action dated Jul. 19, 2016.
CN 201480005902.2 filed Jul. 23, 2015 Office Action dated May 12, 2017.
EP 14743846.9 filed Aug. 12, 2015 Extended European Search Report dated Oct. 10, 2016.
EP 14743846.9 filed Aug. 12, 2015 Intent to Grant dated Jun. 26, 2017.
EP 17870333.6 filed Jun. 7, 2019 Supplemental European Search Report dated May 26, 2020.
Goldstein, D. J. et. al. "Implantable Left Ventricular Assist Devices" (Nov. 19, 1998).
JP 2015-555266 filed Jul. 22, 2015 Office Action dated May 2, 2018.
JP 2015-555266 filed Jul. 22, 2015 Office Action dated Oct. 12, 2017.
Moran, J. E. "Subcutaneous Vascular Access Devices" (Nov. 1, 2001).
PCT/US2014/012721 filed Jan. 23, 2014 International Search Report and Written Opinion dated Apr. 14, 2014.
PCT/US2017/061179 filed Nov. 10, 2017 International Search Report and Written Opinion dated Jan. 22, 2018.
PCT/US2019/027301 filed Nov. 12, 2020 Extended European Search Report dated Oct. 11, 2021.
PCTUS2019052477 filed Sep. 23, 2019 International Search Report and Written Opinion dated Mar. 11, 2020.
Rosenblatt, M. et. al. "Efficacy and Safety Results with the LifeSite Hemodialysis Access System versus the Tesio-Cath Hemodialysis Catheter at 12 Months"—Mar. 2006.
Sandhu, J. Dialysis Ports: A New Totally Implantable Option for Hemodialysis Access—Jun. 2002.
U.S. Appl. No. 14/162,113, filed Jan. 23, 2014 Final Office Action dated Jul. 2, 2018.
U.S. Appl. No. 14/162,113, filed Jan. 23, 2014 Final Office Action dated May 25, 2017.
U.S. Appl. No. 14/162,113, filed Jan. 23, 2014 Non-Final Office Action dated Dec. 11, 2017.
U.S. Appl. No. 14/162,113, filed Jan. 23, 2014 Non-Final Office Action dated May 4, 2016.
U.S. Appl. No. 14/162,113, filed Jan. 23, 2014 Non-Final Office Action dated Nov. 22, 2016.
U.S. Appl. No. 14/162,113, filed Jan. 23, 2014 Notice of Allowance dated Aug. 14, 2019.
U.S. Appl. No. 15/809,879, filed Nov. 10, 2017 Final Office Action dated May 18, 2021.
U.S. Appl. No. 15/809,879, filed Nov. 10, 2017 Final Office Action dated Nov. 5, 2020.
U.S. Appl. No. 15/809,879, filed Nov. 10, 2017 Final Office Action dated Oct. 4, 2021.
U.S. Appl. No. 15/809,879, filed Nov. 10, 2017 Non-Final Office Action dated Jun. 10, 2020.
U.S. Appl. No. 15/809,879, filed Nov. 10, 2017 Notice of Allowance dated May 4, 2022.
U.S. Appl. No. 29/616,511, filed Sep. 6, 2017 Notice of Allowance dated Aug. 8, 2019.
U.S. Appl. No. 29/716,554, filed Dec. 10, 2019 Notice of Allowance dated Feb. 6, 2020.
U.S. Appl. No. 17/763,154, filed Mar. 23, 2022 Final Office Action dated Jul. 25, 2025.
U.S. Appl. No. 17/763,154, filed Mar. 23, 2022 Non-Final Office Action dated Feb. 11, 2025.
U.S. Appl. No. 17/963,813, filed Oct. 11, 2022 Restriction Requirement dated Jul. 23, 2025.
PCT/US2021/031407 filed May 7, 2021 International Search Report and Written Opinion dated Feb. 4, 2022.
PCT/CN2021/128248 filed Nov. 2, 2021 International Search Report and Written Opinion dated Apr. 25, 2022.
U.S. Appl. No. 17/763,154, filed Mar. 23, 2022 Advisory Action dated Oct. 20, 2025.
U.S. Appl. No. 17/763,154, filed Mar. 23, 2022 Non-Final Office Action dated Nov. 17, 2025.
U.S. Appl. No. 17/963,813, filed Oct. 11, 2022 Non-Final Office Action dated Oct. 21, 2025.

* cited by examiner

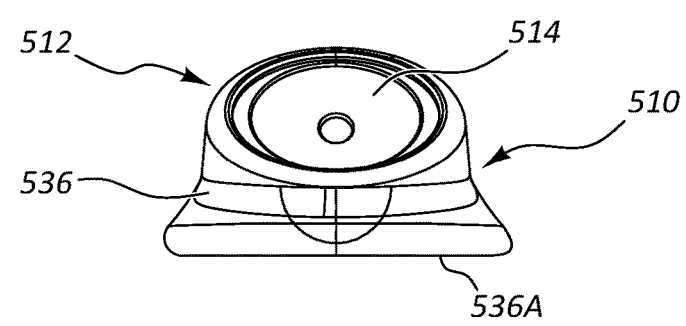
FIG. 9D
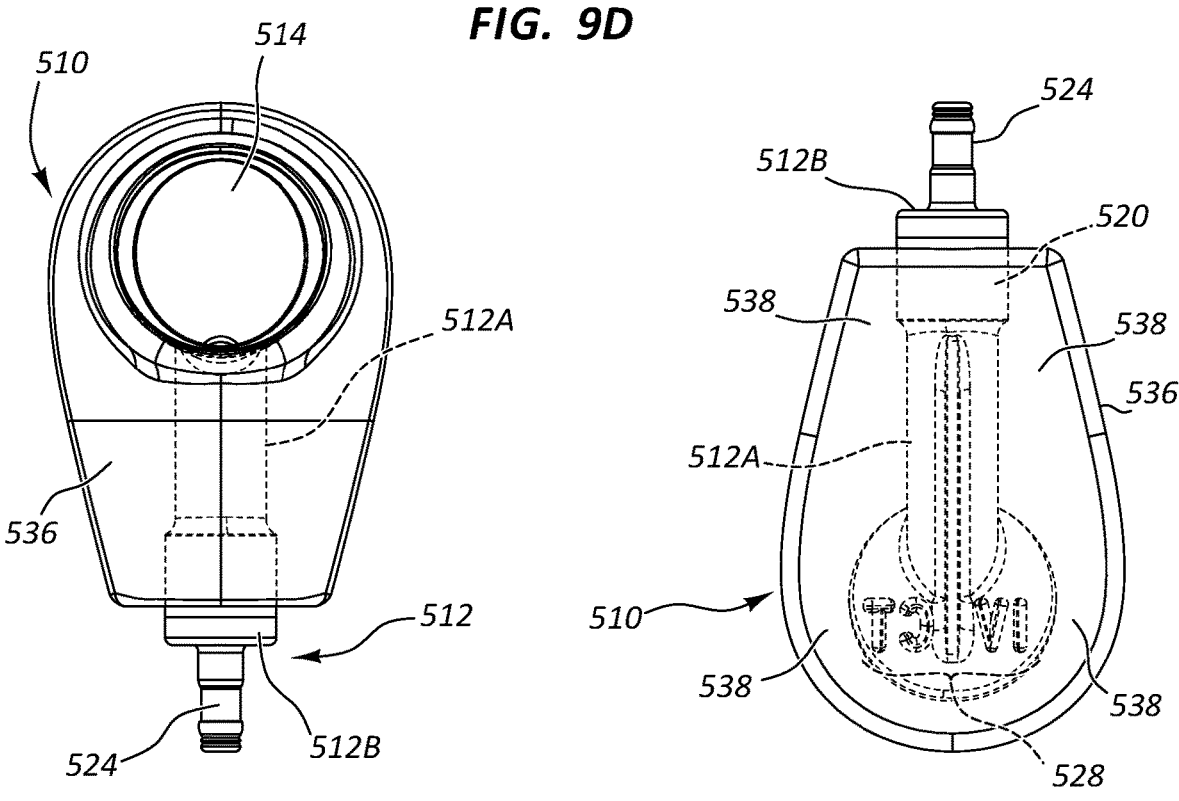
FIG. 9E
FIG. 9F
FIG. 9G

LOW-PROFILE SINGLE AND DUAL VASCULAR ACCESS DEVICE

CROSS-REFERENCE TO RELATED APPLICATIONS

This application is a continuation of U.S. patent application Ser. No. 15/809,879, filed Nov. 10, 2017, now U.S. Pat. No. 11,420,033, which is a continuation-in-part of U.S. patent application Ser. No. 14/162,113, filed Jan. 23, 2014, now U.S. Pat. No. 10,463,845, which claims the benefit of U.S. Provisional Application No. 61/755,913, filed Jan. 23, 2013. This application, via U.S. patent application Ser. No. 15/809,879, also claims the benefit of U.S. Provisional Application No. 62/421,131, filed Nov. 11, 2016, and U.S. Provisional Application No. 62/552,681, filed Aug. 31, 2017. Each of the aforementioned applications is incorporated herein by reference in its entirety.

BRIEF SUMMARY

Briefly summarized, embodiments of the present invention are directed to a low-profile access port for subcutaneous implantation within the body of a patient. The access port includes a receiving cup that provides a relatively large subcutaneous target to enable a catheter-bearing needle to access the port without difficulty. In addition, the access port includes a valve/seal assembly to permit pressurized fluid injection through the port while preventing backflow.

In one embodiment, therefore, a low-profile access port comprises a body including a conduit with an inlet port at a proximal end thereof, and a receiving cup. The receiving cup is concavely shaped to direct a catheter-bearing needle into the conduit via the inlet port. The receiving cup is oriented substantially toward a skin surface when subcutaneously implanted within the patient to ease needle impingement thereon. A valve/seal assembly disposed in the conduit enables passage of the catheter therethrough while preventing fluid backflow.

In another embodiment, a low-profile access port for subcutaneous implantation within the patient is disclosed and comprises a body including a conduit with an inlet port at a proximal end thereof, and a receiving cup. The receiving cup is funnel shaped to direct a catheter-bearing needle into the conduit via the inlet port. The conduit is defined by the body and extends from the inlet port to an outlet defined by a stem. A bend in the conduit enables catheter advancement past the bend while preventing needle advancement. A valve/seal assembly is also disposed in the conduit and enables passage of the catheter therethrough while preventing fluid backflow. The body includes radiopaque indicia configured to enable identification of the access port via x-ray imaging.

In light of the above, embodiments herein are generally directed to a vascular access device, also referred to herein as an access port, for subcutaneous implantation within the body of a patient. The implanted access port is transcutaneously accessible by a catheter-bearing needle, such as a peripheral intravenous ("PIV") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 9A-9G depict various views of a low-profile vascular access device according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an access port for subcutaneous implantation within the body of a patient. The implanted access port is transcutaneously accessible by a catheter-bearing needle, such as a peripheral intravenous ("PIV") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter.

In accordance with one embodiment, the access port defines a low profile so as to facilitate ease of placement within the subcutaneous tissue of the patient. Further, the access port is configured to provide a relatively large subcutaneous target to enable the PIV catheter or other suitable catheter-bearing needle to access the port without difficulty. In addition, the access port includes a valve/seal assembly to permit the injection of fluids through the access port at a relatively high flow rate, such as about 5 ml per second at a pressure of about 300 psi (also referred to herein as "power injection"). Possible applications for the access port described herein include administration of medicaments and other fluids to the patient, pheresis/apheresis, fluid aspiration, etc.

Figure 1A:
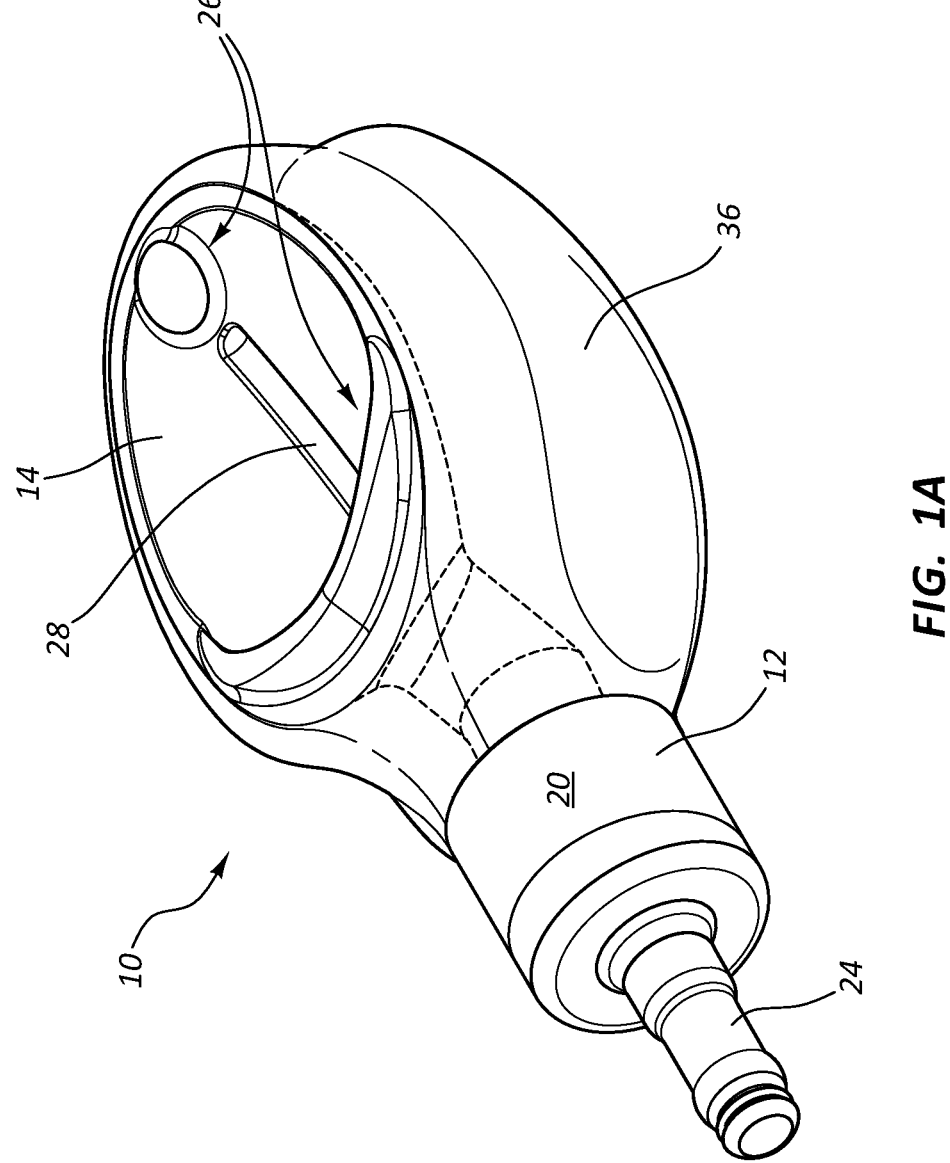
FIGS. 1A-1E show various views of an access port according to one embodiment.
Figures 1B, 1C:
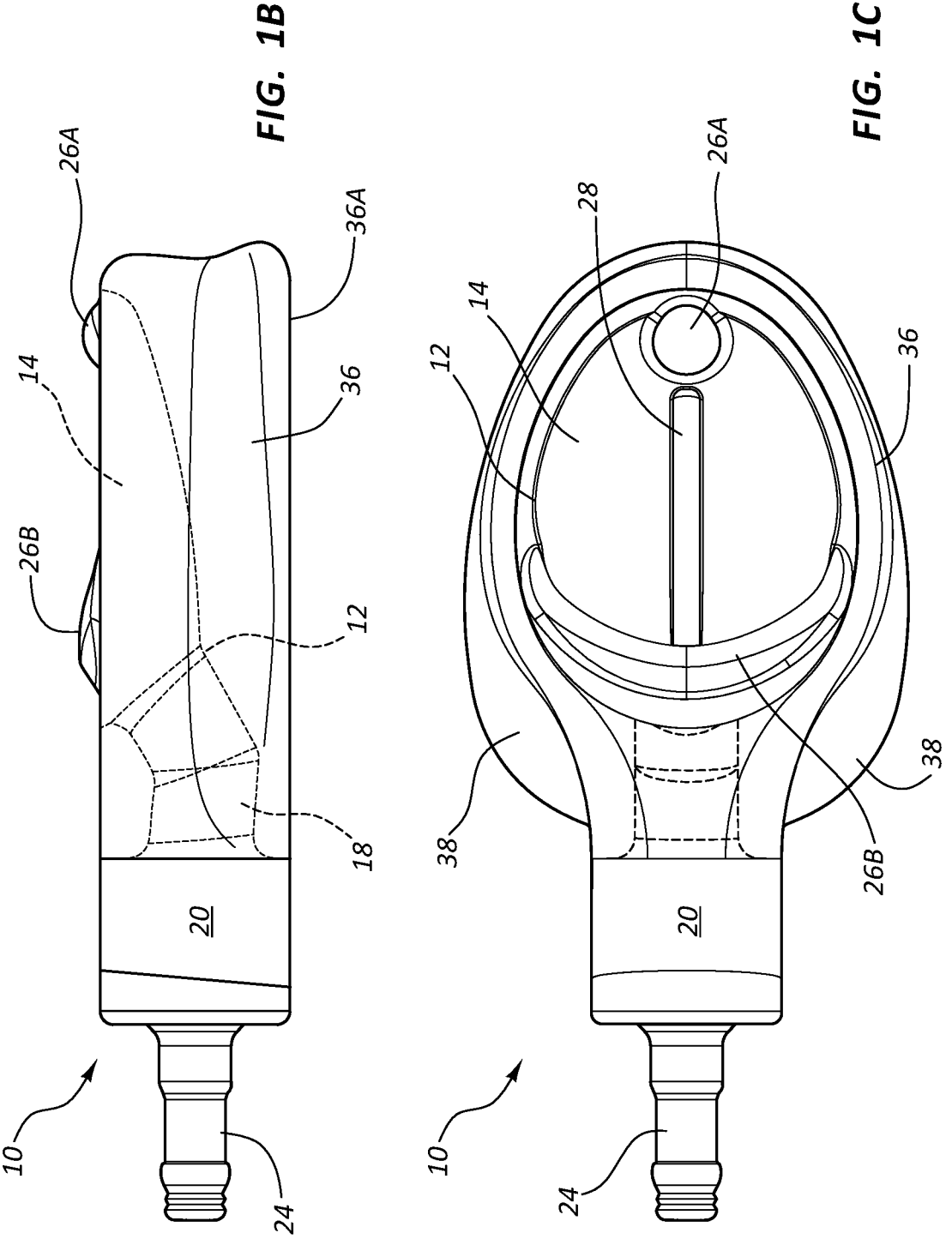
Figure 1D:
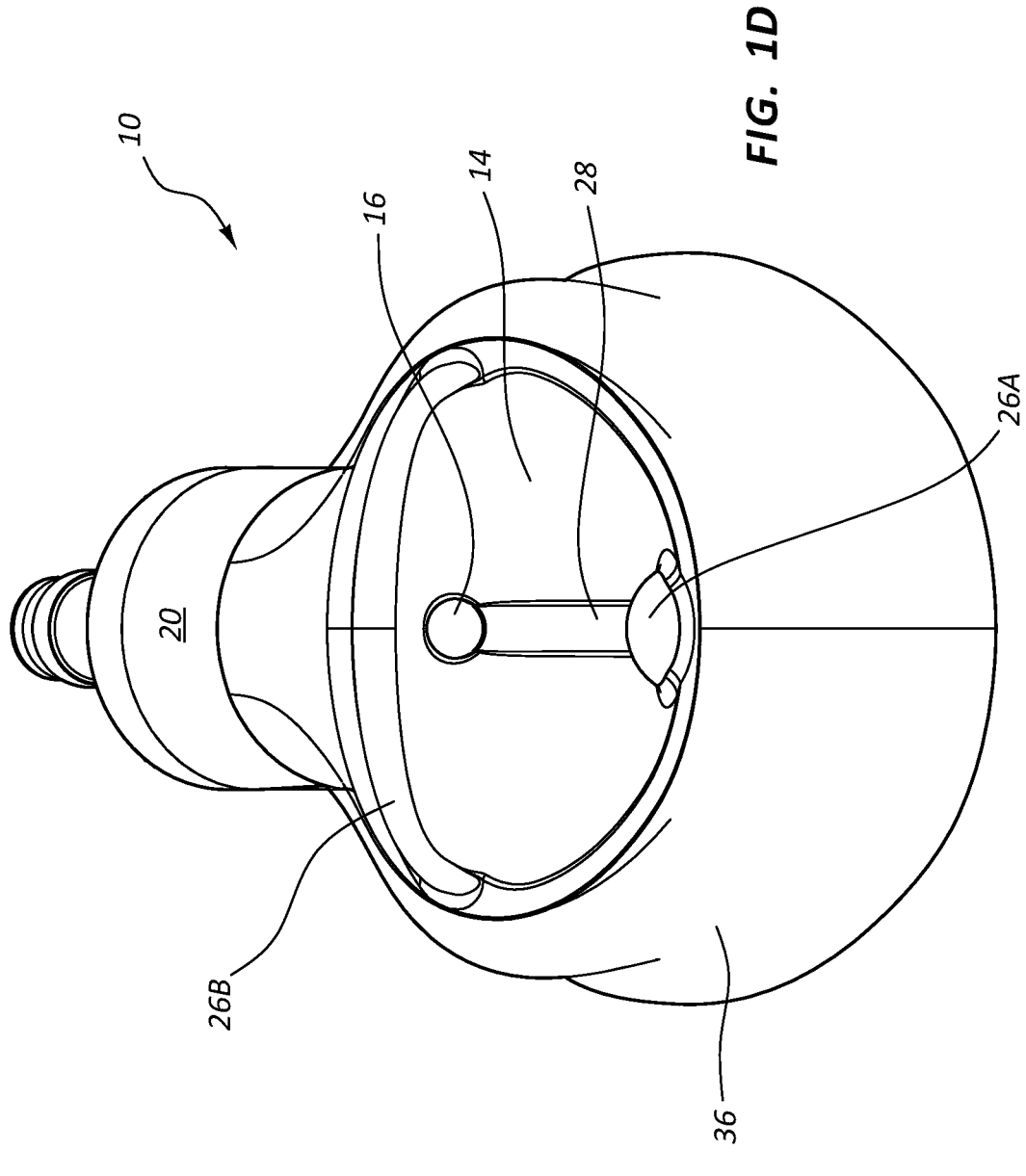
Figure 1E:
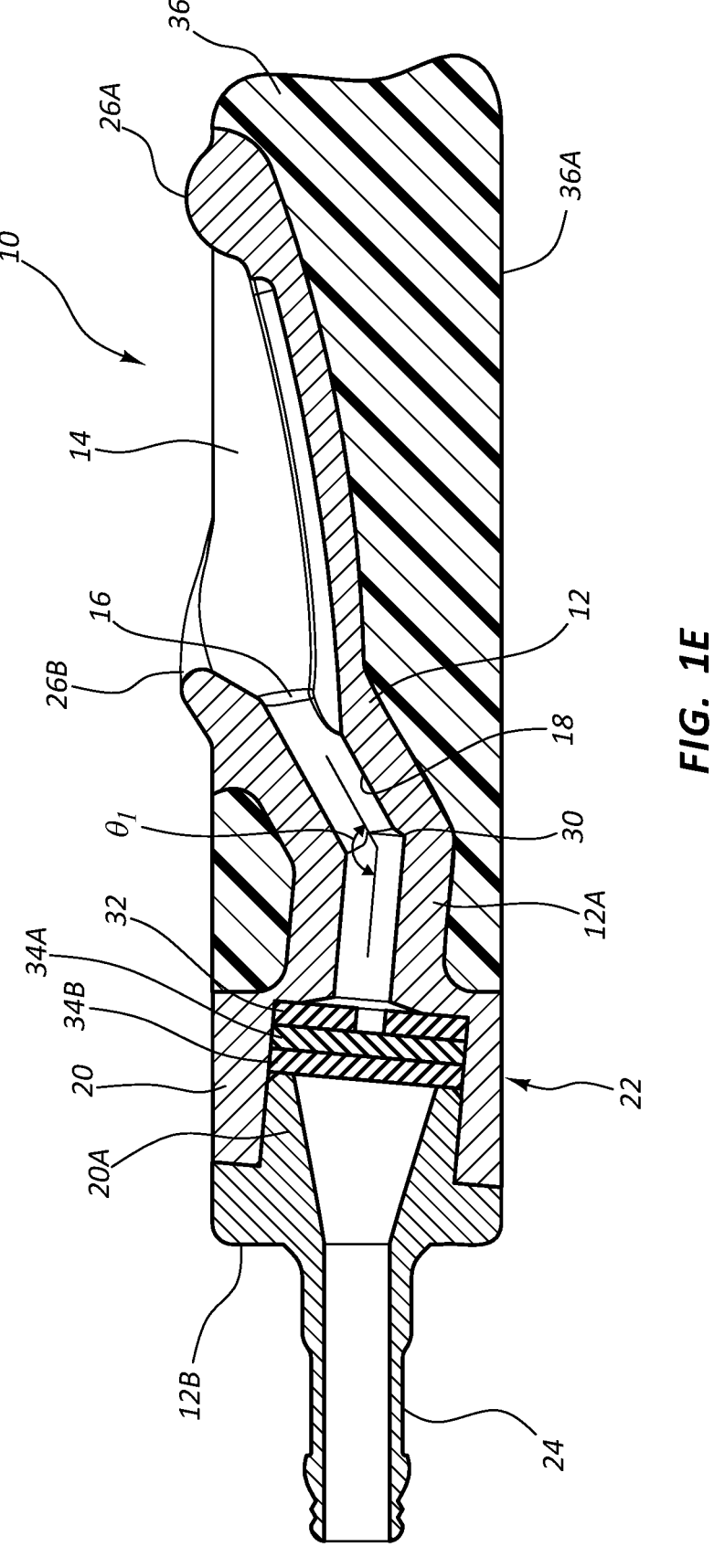

Reference is first made to made to FIGS. 1A-1E, which show various details of an access port, generally designated at 10, in accordance with one embodiment. As shown, the port 10 includes a body 12 that is defined in the present embodiment by a first portion 12A and a second portion 12B (FIG. 1E). In the present embodiment the port body 12 includes a metal such as titanium, and as such, the second portion 12B is press fit into engagement with the first portion 12A to define the body, though it is appreciated that the port body can include a variety of other materials, including metals, thermoplastics, ceramics, etc.

Figure 2:
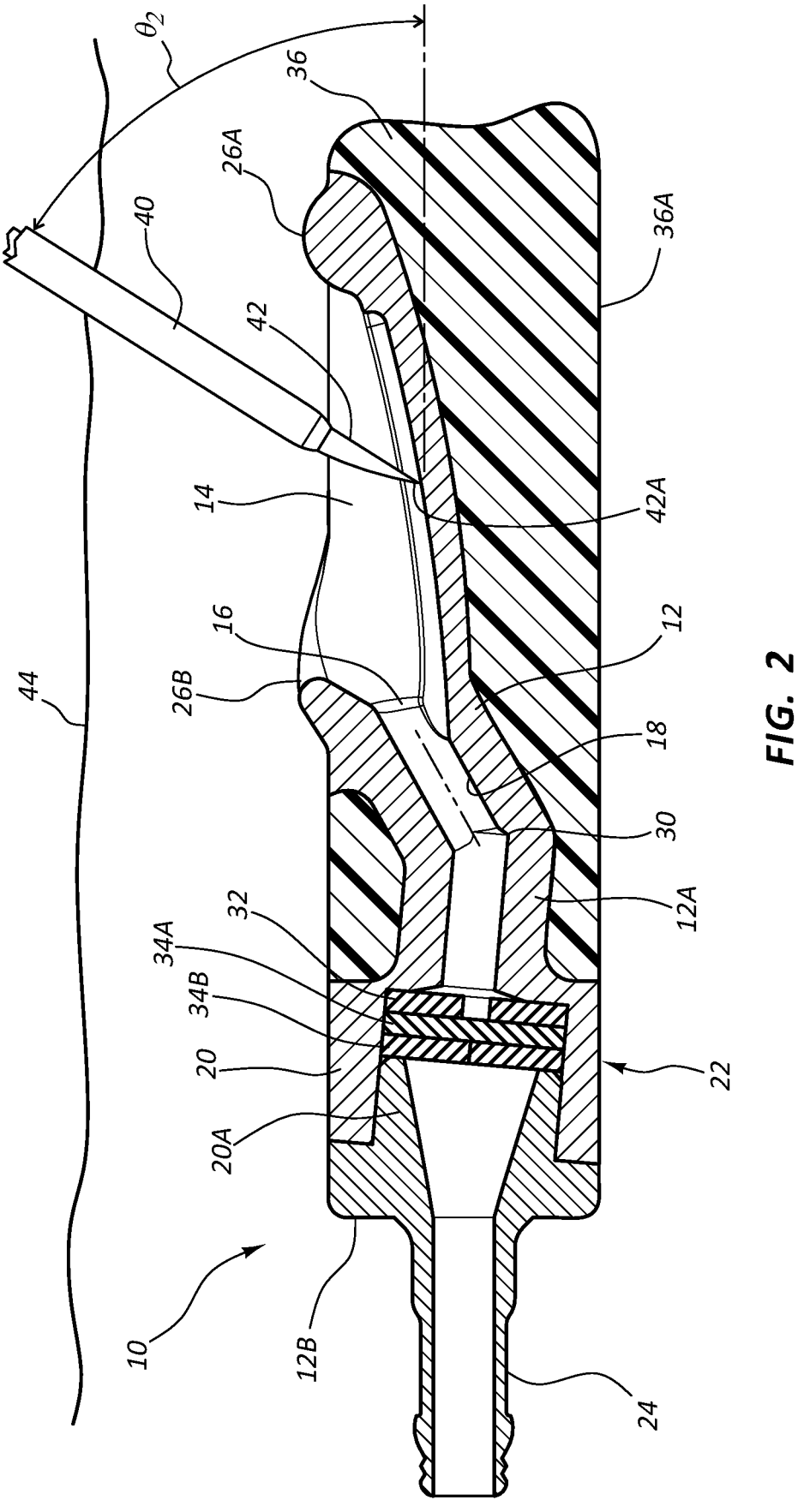
FIG. 2 is a cross sectional view of the access port of FIGS. 1A-1E.

The port body 12 defines in the present embodiment a substantially concavely-shaped receiving cup 14 for receiving and directing a catheter-bearing needle (FIG. 2) to operably connect with the port 10, as described further below. In particular, the substantially concave shape of the receiving cup 14 is configured to direct a catheter-bearing needle (FIG. 2) impinging thereon toward an inlet port 16 that serves as an opening for a conduit 18 defined by the port body 12. The open and shallow nature of the receiving cup 14 together with its substantially upward orientation (i.e., toward the skin surface of the patient), so that it is substantially parallel to the skin surface when subcutaneously implanted under the skin of the patient (i.e., the receiving cup is substantially parallel to the skin surface when the skin is at rest, or undeformed by digital pressure or manipulation), enables the receiving cup to present a large, easily accessible target for the needle when introduced into the skin, as seen in FIG. 2. FIG. 2 further shows that the port 10 defines a relatively low profile height, which enables relatively shorter needle lengths to be used for accessing the port after implantation.

Palpation features 26 are included with the port body 12 to assist a clinician to locate and/or identify the port 10 via finger palpation after implantation under the skin of the patient. In detail, the palpation features 26 in the present embodiment include a bump 26A disposed near the proximal end of the receiving cup 14 and a ridge 26B disposed above and curving around a distal portion of the receiving cup. FIG. 1B shows that the palpation features extend above the general upper plane defined by the port 10 so as to facilitate palpation of the features by a clinician in order to locate the position and/or orientation of the receiving cup 14. Note that a variety of other sizes, configurations, numbers, etc., of palpation features can be included on the port in addition to what is shown and described herein.

A guide groove 28 is defined on the receiving cup 14 and is longitudinally aligned with the inlet port 16 of the conduit 18. The guide groove 28 is defined as a depression with respect to adjacent portions of the surface of the receiving cup 14 and extends distally along the receiving cup surface from a proximal portion of the receiving cup so as to provide a guide path to guide the distal tip of the catheter-bearing needle toward the inlet port 16 once impingement of the needle into the guide groove is made. This in turn reduces the chance the needle will slide across and off the receiving cup 14 during insertion. Note that these and other similar features, though differing in shape and configuration, can also be included on the other ports disclosed herein.

As best seen in FIG. 1E, the port body 12 further defines the conduit 18 as a pathway into which a transcutaneously inserted catheter can pass so as to place the catheter in fluid communication with the port 10. As shown, the conduit 18 is in communication with the receiving cup 14 via the inlet port 16. A first conduit portion 18A of the conduit 18 distally extends from the inlet port 16 in an angled downward direction from the perspective shown in FIG. 1E to a bend 30, where a second conduit portion 18B of the conduit angles slightly upward and changes direction at a predetermined angle $(180-\theta_l)$. Note that angle orientation angle $(180-\theta_1)$ in one embodiment is about 37 degrees, but can vary from this in other embodiments, including angles less than 37 degrees in one embodiment. The magnitude of angle $\theta_1$ depends in one embodiment on various factors, including the size of the catheter and/or needle to be inserted into the port conduit, the size of the conduit itself, etc.

The conduit 18 then extends to and through a cavity 20A defined by a valve housing 20 of the port body. The conduit 18 extends to a distal open end of the stem 24 of the port 10. The conduit 18 is sized so as to enable the catheter 40 (FIG. 2) to pass therethrough, as will be seen.

As mentioned, the valve housing 20 defines a cavity 20A through which the conduit passes and which houses a valve/seal assembly 22. The valve/seal assembly 22 includes a sealing element, or seal 32, which defines a central hole through which the catheter 40 can pass, a first slit valve 34A and a second slit valve 34B. The seal 32 and valves 34A, 34B are sandwiched together in one embodiment and secured in place within the cavity 20A as shown in FIG. 1E. The slits of the slit valves 34A, 34B are rotationally offset from one another by about 90 degrees in the present embodiment, though other relationships are possible.

The seal 32 and valves 34A, 34B of the valve/seal assembly 22 cooperate to enable fluid-tight passage therethrough of the catheter 40 (FIG. 2) while also preventing backflow of fluid through the valve/seal assembly. Indeed, in one embodiment the seals disclosed herein prevent fluid flow around the external portion of the catheter when the catheter is disposed through the seal, while the valves are suitable for preventing fluid flow when no catheter passes through them. As such, when the catheter 40 is not inserted therethrough the valve/seal assembly 22 seals to prevent passage of air or fluid. In the present embodiment, the seal 32 and valves 34A, 34B include silicone, though other suitably compliant materials can be employed.

The port 10 in the present embodiment includes an overmolded portion 36 that covers the port body 12. The overmolded portion 36 includes silicone or other suitably compliant material and surrounds the body 12 as shown so as to provide a relatively soft surface for the port 10 and reduce patient discomfort after port implantation. The overmolded portion 36 includes two predetermined suture locations 38, best seen in FIG. 1C, for suturing the port 10 to patient tissue, though sutures may be passed through other portions of the overmolded portion, if desired. The overmolded portion 36 further defines a relatively flat bottom surface 36A so as to provide a stable surface for the port 10 in its position within the tissue pocket after implantation. In contrast, the port shown in FIG. 3C includes a bottom surface with a slightly rounded profile.

FIG. 2 depicts details regarding the insertion of the catheter 40 disposed on the needle 42, according to one embodiment. After locating the port 10 via through-skin palpation of the palpation features 26, a clinician uses the catheter-bearing needle 42 to pierce a skin surface 44 and insert the needle until a distal tip 42A thereof impinges on a portion of the receiving cup 14, as shown. Note that, because of the orientation of the receiving cup 14 as substantially parallel to the skin surface, the needle 42 can impinge on the receiving cup at an insertion angle $\theta_2$ that is relatively steep, which facilitates ease of needle insertion into the body. Indeed, in one embodiment a needle inserted substantially orthogonally through the skin of the patient can impinge the receiving cup of the access port.

The needle 42 is manipulated until the distal tip 42A is received into the guide groove 28, which will enable the distal tip to be guided along the groove to the inlet port 16. The needle 42 is then inserted through the inlet port 16 and into the first portion 18A of the conduit 18 until it is stopped by the bend 30. The needle 42 can then be proximally backed out a small distance, and the catheter 40 advanced over the needle such that the catheter bends and advances past the bend 30 into the second portion 18B of the conduit 18. Catheter advancement continues such that a distal end 40A of the catheter 40 advances into and past the hole of the seal 32 and through both slits of the slit valves 34A, 34B of the valve/seal assembly 40. Once the distal end 40A of the catheter 40 has extended distally past the valve/seal assembly 22, further advancement can cease and fluid transfer through the catheter 40 and port 10 can commence, including infusion and/or aspiration through the stem 24. Once fluid transfer is completed, the catheter 40 can be withdrawn proximally through the valve/seal assembly 22 and the conduit, then withdrawn through the surface 44 of the skin and out of the patient.

Figure 3A:
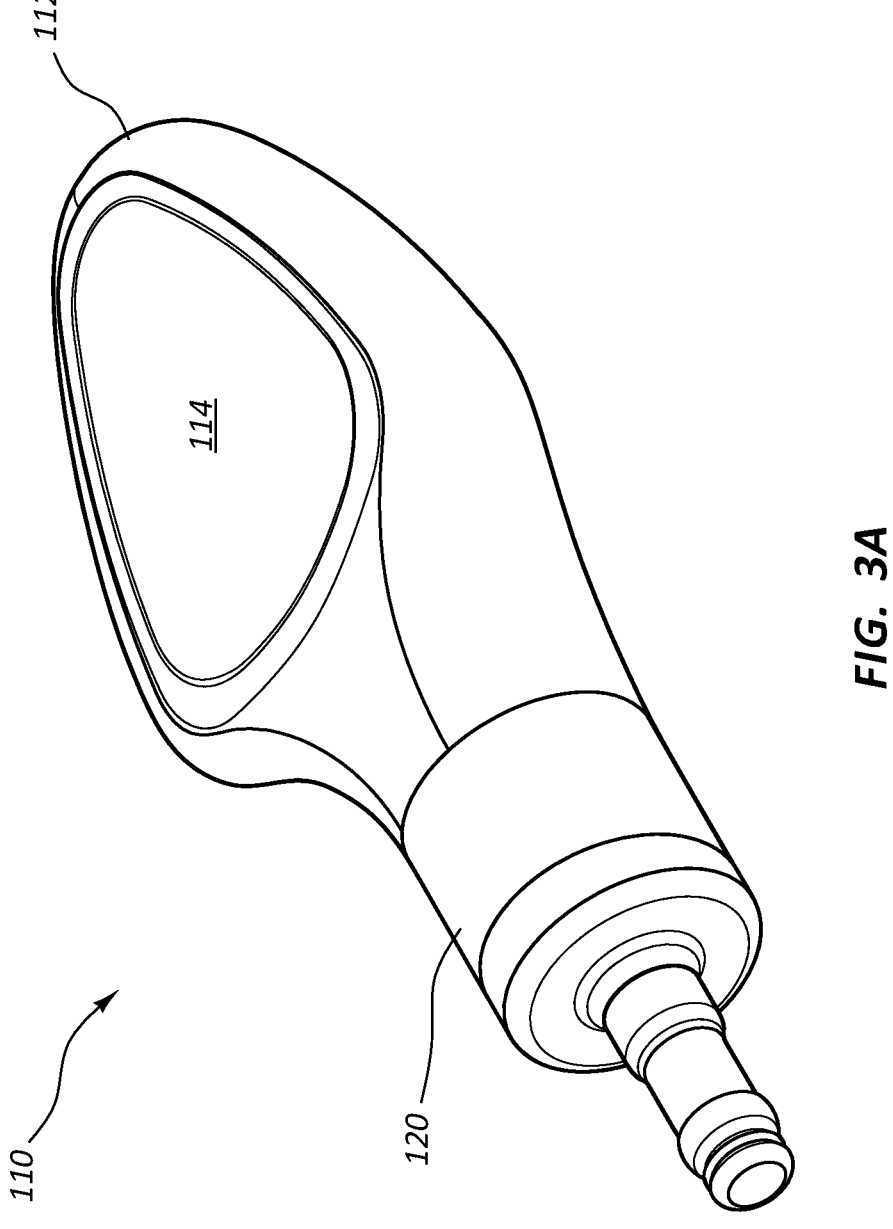
FIGS. 3A-3C are various views of a low-profile access port according to one embodiment.
Figure 3B:
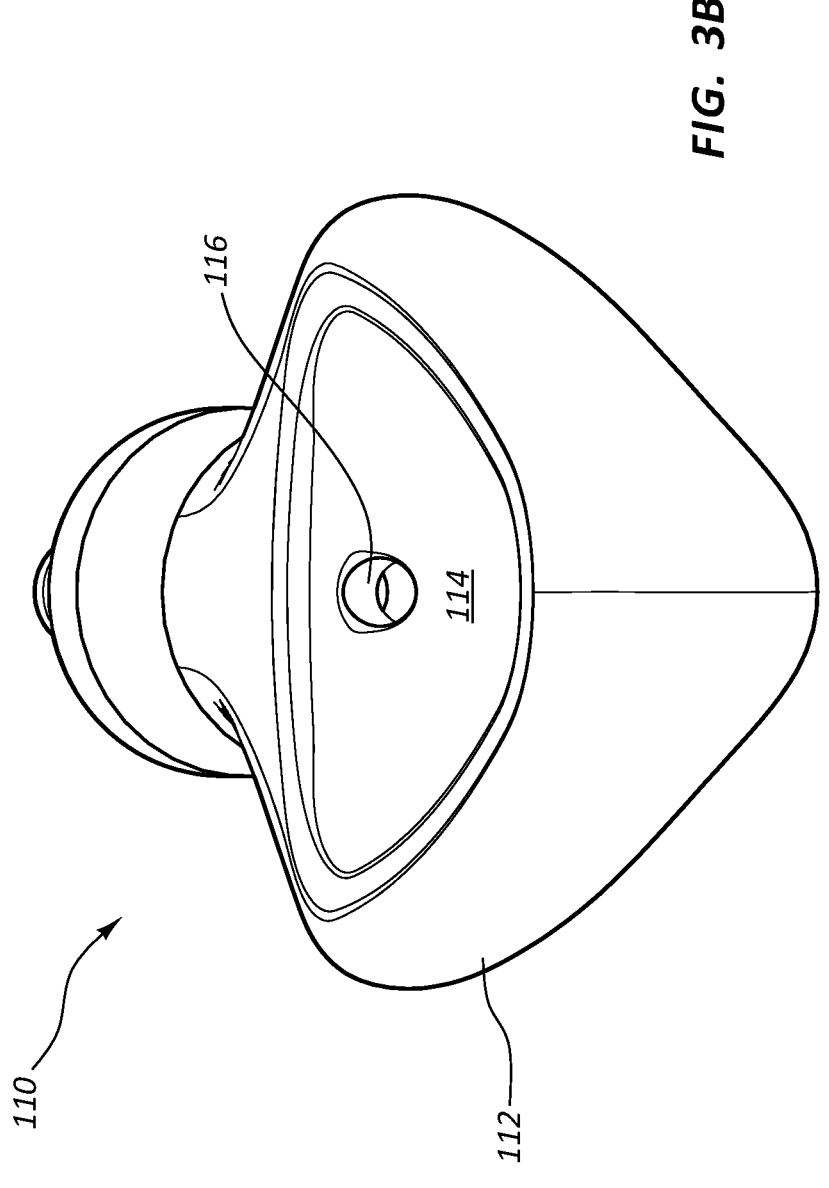
Figure 3C:
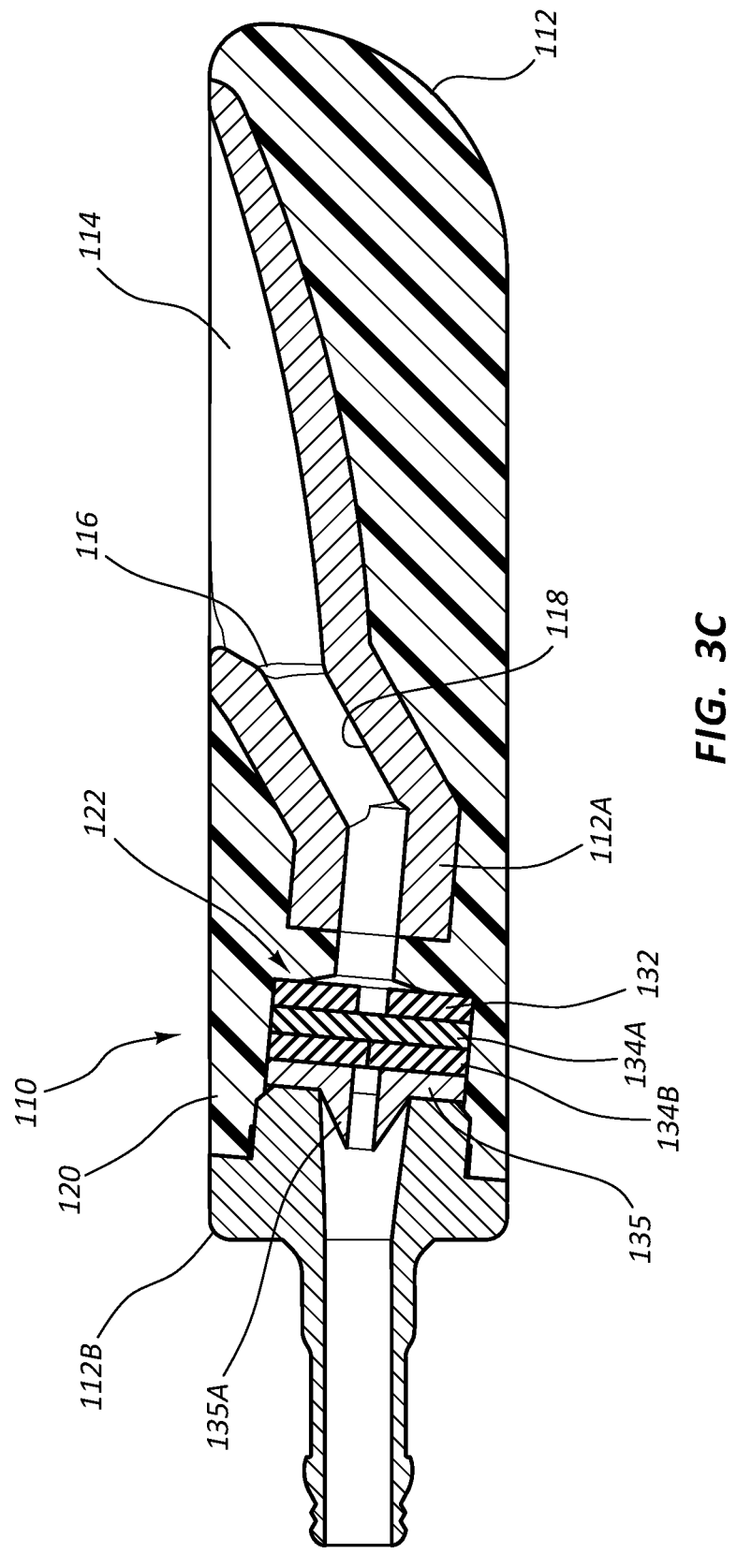

FIGS. 3A-3C depict details of an access port 110 according to another embodiment. Note that various similarities exist between the port 10 and the other ports shown and described herein. As such, only selected port aspects are discussed below. As shown, the port 110 includes a body 112 that in turn includes a first body portion 112A and a second body portion 112B, best seen in FIG. 3C. The body 112 in the present embodiment includes a thermoplastic, such as an acetyl resin in the present embodiment. As such, the first and second body portions 112A, 112B are ultrasonically welded to one another to define the body 12, in the present embodiment. As before, a receiving cup 114 is included with the body 112 and is operably connected to a conduit 118 via an inlet port 116. Also, note that a variety of materials can be used to define the port body, receiving cup, conduit, etc.

A valve/seal assembly 122 is disposed within a cavity 120A that is defined by a valve housing 120, which in the present embodiment, is defined by the first body portion 112A. The valve/seal assembly 122 includes a proximal seal 132 with a central hole for catheter passage, two slit valves 134A, 134B each with a slit arranged at a 90-degree offset with respect to the other, and a distal seal 135 with a central hole, also referred to herein as a sphincter seal.

The distal seal 135 includes on its distal surface a frustoconical portion 135A disposed about the seal central hole that is configured to provide a sphincter-like seal about the outer surface of a catheter when it extends through the valve/seal assembly. The frustoconical portion 135A is disposed such that any back-flowing fluid impinging on the frustoconical portion will cause the seal to secure itself about the outer surface of the catheter in an even tighter engagement, thus preventing backflow past the catheter outer surface when high fluid pressures are present, such as in the case of power injection. As mentioned, other valve/seal combinations can also be included in the valve/seal assembly.

In the present embodiment, the receiving cup 114 and portion of the conduit 118 proximal to the valve/seal assembly 122 both include a needle-impenetrable lining that prevents the distal end of a needle from gouging the surface when impinging thereon. This, in turn, prevents the undesirable creation of material flecks dug by the needle. Various suitable materials can be employed for the needle-impenetrable material, including glass, ceramic, metals, etc. In one embodiment, the components of the port 110 are all nonmetallic such that the port is considered MRI-safe, by which the port does not produce undesired artifacts in MRI images taken of the patient when the port is in implanted therewithin.

Figure 4:
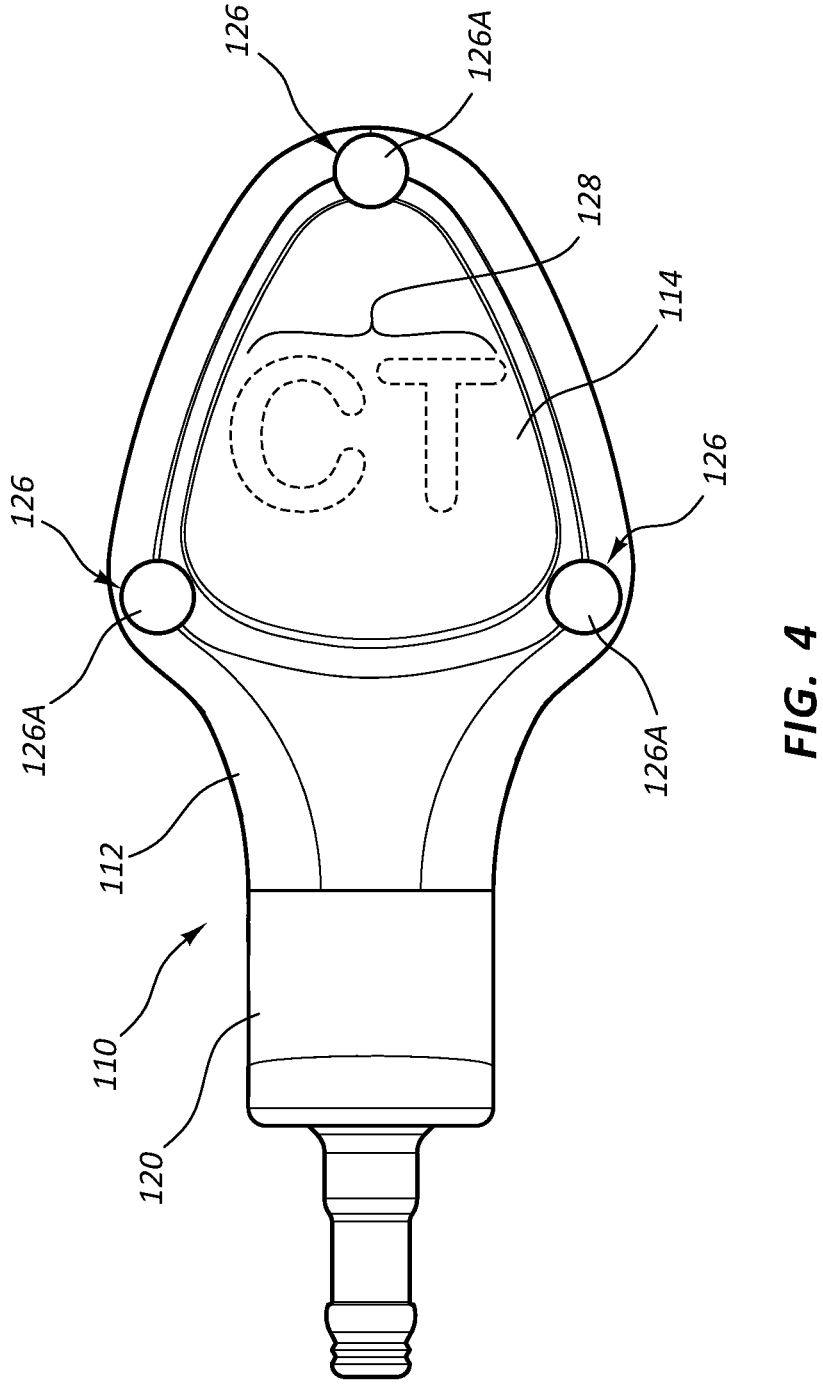
FIG. 4 is a top view of a low-profile access port according to one embodiment.

FIG. 4 depicts additional features of the port 110 according to another embodiment. As shown, in the present embodiment the receiving cup 18 includes radiopaque indicia 128 to indicate a characteristic of the port 110. Here, the radiopaque indicia 128 includes a "C" and a "T" that are formed by a radiopaque material, such as tungsten, bismuth trioxide, etc., so as to be visible after port implantation via x-ray imaging technology. For instance, the radiopaque material can be formed as an insert that is insert-molded included in the port body, as an initially flowable material that is injected into a cavity of the port body before hardening, etc. In embodiments where the port body is metallic, the radiopaque indicia can be formed by etching, engraving, or otherwise producing a relative thickness difference between the indicia and the surrounding port body material so as to produce an x-ray-discernible contrast that shows up in an x-ray image.

In the present embodiment, the CT radiopaque indicia 128 indicate to an observer that the port is capable of power injection of fluids therethrough. In addition to this characteristic, other characteristics can be indicated by various other types of indicia as appreciated by one skilled in the art.

Further, in the present embodiment the top view of the port 110 of FIG. 4 indicates that the port body 112 in the region surrounding the receiving cup 114 defines a generally triangular shape, which can be palpated by a clinician after implantation and can indicate not only the location of the receiving cup, but also a particular characteristic of the port, such as its ability to be used for power injection. Of course, the receiving cup may define shapes other than triangular in other embodiments.

FIG. 4 further shows that distributed about the perimeter of the receiving cup 114 are three palpation features 126, namely, three suture plugs 126A disposed in corresponding holes defined in the port body 112. The suture plugs 126A include raised silicone bumps in the present embodiment and can serve to locate the position of the receiving cup 114 post-implantation when they are palpated by a clinician prior to needle insertion into the patient. Various other palpation features could be included with the port, in other embodiments.

Figure 5:
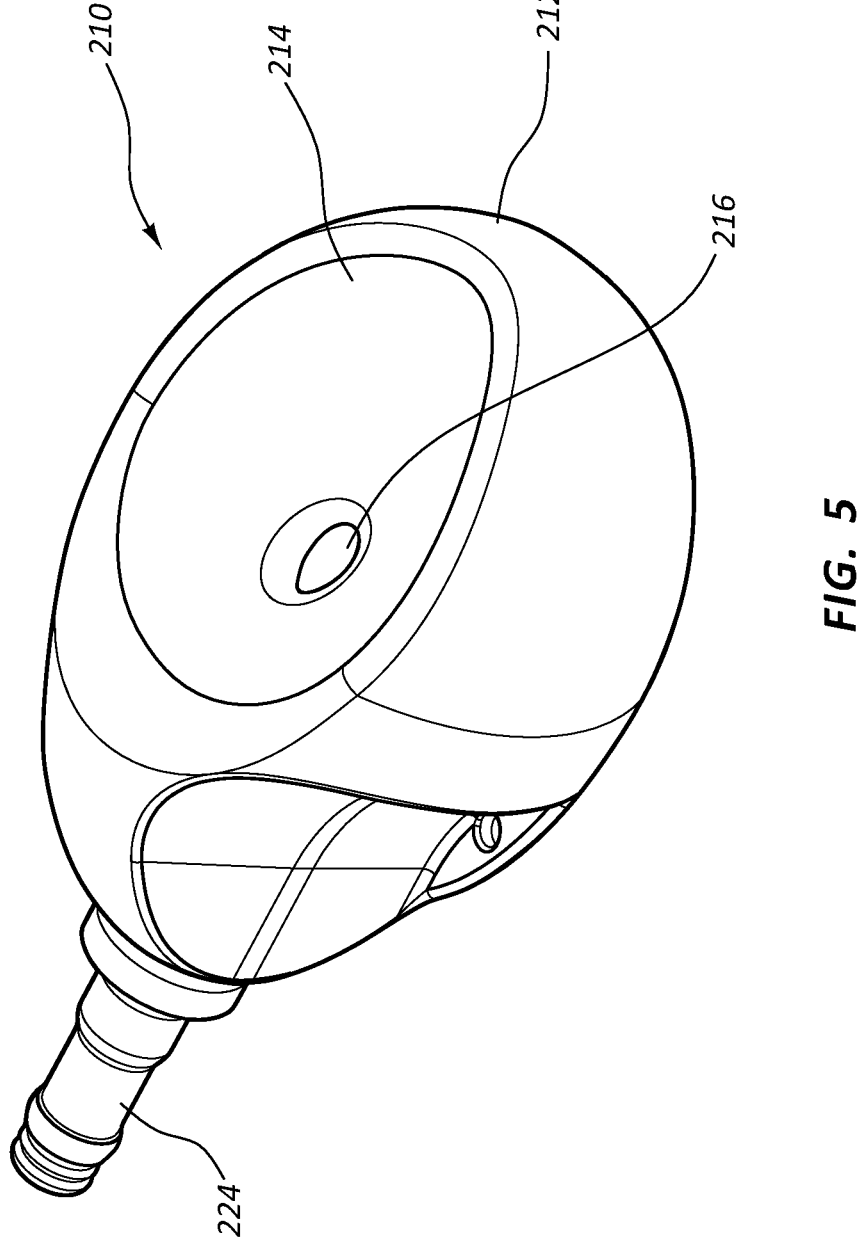
FIG. 5 is a perspective view of a low-profile access port according to one embodiment.

FIG. 5 depicts details of a low-profile port 210 according to one embodiment, including a body 212 defining a concavely-shaped receiving cup 214 and an inlet port 216 positioned slightly off-center with respect to the receiving cup. A stem 224 is included as a fluid outlet.

Figure 6:
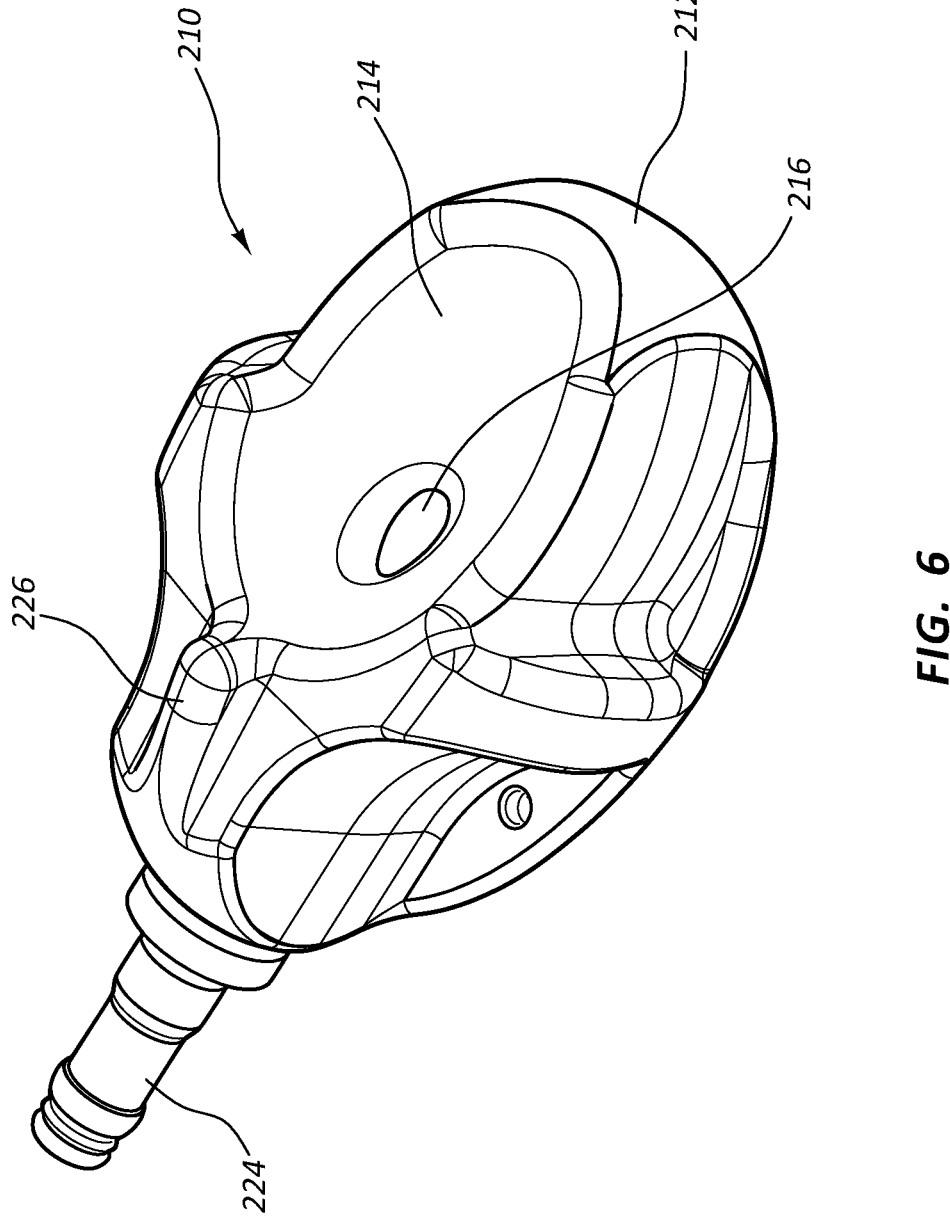
FIG. 6 is a perspective view of a low-profile access port according to one embodiment.

FIG. 6 depicts the low-profile port 210 according to another embodiment, wherein the body 212 defining additional surface features, including a raised palpation feature 226 distal to the receiving cup 214. In light of FIGS. 5 and 6, it is thus appreciated that the port can be configured in a variety of shapes and configurations to provide a low-profile solution for providing vascular access. Note also that the receiving cup shape, design, and configuration can vary from is explicitly shown and described herein.

Figure 7A:
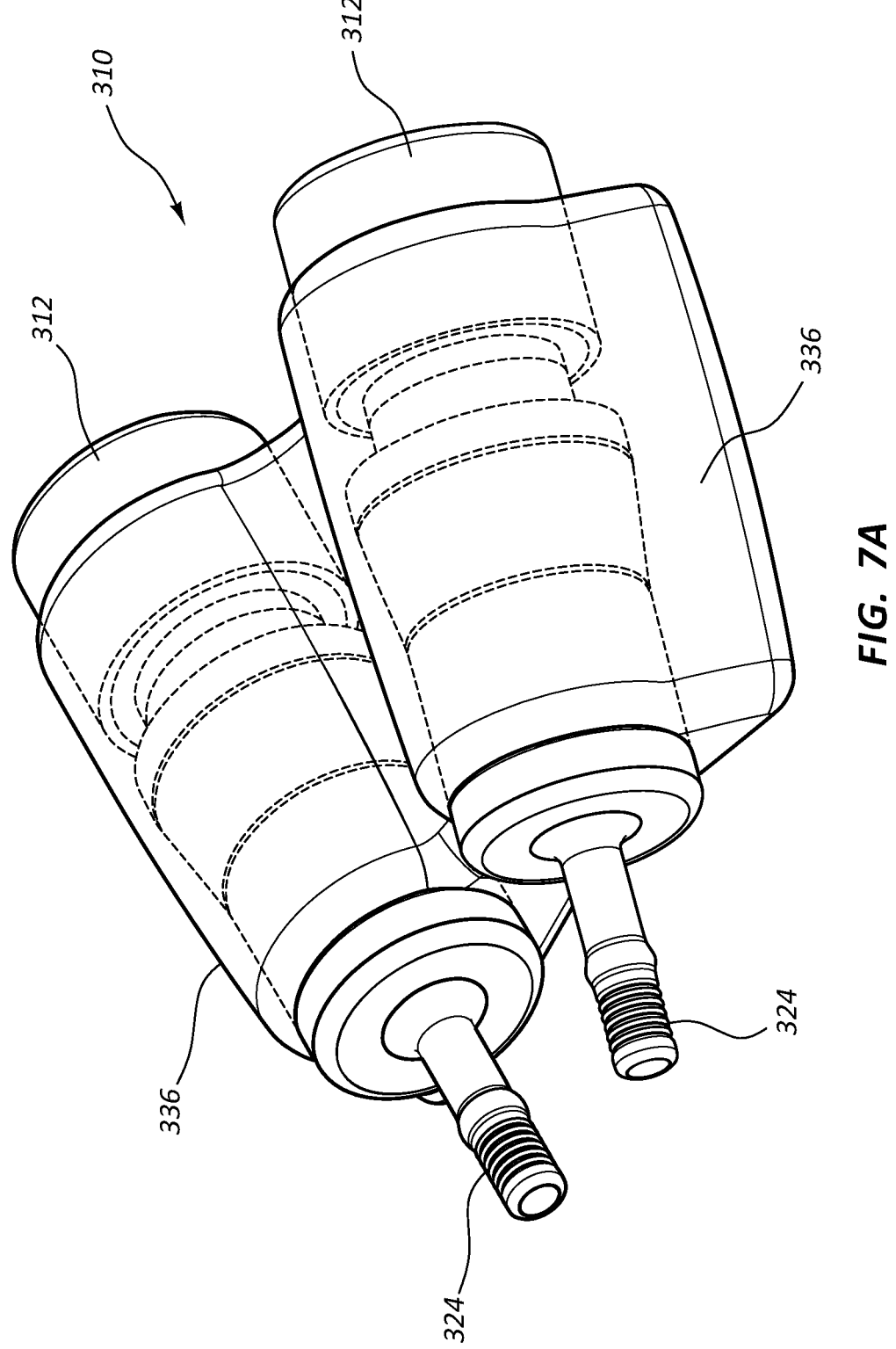
FIGS. 7A and 7B are various views of an access port according to one embodiment.
Figure 7B:
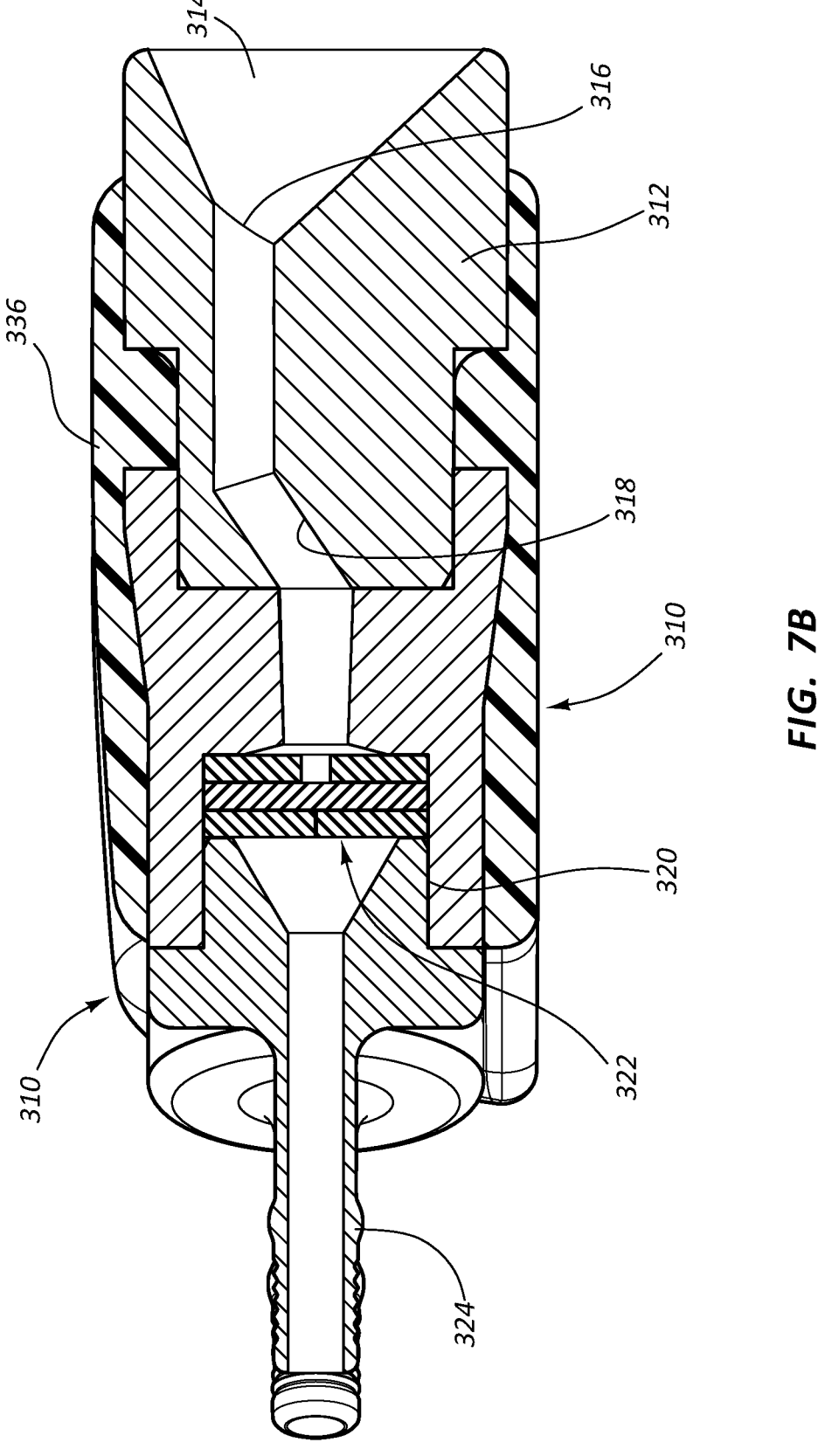

FIGS. 7A and 7B depict various details of a low-profile dual-body access port 310 according to one embodiment, wherein each of the port bodies 312 defines a receiving cup 314 that is laterally facing and includes an inlet port 316 leading to a conduit 318. The conduit 318 extends distally to a valve/seal assembly 322 disposed in a valve housing 320, which in the present embodiment, is defined by a portion of the body 312. The conduit 318 extends through the port 324. A compliant overmolded portion 324 covers portions of each body 312 of the port 310 and operably joins the bodies to one another. The bodies 312 can include any suitable material, including metal, thermoplastic, etc.

Figure 8A:
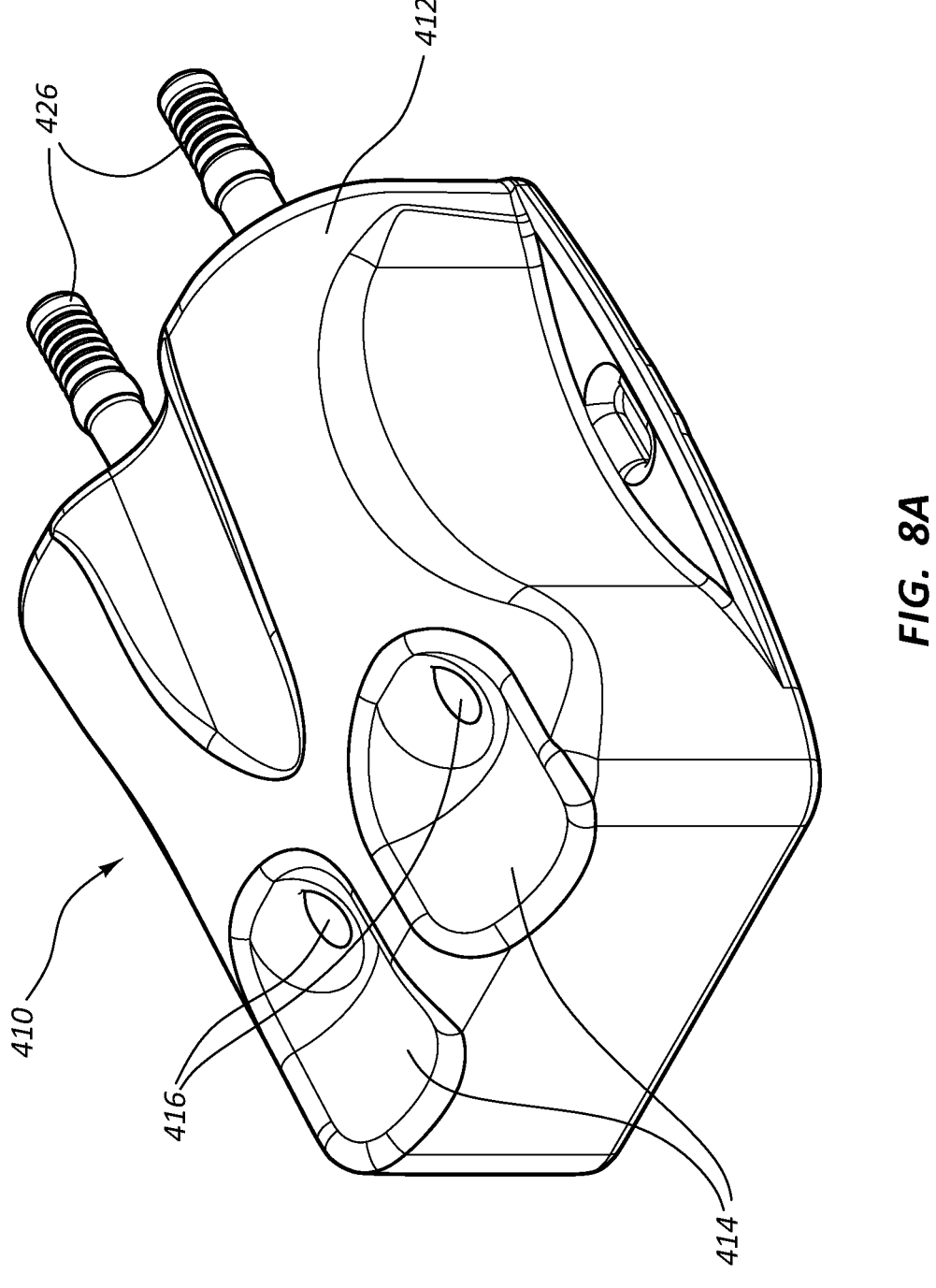
FIGS. 8A and 8B are various views of an access port according to one embodiment.
Figure 8B:
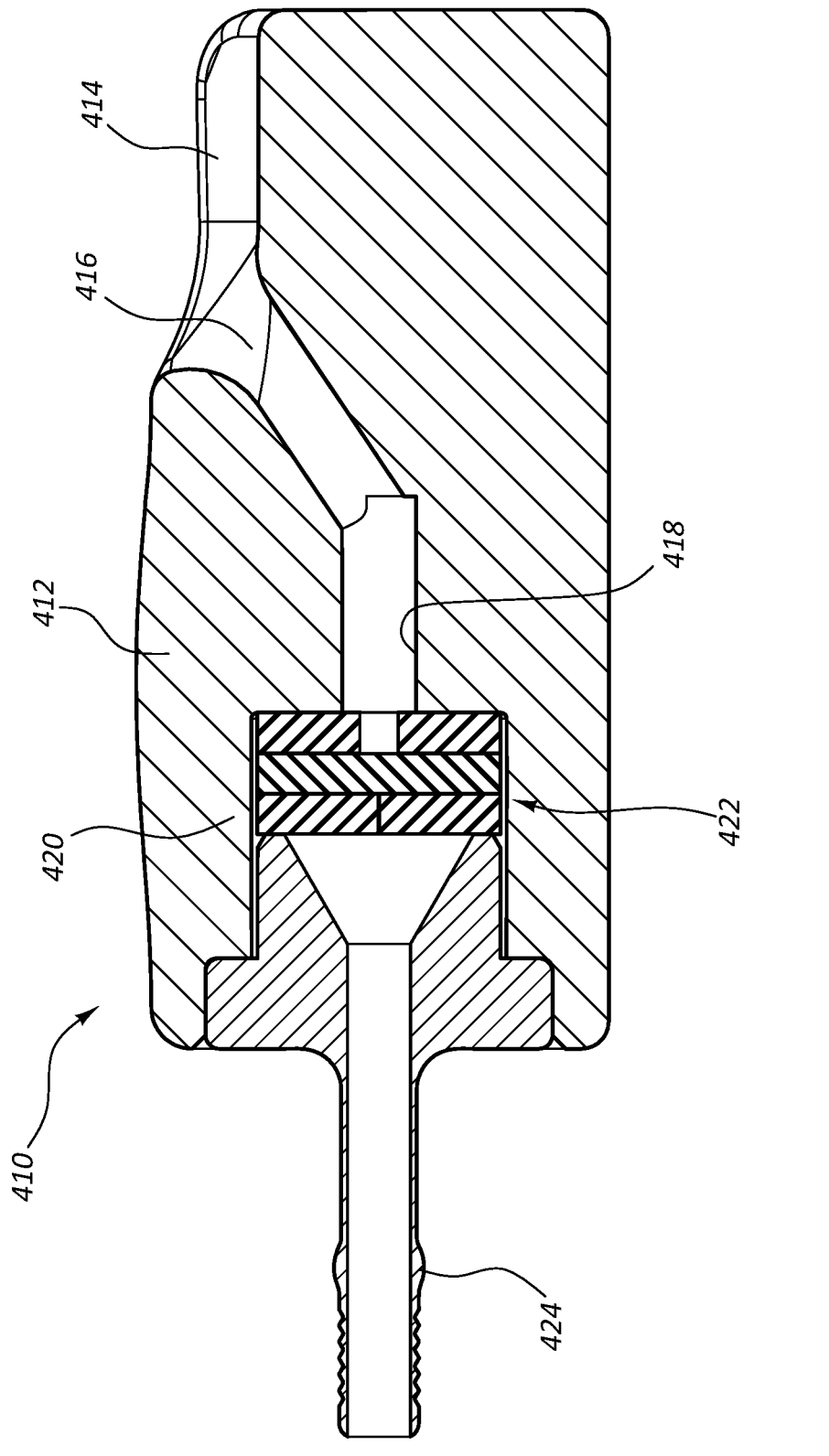

FIGS. 8A and 8B depict various details of a low-profile dual-body access port 410 according to one embodiment, wherein a port body 412 defines dual fluid paths. Each fluid path includes a receiving cup 414 defined by the body 412 and facing a substantially upward orientation from the perspective shown in FIGS. 8A and 8B. An inlet port 416 is included with each receiving cup 414 and defines the opening to a conduit 418. Each conduit 418 extends distally to a valve/seal assembly 422 disposed in a valve housing 420, which in the present embodiment, is defined by a portion of the body 412. The conduit 418 extends through the port 424. The body 412 can include any suitable material, including metal, thermoplastic, etc.

Reference is now made to FIGS. 9A-30, which depict various details of embodiments generally directed to vascular access devices, also referred to herein as access ports, for subcutaneous implantation within the body of a patient. The implanted access ports to be described are transcutaneously accessible by a catheter-bearing needle, such as a peripheral intravenous ("PIV") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter.

In accordance with one embodiment, the access port defines a relatively low profile so as to facilitate ease of placement within the subcutaneous tissue of the patient. Further, the access port is configured to provide a relatively large subcutaneous target to enable the PIV catheter or other suitable catheter-bearing needle to access the port without difficulty. In addition, the access port includes a valve/seal assembly to permit power injection of fluids through the access port. As before, possible applications for the access port described herein include administration of medicaments and other fluids to the patient, pheresis/apheresis, fluid aspiration, etc.

Figure 9A:
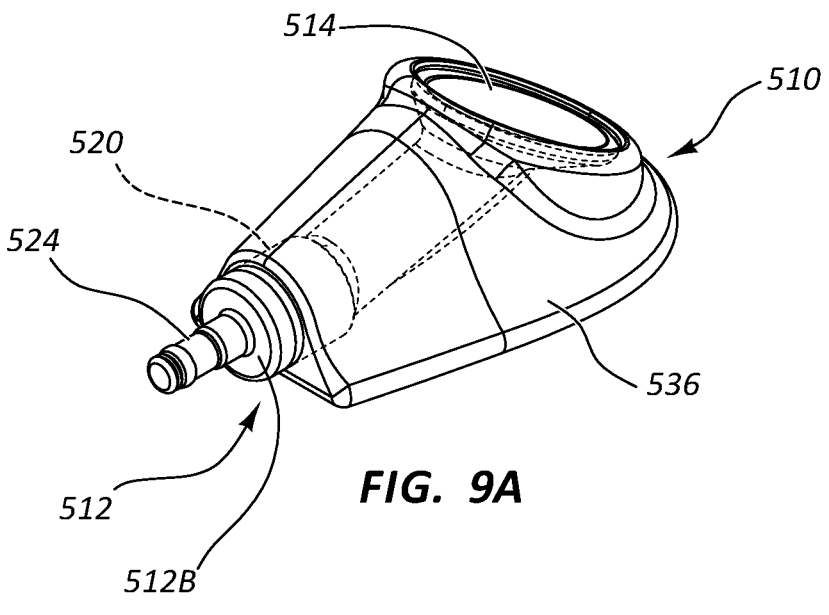

Reference is first made to FIGS. 9A-9G, which show various details of a vascular access device (also "access port" or "port"), generally designated at 510, in accordance with one embodiment. As shown, the port 510 includes a body 512 that is defined in the present embodiment by a first portion 512A and a second portion 512B (FIG. 9E). In the present embodiment the port body 512 includes a metal such as titanium, and as such, the second portion 512B is press fit into engagement with the first portion 512A to define the body, though it is appreciated that the port body can include a variety of other materials, including metals, thermoplastics, ceramics, etc.

Figure 9B:
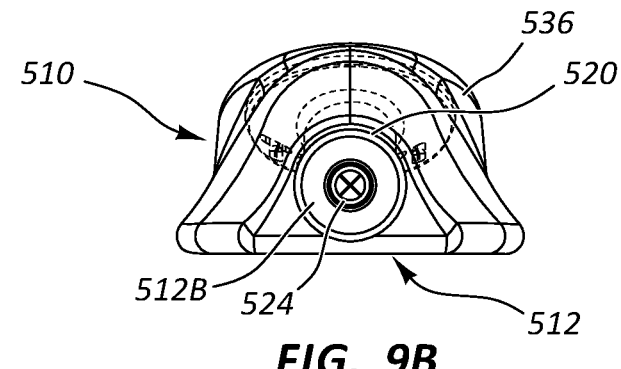
Figure 9C:
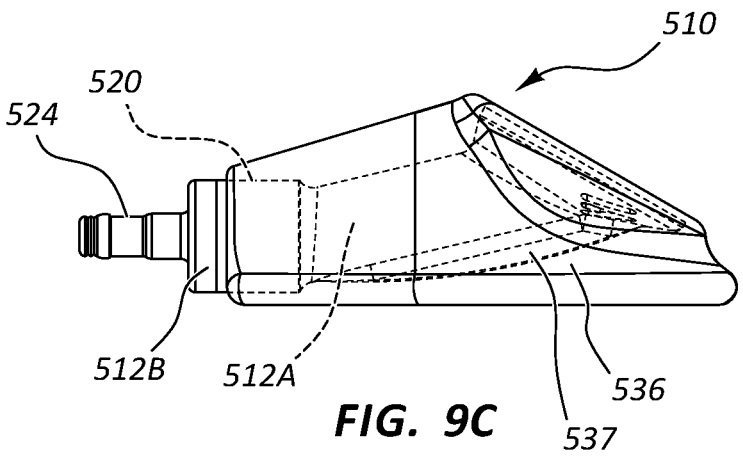

The port body first portion 512A defines in the present embodiment a substantially funnel-shaped receiving cup 514 for receiving and directing a catheter-bearing needle (FIG. 14A) to operably connect with the port 510, as described further below. In particular, the substantially funnel shape of the receiving cup 514 is configured to direct the catheter-bearing needle (FIG. 14A) impinging thereon toward an inlet port 516 that serves as an opening for a conduit 518 defined by the port body 512. The open and shallow nature of the receiving cup 514, angled toward the skin surface of the patient enables the receiving cup to present a large, easily accessible target for the needle when introduced into the skin, as seen in FIGS. 14A-14D. FIGS. 9B and 9C further show that the port 510 defines a relatively low profile height, which enables relatively shorter needle lengths to be used for accessing the port after implantation. Note that palpation features can be included with the port body 512 to assist a clinician to locate and/or identify the port 510 via finger palpation after implantation under the skin of the patient, as with other embodiments herein. Further, in another embodiment a guide groove can be defined on the receiving cup 514 to be longitudinally aligned with the inlet port 516 of the conduit 518, similar to that shown in the access port 10 of FIG. 1A

Figure 10:
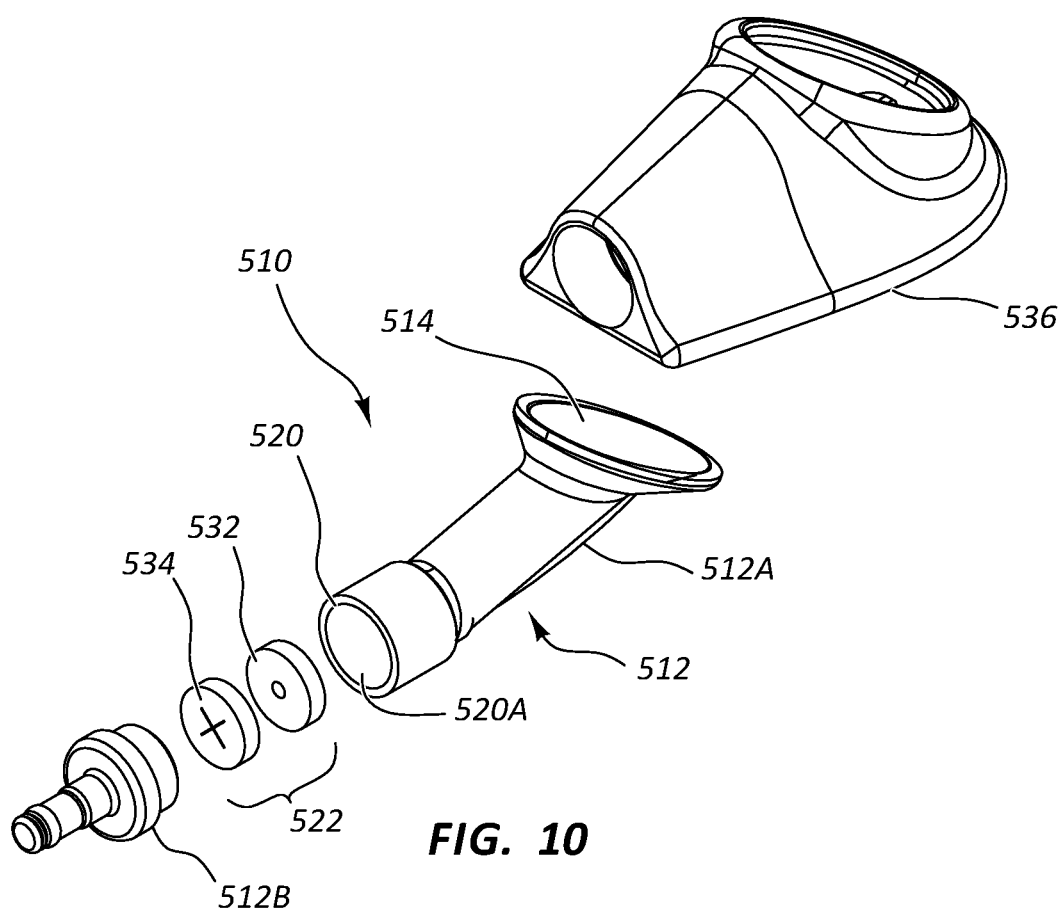
FIG. 10 is an exploded view of the access device of FIGS. 9A-9G.
Figure 11:
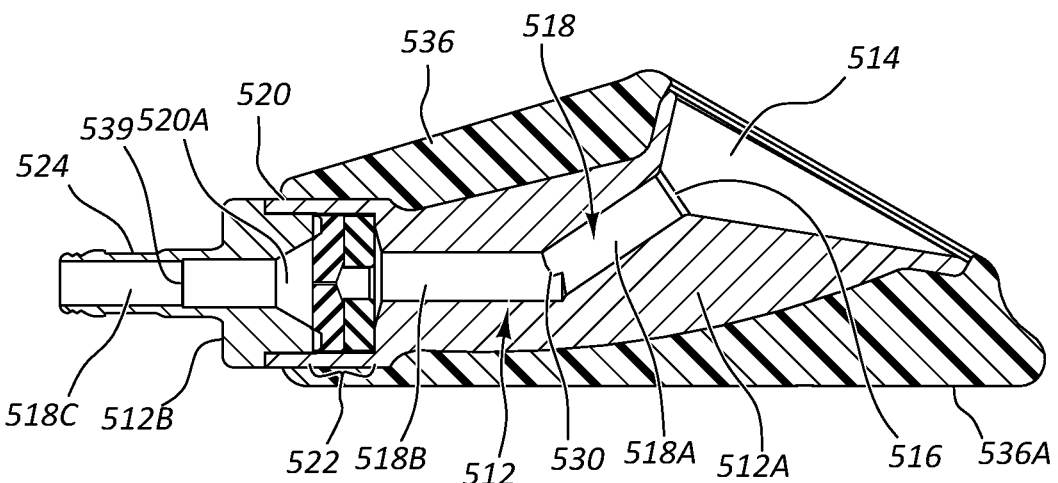
FIG. 11 is a cross-sectional view of the access device of FIGS. 9A-9G.
Figure 12A:
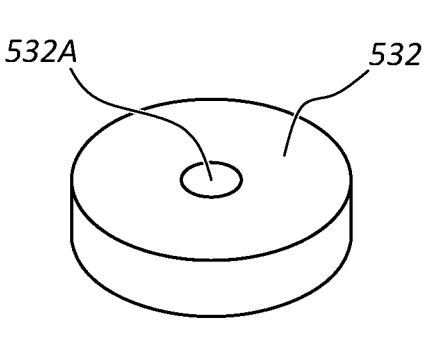
FIGS. 12A-12C depict various views of a seal according to one embodiment.
Figure 12B:
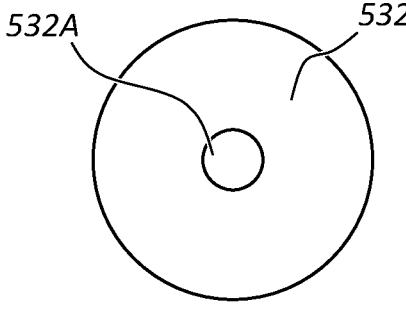
Figure 12C:
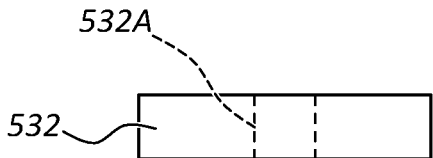

Together with FIGS. 9A-9G, reference is also made to FIGS. 10 and 11. As best seen in FIG. 11, the port body 512 further defines the conduit 518 as a pathway into which a transcutaneously inserted catheter can pass so as to place the catheter in fluid communication with the port 510 and the indwelling catheter attached to the stem 524 thereof. As shown, the conduit 518 is in fluid communication with the receiving cup 514 via the inlet port 516. A first conduit portion 518A of the conduit 518 distally extends from the inlet port 516 in an angled downward direction from the perspective shown in FIG. 11 to a bend 530, where a second conduit portion 518B of the conduit extends substantially horizontally (from the perspective shown in FIG. 11) at a predetermined angle with respect to the first conduit portion. Note that predetermined angle at the bend 530 in one embodiment is about 34 degrees, but can vary from this in other embodiments, including angles less or more than 34 degrees in one embodiment. The magnitude of the predetermined angle at the bend 530 depends in one embodiment on various factors, including the size of the catheter and/or needle to be inserted into the port conduit, the size of the conduit itself, etc.

The conduit 518 then extends to and through a cavity 520A defined by a valve housing 520 of the port body 12 where a third conduit portion 518C extends to a distal open end of the stem 524 of the port 510. In the present embodiment the conduit 518 is sized so as to enable the catheter 40 (FIG. 14A) to pass therethrough to a predetermined point, as will be seen.

Figure 13A:
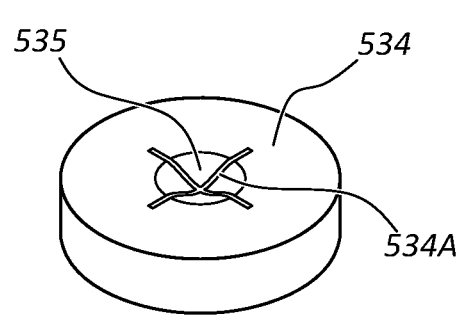
FIGS. 13A-13C depict various views of a valve according to one embodiment.
Figure 13B:
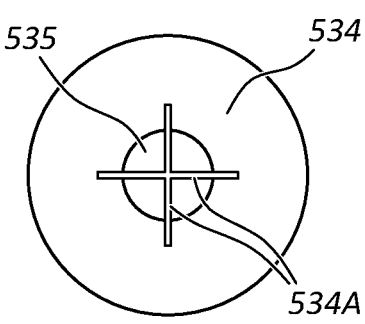
Figure 13C:
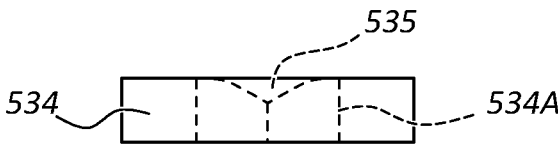

As mentioned, the valve housing 520, defined by portions of the first and second portions 512A, 512B of the body 512 defines a cavity 520A through which the conduit 518 passes and which houses a valve/seal assembly 522. The valve/seal assembly 522 includes a sealing element, or seal 532, which defines a central hole 532A (FIGS. 12A-12C) through which the catheter 40 (FIG. 14A) can pass, and a slit valve 534 including two intersecting slits 534A (FIGS. 13A-13C). The seal 532 and valve 534 are sandwiched together in one embodiment, with the seal 532 disposed proximal to the valve 534, and secured in place within the cavity 520A as shown in FIG. 11. The slits 534A of the slit valve 534 are orthogonally offset from one another by about 90 degrees in the present embodiment, though other relationships are possible. Note that the valve 534 includes a central depression 535 to ease the transition of passage of the catheter 40 from the seal 532 to the valve.

The seal 532 and valve 534 of the valve/seal assembly 522 cooperate to enable fluid-tight passage therethrough of the catheter 40 (FIG. 14A) while also preventing backflow of fluid through the valve/seal assembly. Indeed, in one embodiment the seals disclosed herein prevent fluid flow around the external portion of the catheter when the catheter is disposed through the seal 532, while the valve 534 is suitable for preventing fluid flow when no catheter passes through them. As such, when the catheter 40 is not inserted therethrough the valve/seal assembly 522 seals to prevent passage of air or fluid through the conduit 518. In the present embodiment, the seal 532 and valve 534 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 532 and valve 534 to enhance lubricity and extend component life. In another embodiment, the silicone oil is infused into the silicone.

The port 510 in the present embodiment includes an overmolded portion 536 that covers a majority portion of the port body 512. The overmolded portion 536 includes silicone, such as SILASTIC® Q7-4850 liquid silicone rubber or other suitably compliant material and surrounds the body 512 as shown so as to provide a relatively soft surface for the port 510 and reduce patient discomfort after port implantation within the patient body. The overmolded portion 536 includes in one embodiment predetermined suture locations 538, best seen in FIG. 9F, for suturing the port 510 to patient tissue, though sutures may be passed through other portions of the overmolded portion, if desired. The overmolded portion 536 further defines a relatively flat bottom surface 536A so as to provide a stable surface for the port 510 in its position within the tissue pocket after implantation into the patient body.

FIGS. 9C and 9G show that the first body portion 512A defines a securement ridge 537 that serves as an anchor to prevent relative movement between the overmolded portion 536 and the body 512. The securement ridge 537 can vary in shape, number, configuration, etc. Note that the overmolded portion 536 in one embodiment is molded in a molding process over the body 512. In another embodiment, the overmolded portion 536 is separately formed then adhesively attached to the body 512, such as via Med A adhesive. These and other configurations are therefore contemplated.

Figure 14A:
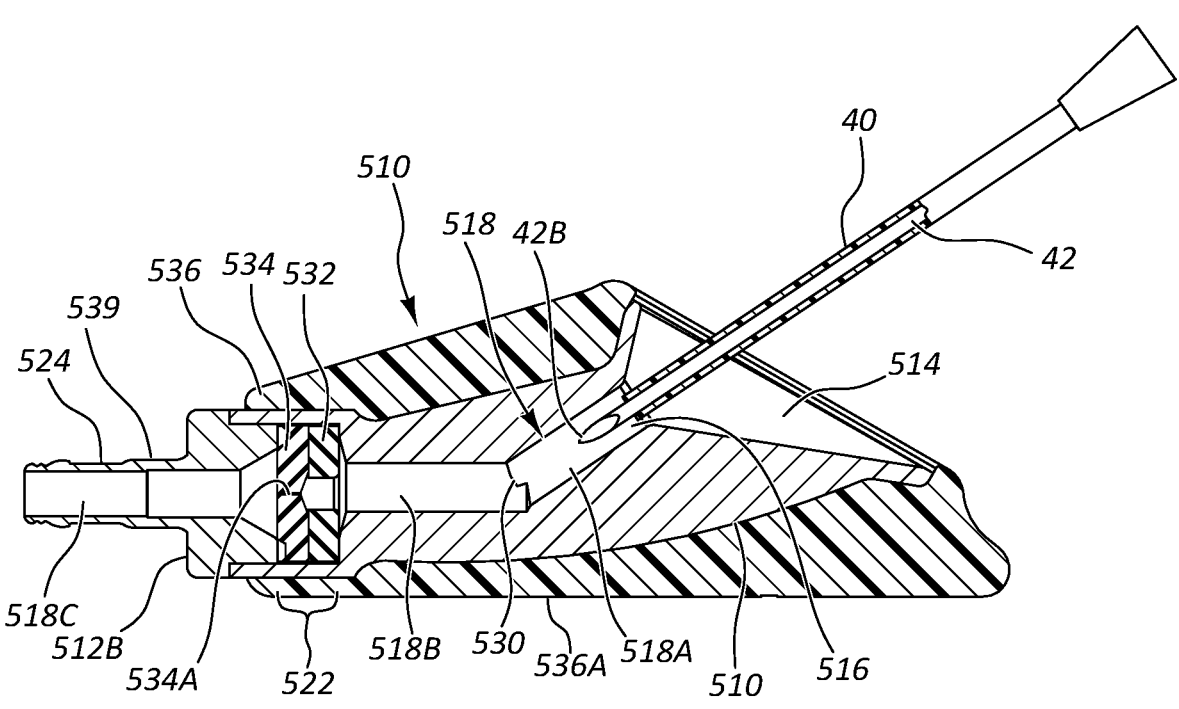
FIGS. 14A-14D depict various stages of insertion of a catheter into the access device of FIGS. 9A-9G.

FIGS. 14A-14D depict details regarding the insertion of the catheter 40 disposed on the needle 42 into the port 510 (already subcutaneously implanted into the body of the patient), according to one embodiment. After locating the port 510 (optionally via through-skin palpation of palpation features, such as a top portion of the overmolded portion 536 and/or the receiving cup 514), a clinician uses the catheter-bearing needle 42 to pierce a skin surface and insert the needle until a distal tip 42B thereof impinges on a portion of the receiving cup 514, as shown in FIG. 14A. Note that, because of the orientation of the receiving cup 514 is angled substantially toward the skin surface, the needle 42 can impinge on the receiving cup at an insertion angle that is relatively steep, which facilitates ease of needle insertion into the body. Indeed, in one embodiment a needle inserted substantially orthogonally through the skin of the patient can impinge the receiving cup of the access port. In another embodiment, the insertion angle of the needle 42 can be relatively shallow, similar to current insertion angles for IV catheters.

Figure 14B:
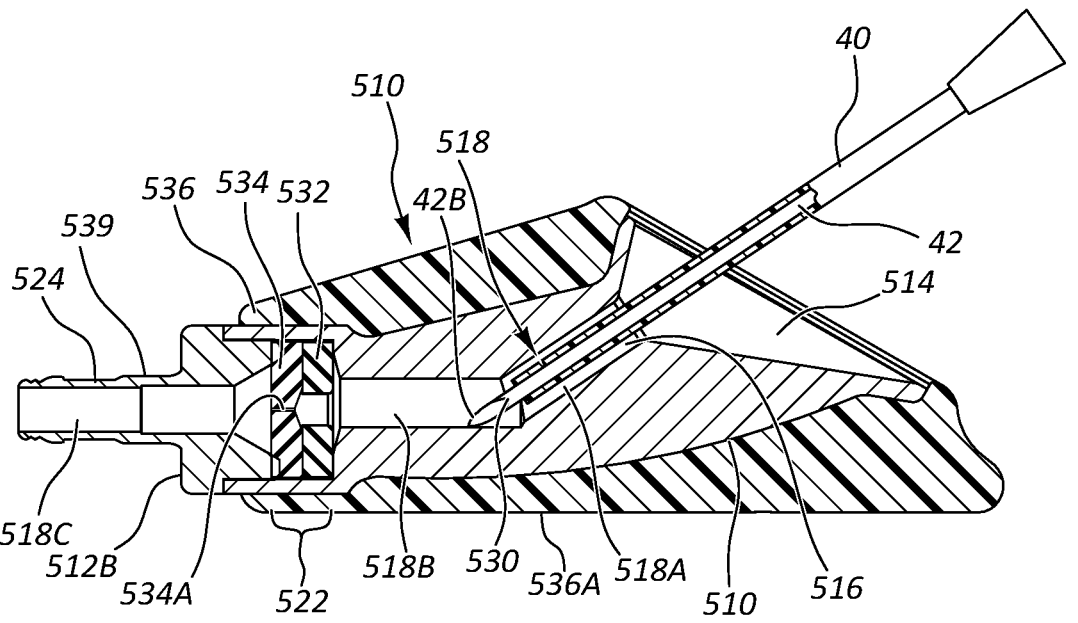
Figure 14C:
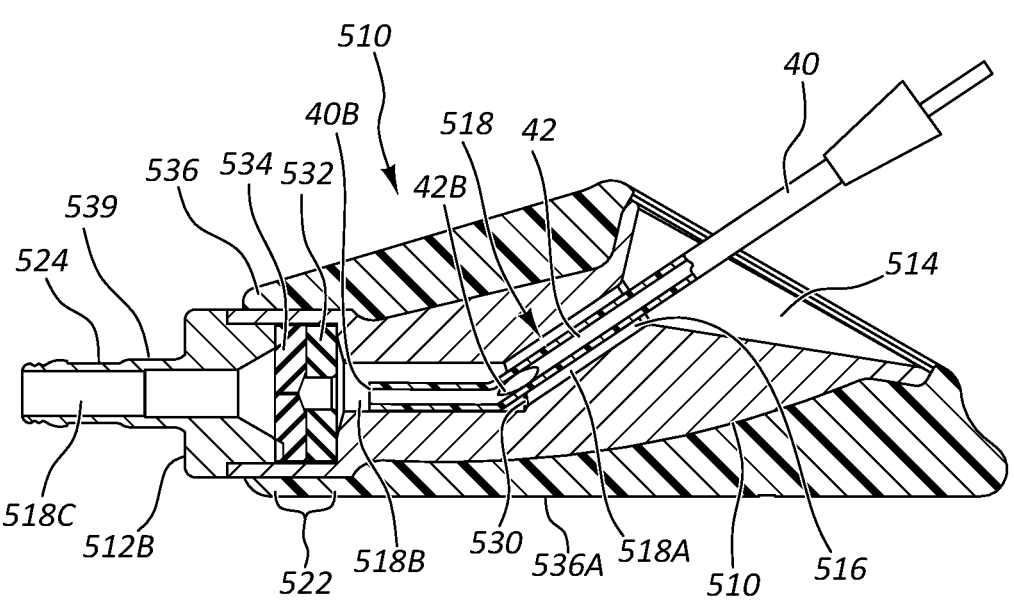

The needle 42 is manipulated by the clinician and guided by impingement on the receiving cup 514 until the needle distal tip 42B is guided to the inlet port 516. The needle 42 is then inserted through the inlet port 516 and into the first portion 518A of the conduit 518 until it is stopped by the bend 530, as seen in FIG. 14B. The needle 42 can then be proximally backed out a small distance, and the catheter 40 advanced over the needle such that the catheter bends and advances past the bend 530 into the second portion 518B of the conduit 518, as seen in FIG. 14C. Catheter advancement continues such that a distal end 40B of the catheter 40 advances into and past the hole 532A of the seal 532 and through both slits 534A of the slit valve 534 of the valve/seal assembly 522. Note that the length of the second conduit portion 518B is sufficient to enable the cross-sectional shape of the distal portion of the catheter 40 to return to a substantially round shape from the oval shape imposed thereon as a result of its passage through the conduit bend 530.

Figure 14D:
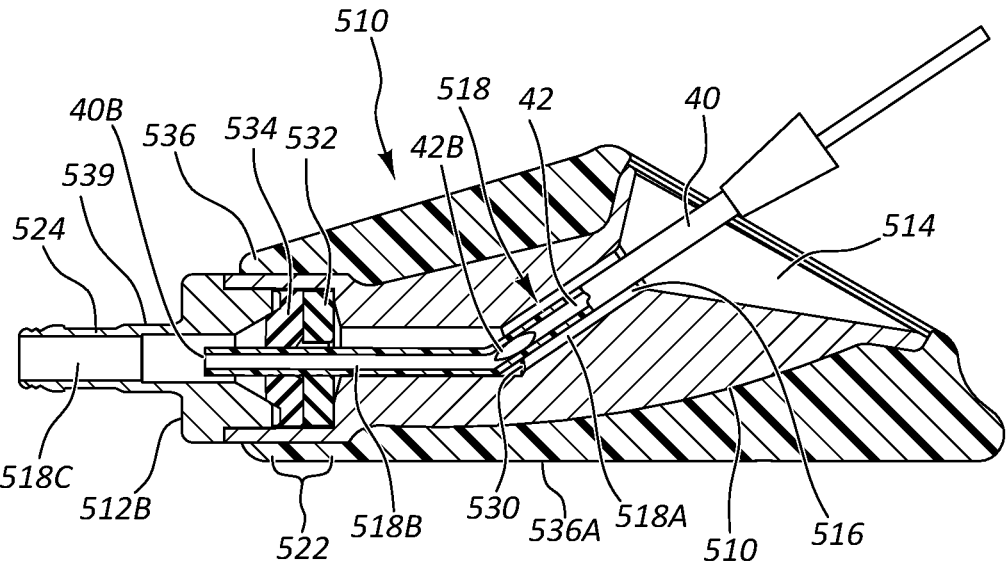

Once the distal end 40B of the catheter 40 has extended distally past the valve/seal assembly 522, further advancement is prevented by impingement of the catheter distal end against an annular stop surface 539 included in the third conduit portion 518C defined by the stem 524, as shown in FIG. 14D and in more detail in FIG. 11. In one embodiment, the stop surface 539 is defined as an annular shoulder and is sized so as to stop advancement of one size of catheter, such as 14 Gauge catheter, while allowing a 16 Gauge catheter to pass. In another embodiment, no stop surface is included in the conduit 518, thus enabling the catheter 40 to advance completely past the distal end of the stem 524, if desired. Note that the port conduit can be configured to accept one or more of a variety of catheter Gauge sizes, including 14 Gauge, 16 Gauge, 18 Gauge, etc.

Once the catheter 40 is positioned as shown in FIG. 14D, the needle 42 can be fully removed and fluid transfer through the catheter 40 and port 510 can commence, including infusion and/or aspiration through an indwelling catheter attached to the stem 524. (Note that the needle 42 can be removed at another stage of the catheter insertion procedure, in one embodiment.) Dressing of the catheter 40 can also occur as needed. Once fluid transfer is completed, the catheter 40 can be withdrawn proximally through the valve/seal assembly 522 and the conduit 518, then withdrawn through the surface of the skin and out of the patient.

FIG. 9F depicts that, in the present embodiment, the receiving cup 514 includes radiopaque indicia 528 to indicate a characteristic of the port 510. Here, the radiopaque indicia 528 includes an "IVCT" alphanumeric designation that is defined as a depression or recess into the titanium material forming the first body portion 512A so as to be visible after port implantation via x-ray imaging technology. The "IVCT" designation indicates that the port 510 is configured for power injection and is further configured to receive therein a peripheral IV catheter.

In another embodiment the radiopaque indicia 528 can be included by employing radiopaque material that can be formed as an insert that is insert-molded included in the port body, such as an initially flowable material that is injected into a cavity of the port body before hardening, etc. In embodiments where the port body is metallic, the radiopaque indicia can be formed by metal injection molding, machining, etching, engraving, or otherwise producing a relative thickness difference between the indicia and the surrounding port body material so as to produce an x-ray-discernible contrast that shows up in an x-ray image, similar to FIG. 1F.

In addition to above designation, other characteristics can be indicated by various other types of radiopaque indicia as appreciated by one skilled in the art.

As in other embodiments described herein, in one embodiment the perimeter of the receiving cup (or other suitable location) can include palpation features, such as three raised bumps in the overmolded portion 536 to assist in locating the position of the receiving cup 514 post-implantation when they are palpated by a clinician prior to needle insertion into the patient. Various other palpation features could be included with the port, in other embodiments, including disposal on the receiving cup itself, etc.

Figure 15A:
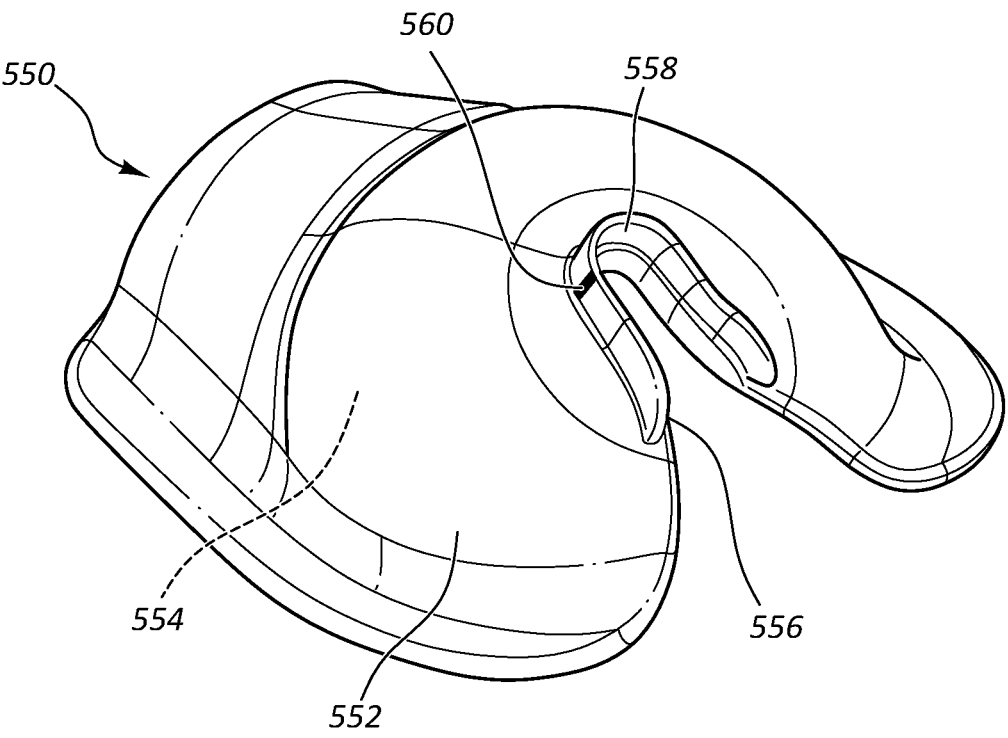
FIGS. 15A and 15B depict various views of a guide device for use with the access device of FIGS. 9A-9G according to one embodiment.
Figure 15B:
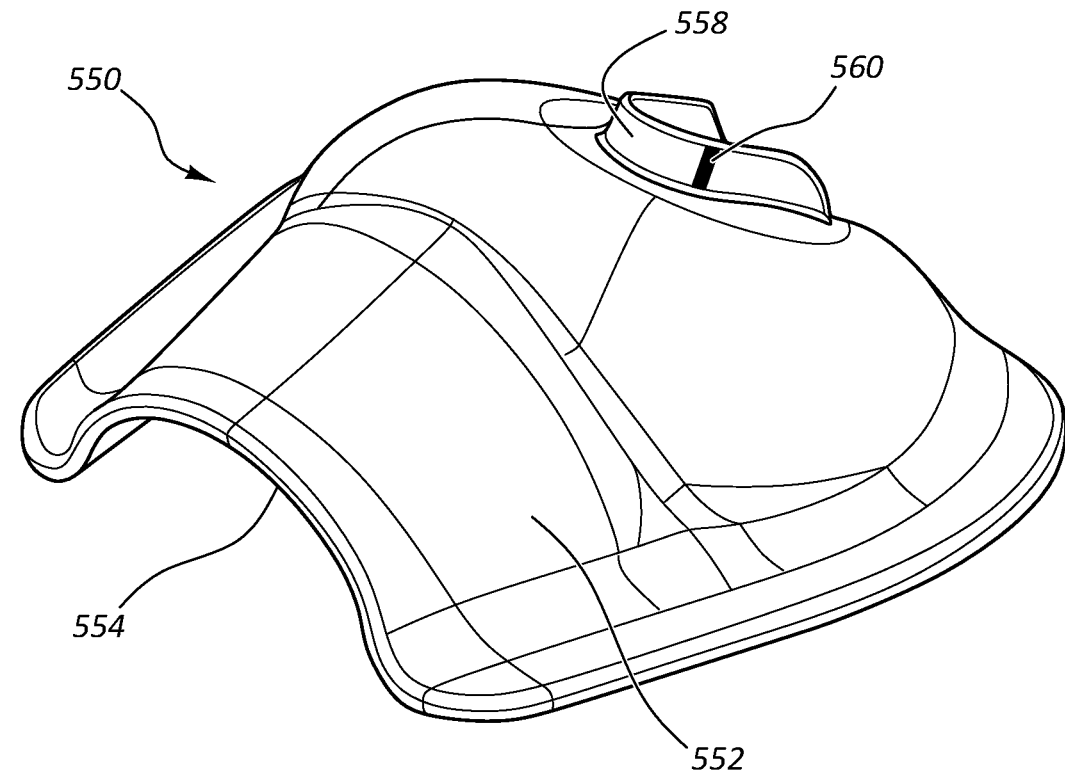

FIGS. 15A and 15B depict details of a guide device 550 that can be placed on the patient skin atop the implanted location of the port 510 shown in FIGS. 9A-9G to assist in guiding the needle 42 through the skin so as to impinge on the receiving cup 514, as desired. As shown, the guide device 550 includes a body 552 that defines a cavity 554 into which a portion of the subcutaneous implanted port 510 will reside when the guide device is pressed on the skin over the port. A notch 556 is included on the body 552, partially bordered by a ridge 558. The notch 556 enables the needle 42 to be passed therethrough so as to be inserted through the skin and into port 510. A marker line 560 is included on the ridge 548 to assist the clinician in placing the needle 42 at the proper orientation and location for impingement on the receiving cup 514, as desired. Note that the shape, size, and other configuration of the guide device can vary from what is shown and described herein.

Figure 25A:
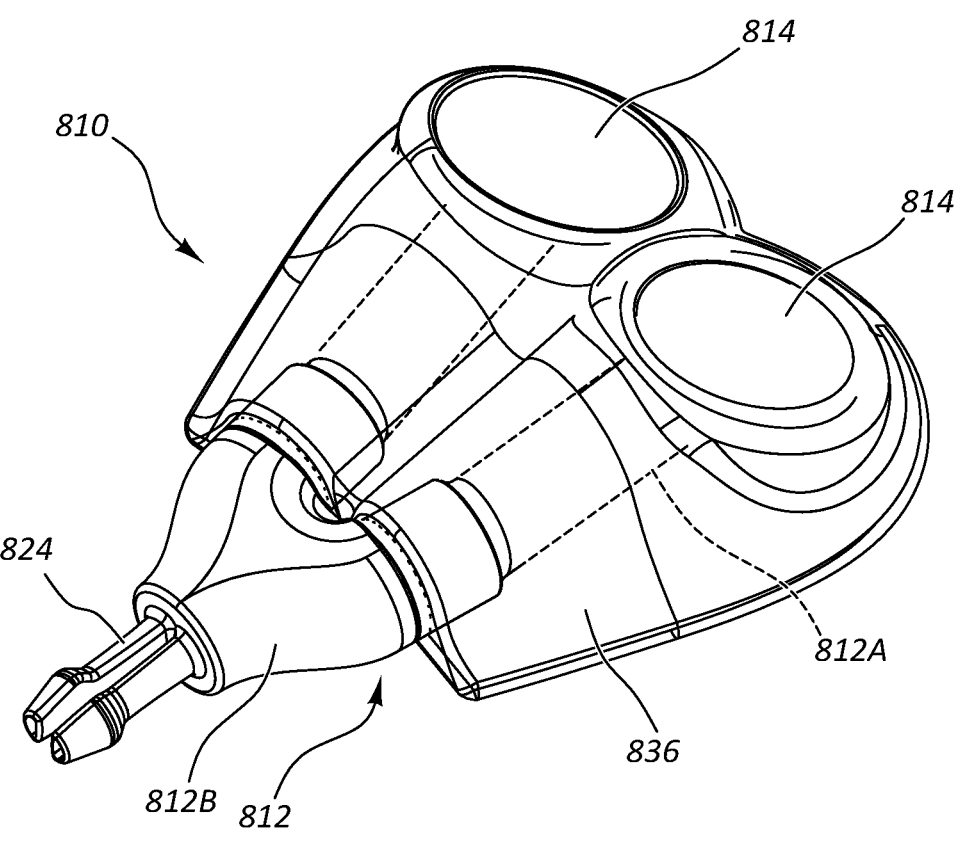
FIGS. 25A-25E depict various views of a low-profile vascular access device according to one embodiment.
Figure 25B:
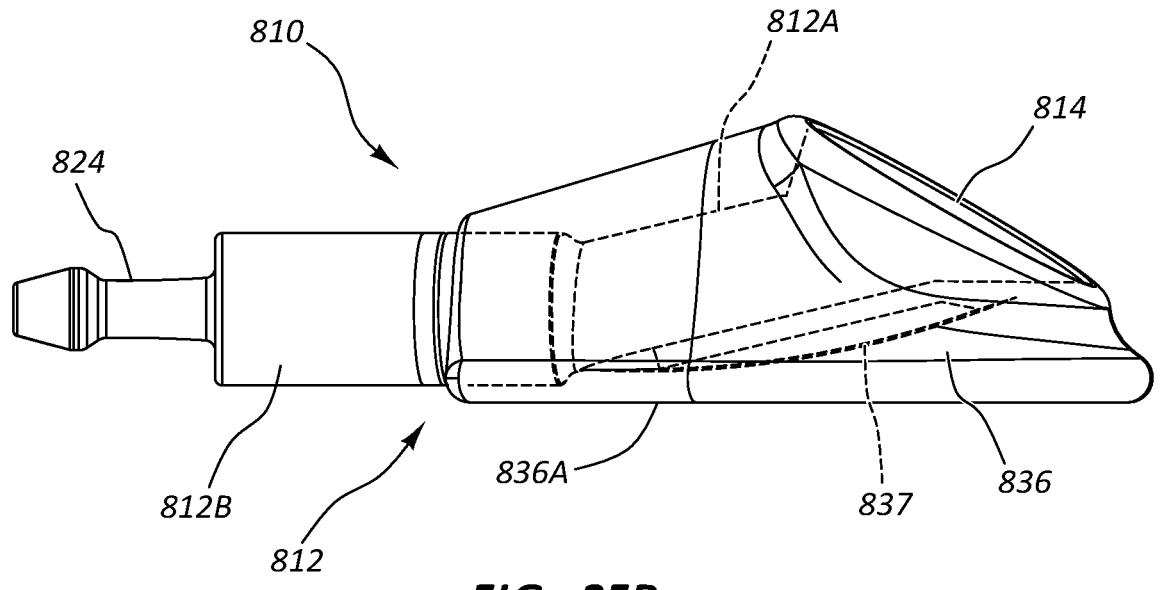
Figures 25C, 25D:
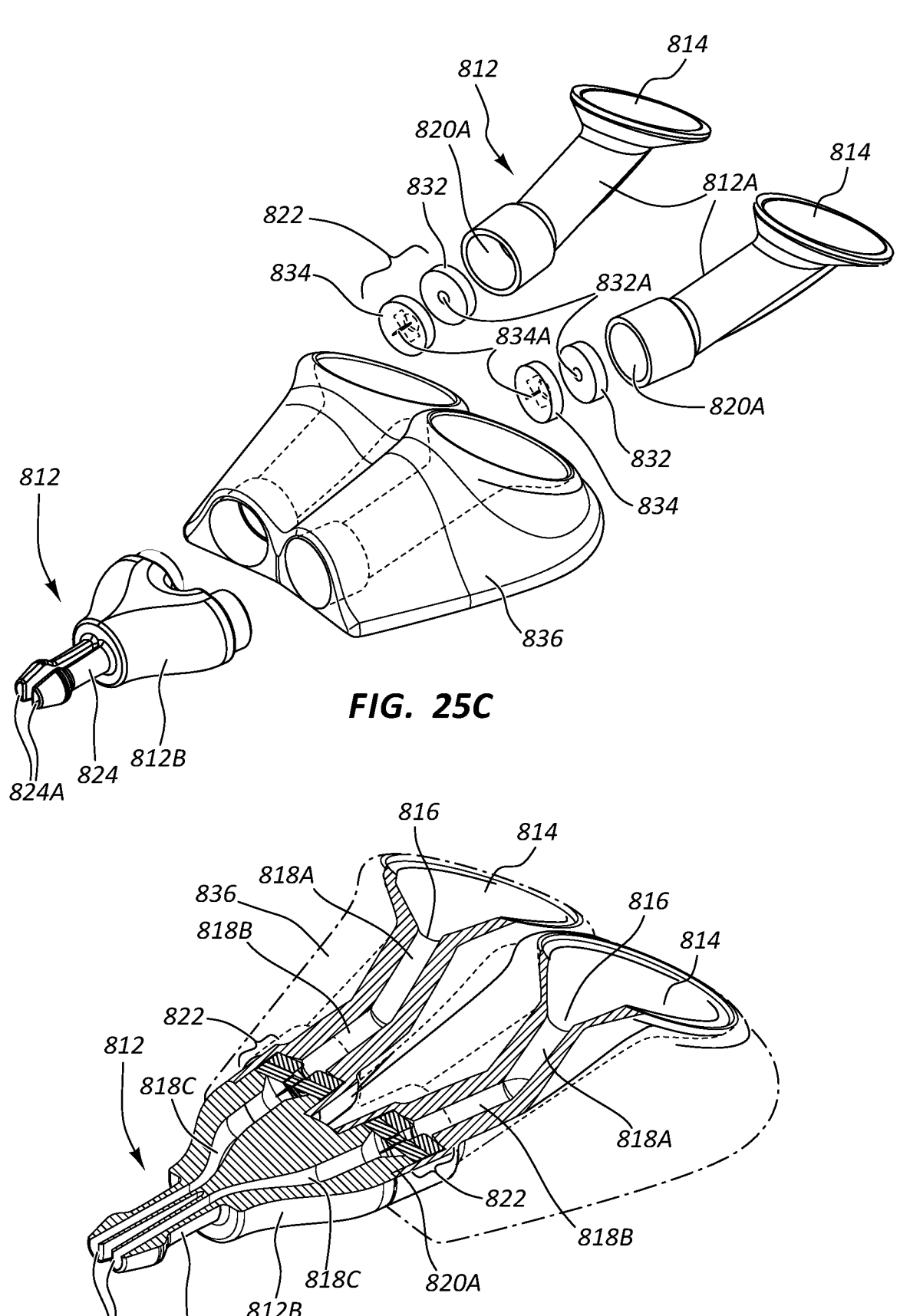

Reference is now made to FIGS. 25A-25E, which show various details of a dual-lumen vascular access device, generally designated at 810, in accordance with one embodiment. As shown, the port 810 includes a body 812 that is defined in the present embodiment by two similarly shaped portions: a single first portion 812A and a single second portion 812B (FIG. 25C). In the present embodiment the port body first and second portions 812A, 812B include a metal such as titanium, and as such, the second portion is press fit into engagement with the first portion to define the body, though it is appreciated that the port body can include a variety of other materials, including metals, thermoplastics, ceramics, etc., and can include other joining methods including adhesive, ultrasonic or other welding, interference fit, etc.

Both port body first portions 812A define in the present embodiment a substantially funnel-shaped receiving cup 814 for receiving and directing the catheter-bearing needle 42 (FIG. 14A) to operably connect with the port 810 in a manner similar to that already described above. In particular, the substantially funnel shape of each receiving cup 814 is configured to direct the catheter-bearing needle 42 impinging thereon toward an inlet port 816 that serves as an opening for a respective conduit 818 defined by the port body 812. The open and shallow nature of each receiving cup 814, angled toward the skin surface of the patient enables the receiving cup to present a large, easily accessible target for the needle when introduced into the skin and directed toward the subcutaneously implanted access port 810. FIG. 25B further shows that the access port 810 defines a relatively low profile height, which enables relatively shorter needle lengths to be used for accessing the subcutaneous access port after implantation.

Note that, as already mentioned, palpation features can be included with the port body 812 in one embodiment to assist a clinician to locate and/or identify the port 810 via finger palpation after implantation under the skin of the patient. Note that a variety of sizes, configurations, numbers, etc., of palpation features can be included on the port. In another embodiment, a guide groove can be defined on the receiving cup 814 to be longitudinally aligned with the inlet port 816 of the conduit 818, as discussed in connection with the embodiment of FIGS. 1A-2. The guide groove can be defined as a depression with respect to adjacent portions of the surface of the receiving cup 814 and extend distally along the receiving cup surface from a proximal portion of the receiving cup so as to provide a guide path to guide the distal tip of the catheter-bearing needle toward the inlet port 816 once impingement of the needle into the guide groove is made. This in turn reduces the chance the needle will slide across and off the receiving cup 814 during insertion. Note that these and other similar features, though differing in shape and configuration, can also be included on the other ports disclosed herein.

As best seen in FIG. 25D, the port body 812 further defines the two conduits 818, each conduit serving as a pathway into which a transcutaneously inserted catheter can be partially inserted so as to place the catheter in fluid communication both with the port 810 and an indwelling dual-lumen catheter operably attached to two fluid outlets 824A of a stem 824 of the port. As shown, the conduit 818 of each port body first portion 812A is in fluid communication with its respective receiving cup 814 via the inlet port 816. A first conduit portion 818A of the conduit 818 distally extends from the inlet port 816 in an angled downward direction from the perspective shown in FIG. 25D to a conduit bend 830, where a second conduit portion 818B of the conduit extends at a predetermined angle with respect to the first conduit portion. Note that predetermined angle at the bend 830 in one embodiment is about 34 degrees, but can vary from this in other embodiments, including angles smaller or greater than 34 degrees in one embodiment. The magnitude of the predetermined angle at the bend 830 depends in one embodiment on various factors, including the size of the catheter and/or needle to be inserted into the port conduit, the size of the conduit itself, etc. Note also that the conduit bend 830 serves as a needle-stop feature, preventing the needle 42 from advancing along the conduit 818 past the bend 830.

The second conduit portion 818B of each port body first portion 812A distally extends to a cavity 820A defined by the press-fit junction of the port body first portion and the second portion 812B, as seen in FIG. 25D. Two third conduit portions 818C are defined by the second portion 812B of the port body 812 and extend from each of the cavities 820A in a partially arcuate fluid path to the distally-disposed fluid outlets 824A of the stem 824. In the present embodiment the conduit 818 is sized so as to enable the catheter 40 (FIG. 14A) to pass therethrough and past the cavity 820A.

As mentioned, the cavities 820A, each defined by the junction of the respective first portion 812A and the second portion 812B of the port body 812, each define a space through which the conduit 818 passes and in which is housed a valve/seal assembly 822. In the present embodiment and as best seen in FIGS. 25C and 25D, the valve/seal assembly 822 includes a sealing element, or seal 832, which defines a central hole 832A through which the catheter 40 (FIGS. 14A, 14D) can pass, and a slit valve 834 including two orthogonally intersecting slits 834A through which the catheter also passes. The seal 832 and slit valve 834 are sandwiched together in one embodiment, with the seal disposed proximal to the slit valve, and secured in place within the correspondingly sized cavity 820A as shown in FIG. 25D.

As mentioned, the slits 834A of the slit valve 834 are orthogonally offset from one another by about 90 degrees in the present embodiment, though other relationships are possible, including the use of two single-slit valves sandwiched together with one another. Note that in the present embodiment the slit valve 834 includes a central depression (as in previous embodiments, such as is shown in FIG. 13A, for instance) to ease the transition of passage of the catheter 40 from the seal 832 to the valve. More than one seal and/or slit valve may be employed in the valve/seal assembly in other embodiments.

As with previous embodiments, the seal 832 and slit valve 834 of the valve/seal assembly 822 cooperate to enable fluid-tight passage therethrough of the catheter 40 (see, e.g., FIG. 14A) while also preventing backflow of fluid through the valve/seal assembly. Indeed, in one embodiment the seals disclosed herein prevent fluid flow around the external portion of the catheter when the catheter is disposed through the seal 832, while the valve 834 is suitable for preventing fluid flow when no catheter passes through them. As such, when the catheter 40 is not inserted therethrough the valve/seal assembly 822 seals to prevent passage of air or fluid through the conduit 818. In the present embodiment, the seal 832 and valve 834 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 832 and valve 834 to enhance lubricity and extend component life. In another embodiment, the silicone oil is infused into the silicone.

The port 810 in the present embodiment includes an overmolded portion 836 that covers a portion of the port body 812, including a majority portion of each of the two first portions 818A. The overmolded portion 836 includes silicone, such as SILASTIC® Q7-4850 liquid silicone rubber or other suitably compliant material and surrounds the portions of the body 812 as shown in FIGS. 25A and 25B so as to provide a relatively soft surface for the port 810 and reduce patient discomfort after port implantation within the patient body. The overmolded portion 836 further enables a clinician to suture through one or more of various portions of the overmolded portion to enable the port 810 to be secured within a subcutaneous patient tissue pocket. The overmolded portion 836 further defines a relatively flat bottom surface 836A so as to provide a stable surface for the port 810 in its position within the tissue pocket after implantation into the patient body.

FIG. 25B shows that the first body portions 812A each define a securement ridge 837 that serves as an anchor to prevent relative movement between the overmolded portion 836 and the body 812. The securement ridge 837 can vary in shape, number, configuration, etc. Note that the overmolded portion 836 in one embodiment is molded in a molding process over the body 812. In another embodiment, the overmolded portion 836 is separately formed then adhesively attached to the body 812, such as via Med A adhesive. These and other configurations are therefore contemplated.

Figure 25E:
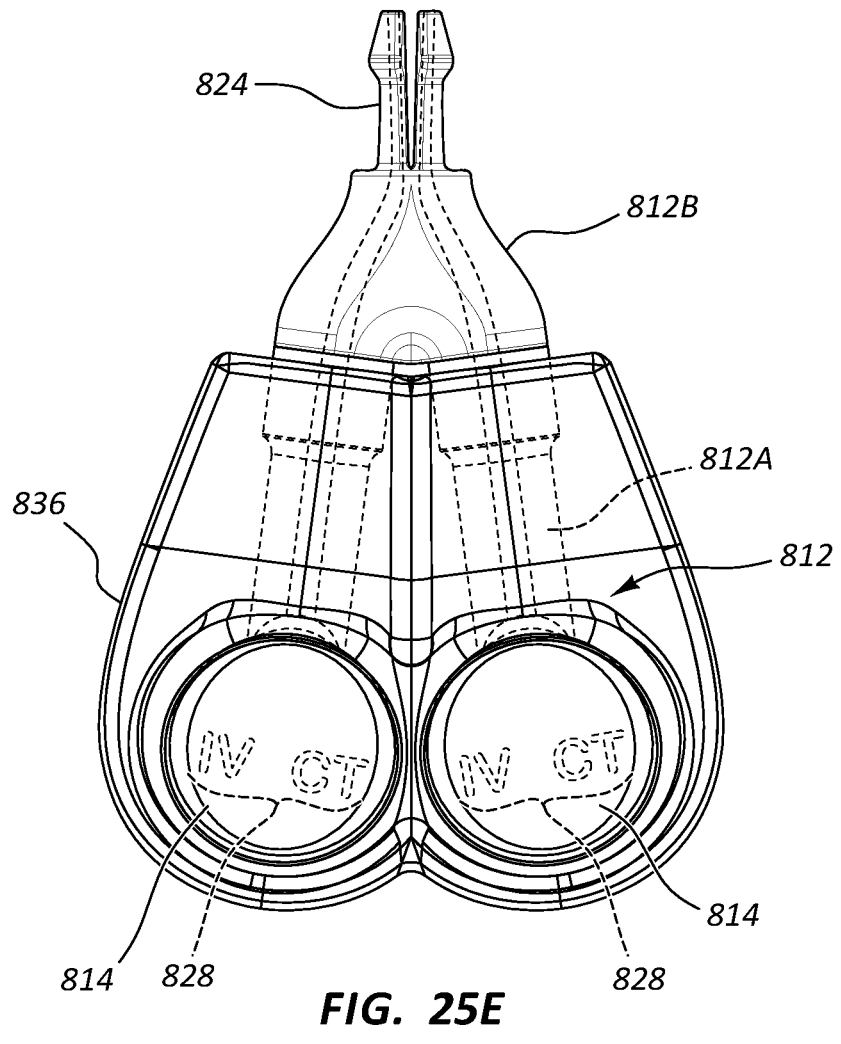
Figure 26A:
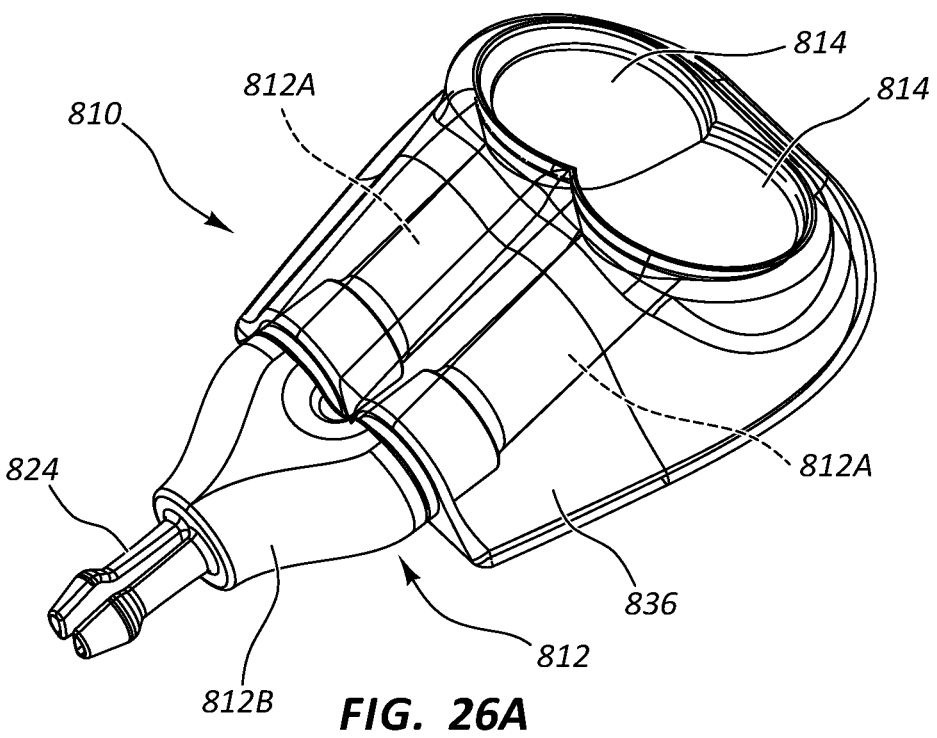
FIGS. 26A-26D depict various views of a low-profile vascular access device according to one embodiment.
Figure 26B:
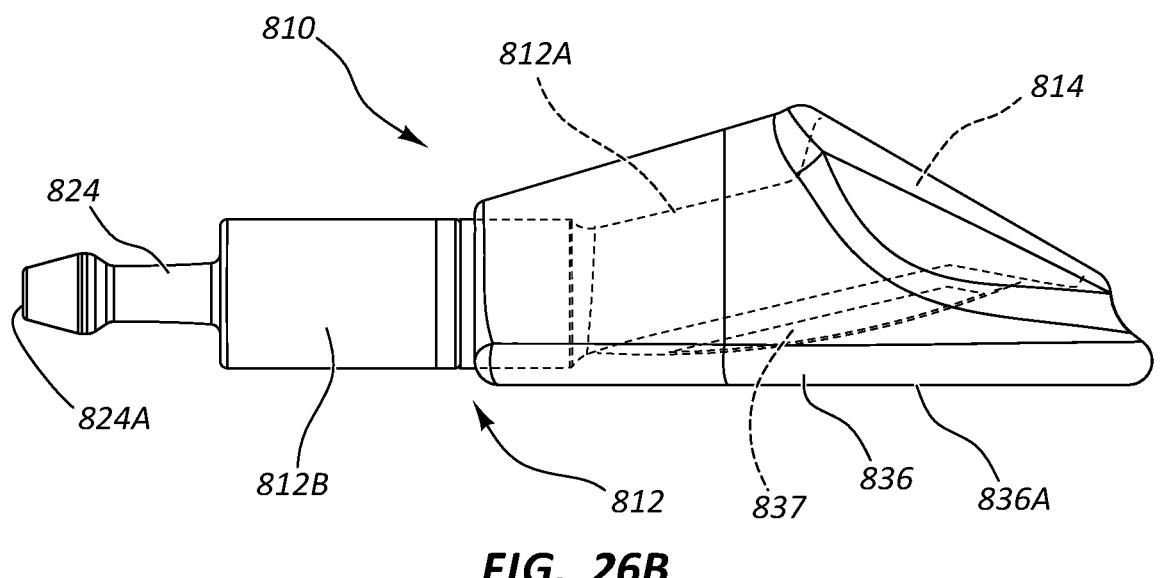
Figure 26C:
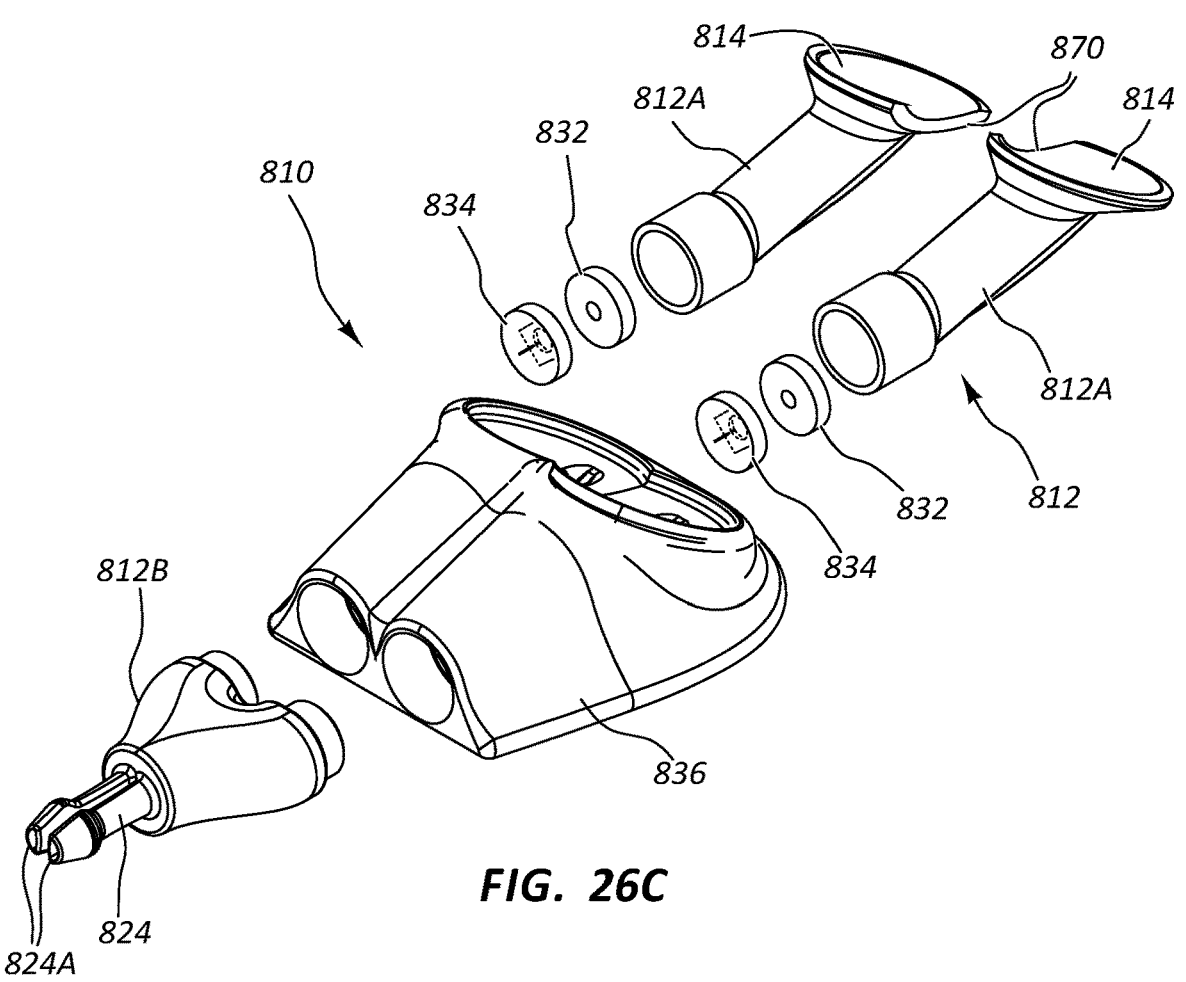
Figure 26D:
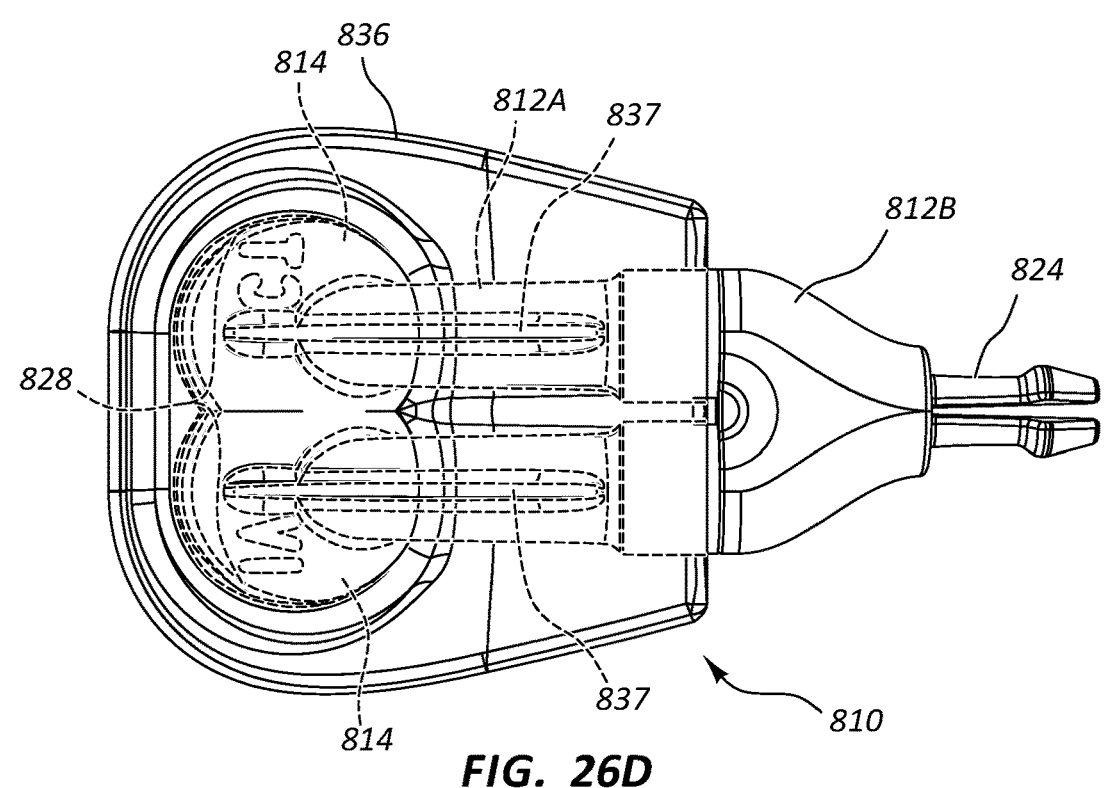

FIG. 25E shows that underside surfaces of the receiving cups 814 include a radiopaque indicia 828 configured to enable the port 810 to be radiographically identified after implantation into the patient body. In the present embodiment each of the indicia 828 includes the letters "IV" and "CT" to indicate suitability of the port 810 to receive peripheral IV catheters and that the port is capable of power injection of fluids therethrough. Of course, a variety of other indicia, including letters, numbers, symbols, etc., may be used.

FIGS. 26A-26D depict various details of the port 810 according to another embodiment, wherein the port body 812 defines a relatively slimmer profile than the embodiment shown in FIGS. 25A-25E, made possible by defining a cutout 870 on both receiving cups 814 of each first portion 812A of the port body 812. This enables the receiving cups 814 to reside relatively close to one another. The receiving cups 814 can be joined to one another along the cutouts 870 via welding, adhesive, forming the receiving cups together as a single component, etc.

Figure 31:
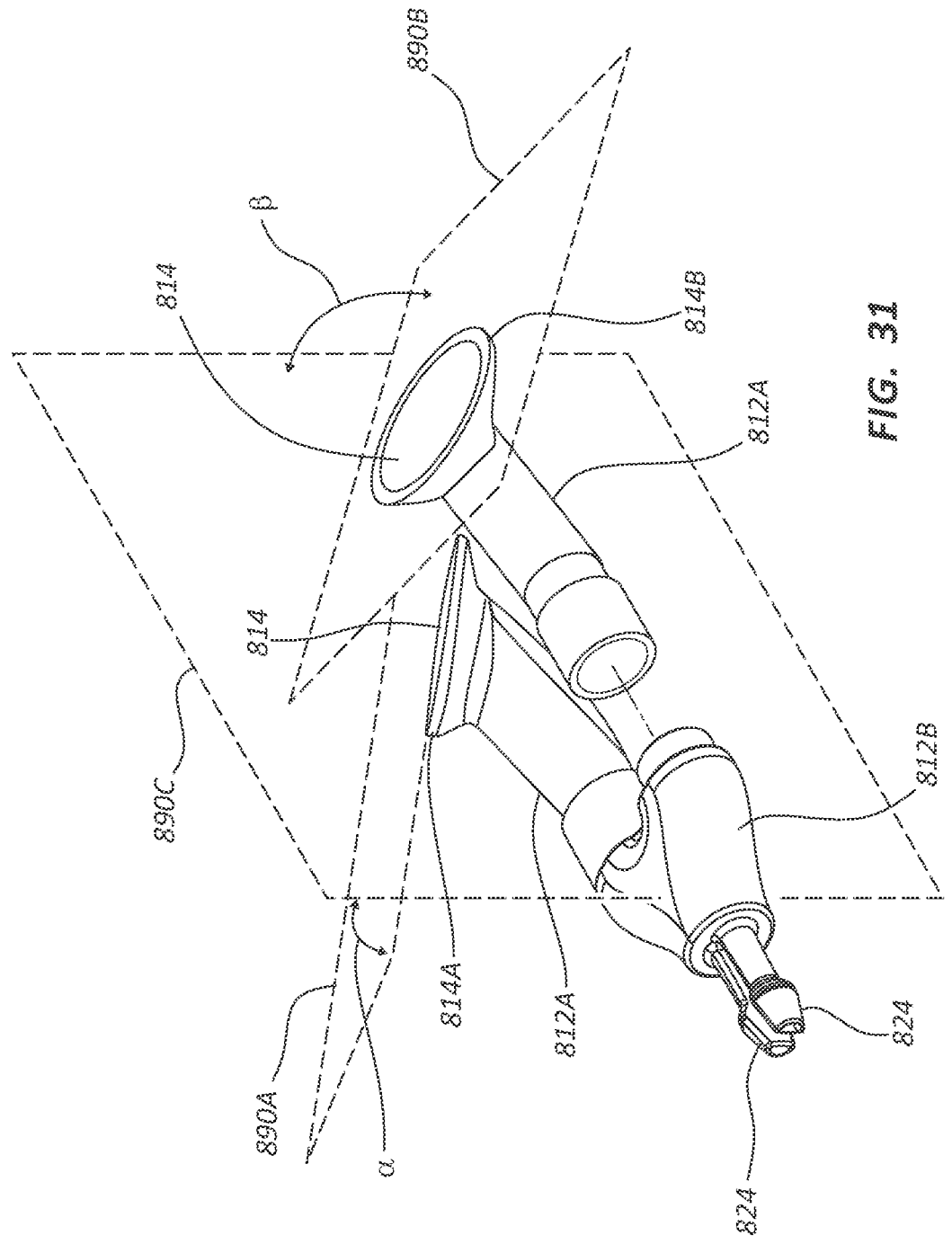
FIG. 31 is a perspective view of a portion of a vascular access device according to one embodiment.

In one embodiment, it is appreciated that the receiving cups 814 can be oriented in other configurations. FIG. 31 gives an example of this, wherein a partially exploded view of the port 810 is shown without the overmolded portion 836 present, and thus including the two first portions 812A and the second portion 812B. As shown, the receiving cups 814 are angled with respect to one another such that a perimeter 814A of a corresponding one of the receiving cups lies in an imaginary plane 890A that is non-parallel to another plane 890B in which a perimeter 814B of the other receiving cup lies. This is in contrast to another embodiment, such as that shown in FIG. 25A, wherein the receiving cups 814 sub-
stantially lie in a single imaginary plane. The configuration
of FIG. 31 results in the receiving cups 814 being angled
away from one another, as shown in FIG. 31, such that the
non-parallel imaginary planes 890A and 890B form different
positive angles, α and β respectively, with respect to an
imaginary bisecting plane 890C between the receiving cups
814 (note that the first body portion 812A shown discon-
nected (for clarity) from the second body portion 812B is to
be connected to the second body portion in substantially the
same orientation as shown in FIG. 31). This, in turn,
desirably results in a slightly lower height profile for the
access port 810, and can also result in the needle 42 inserted
therein residing relatively closer to the patient skin, in one
embodiment. Note that the receiving cups can be angled in
various different configurations in addition to what is shown
and described herein.

Reference is now made to FIGS. 16A-21B, which depict
details of a dual-lumen vascular access device, generally
designated at 610, in accordance with one embodiment. As
shown, the port 610 includes a body 612 that is defined in
the present embodiment by a first portion 612A and a
relatively smaller second portion 612B that is partially
received within the first portion. In the present embodiment
the port body first and second portions 612A, 612B include
a metal such as titanium, and as such, the second portion is
press fit into engagement with the first portion to define the
body, though it is appreciated that the port body can include
a variety of other materials, including metals, thermoplas-
tics, ceramics, etc., and can include other joining methods
including adhesive, ultrasonic or other welding, interference
fit, etc.

The port body first portion 612A defines in the present
embodiment two substantially funnel-shaped receiving cups
614 for receiving and directing the catheter-bearing needle
42 (FIG. 14A) to operably connect with the port 610 in a
manner similar to that already described above. The receiv-
ing cups 614 in the present embodiment are disposed so as
to be substantially aligned along a longitudinal axis of the
port 610, though other positional arrangements for the
receiving cups are possible, including side-by-side, spaced-
apart, staggered, etc.

Figure 16A:
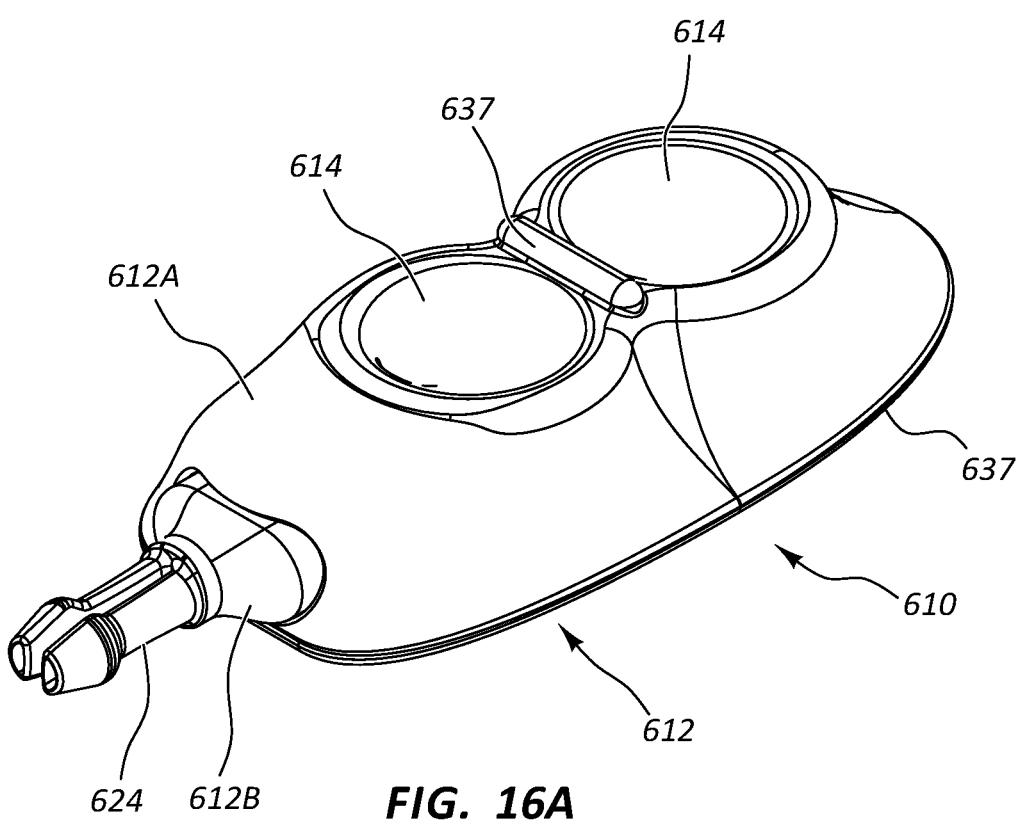
FIGS. 16A-16G depict various views of a low-profile vascular access device according to one embodiment.
Figure 16B:
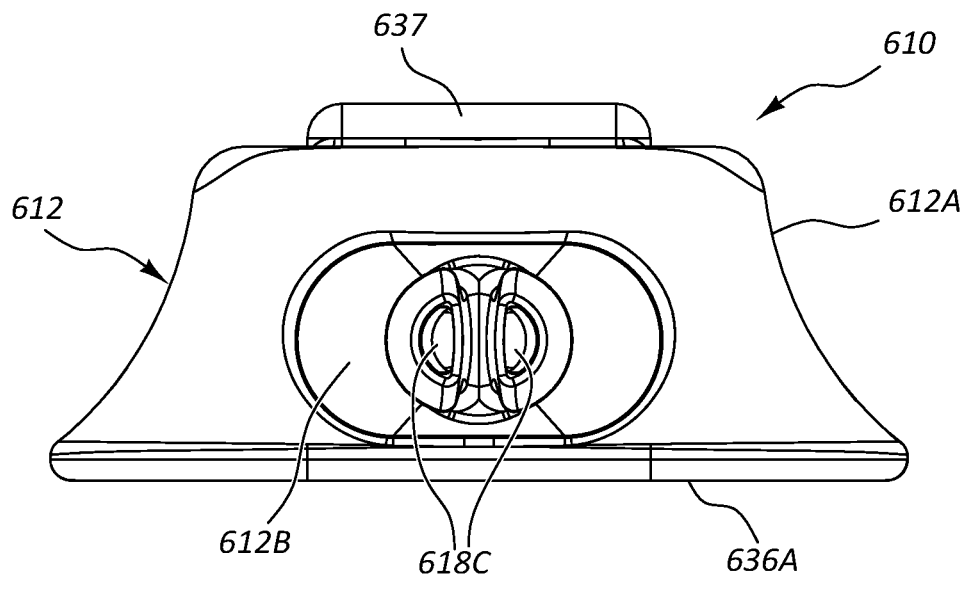
Figure 16C:
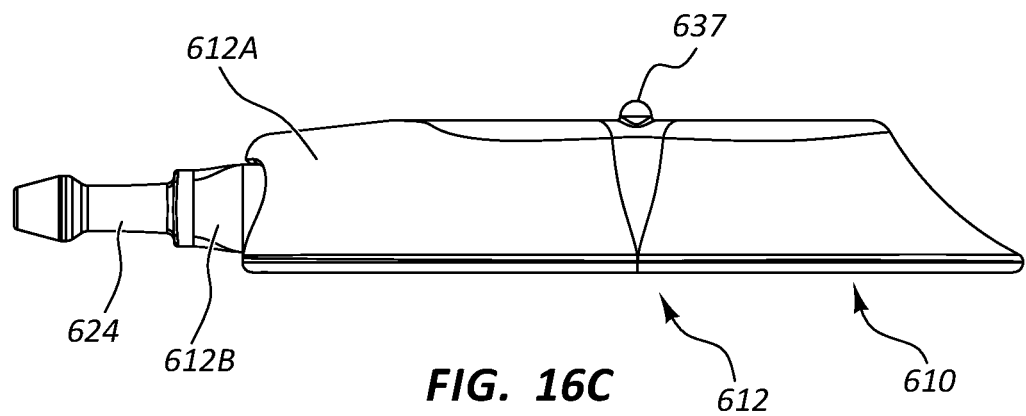
Figure 16D:
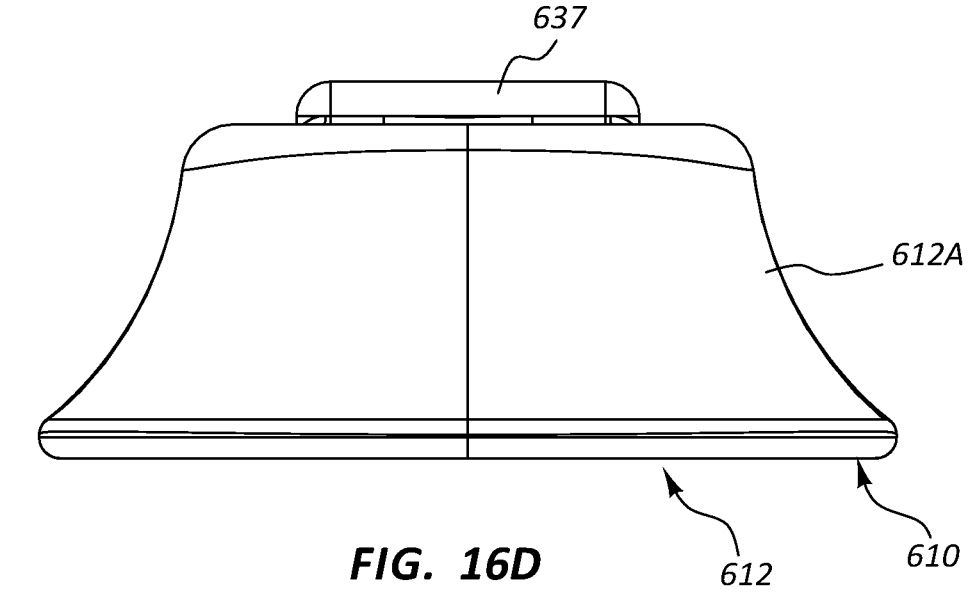
Figure 16E:
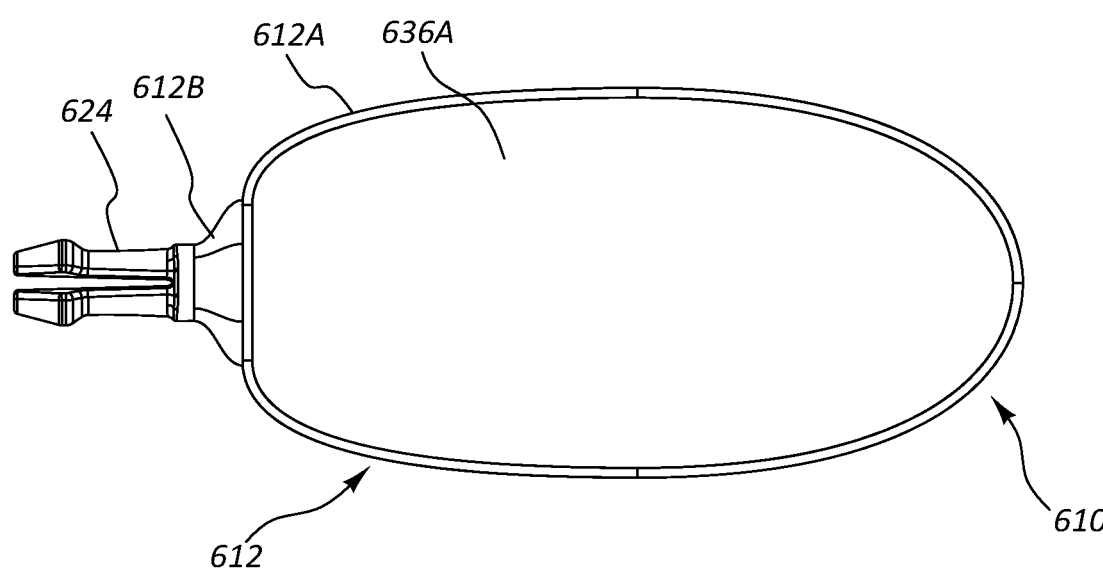
Figure 16F:
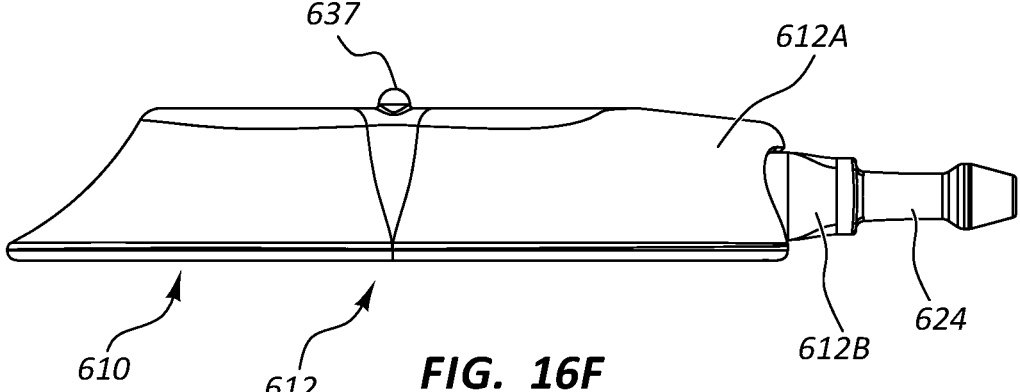
Figure 16G:
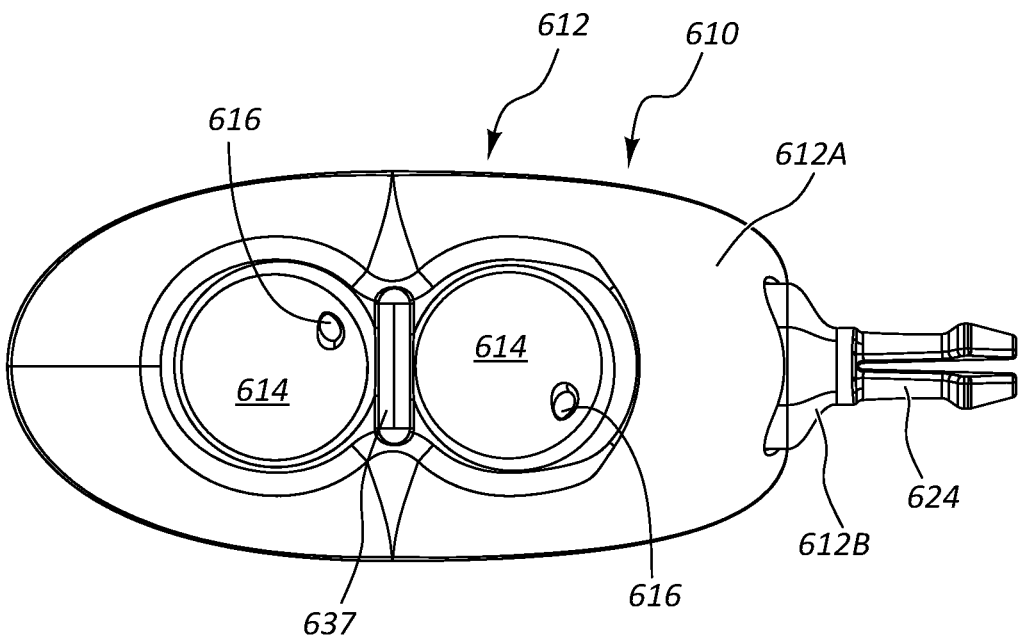

In particular, the substantially funneled-shape of each
receiving cup 614 is configured to direct the catheter-bearing
needle 42 impinging thereon toward an inlet port 616 that
serves as an opening for a respective one of two conduits
618 defined by the port body 612, one conduit for each
receiving cup. The open and shallow nature of each receiv-
ing cup 614, angled toward the skin surface of the patient
enables the receiving cup to present a large, easily accessible
target for the needle when introduced into the skin and
directed toward the subcutaneously implanted access port
610. FIGS. 16C and 16F further show that the access port
610 defines a relatively low profile height, which enables
relatively shorter needle lengths to be used for accessing the
subcutaneous access port after implantation.

The port body 612 further defines a palpation feature 637,
here configured as a raised surface interposed between the
longitudinally aligned receiving cups 614. As mentioned
above, the palpation feature 637 is included with the port
body 612 to assist a clinician to locate and/or identify the
port 610 via finger palpation after implantation under the
skin of the patient. Note that a variety of sizes, configura-
tions, numbers, etc., of palpation features can be included on
the port. In another embodiment, a guide groove can be defined on each receiving cup 614 to be longitudinally
aligned with the inlet port 616 of the conduit 618, as in
previous embodiments.

Figure 17A:
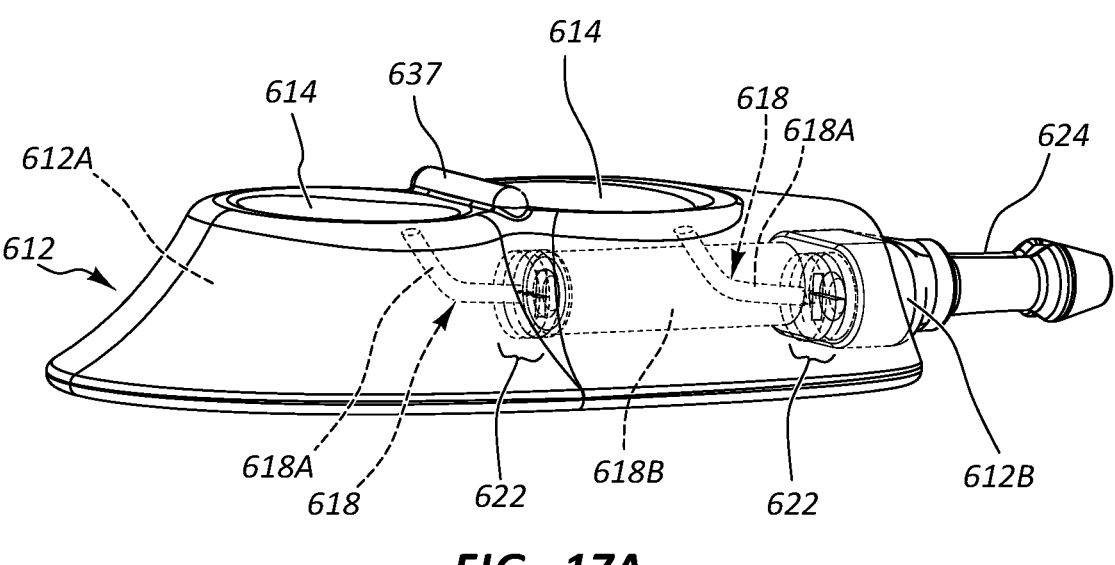
FIGS. 17A and 17B depict various views of the vascular access port of FIGS. 16A-16G.
Figure 17B:
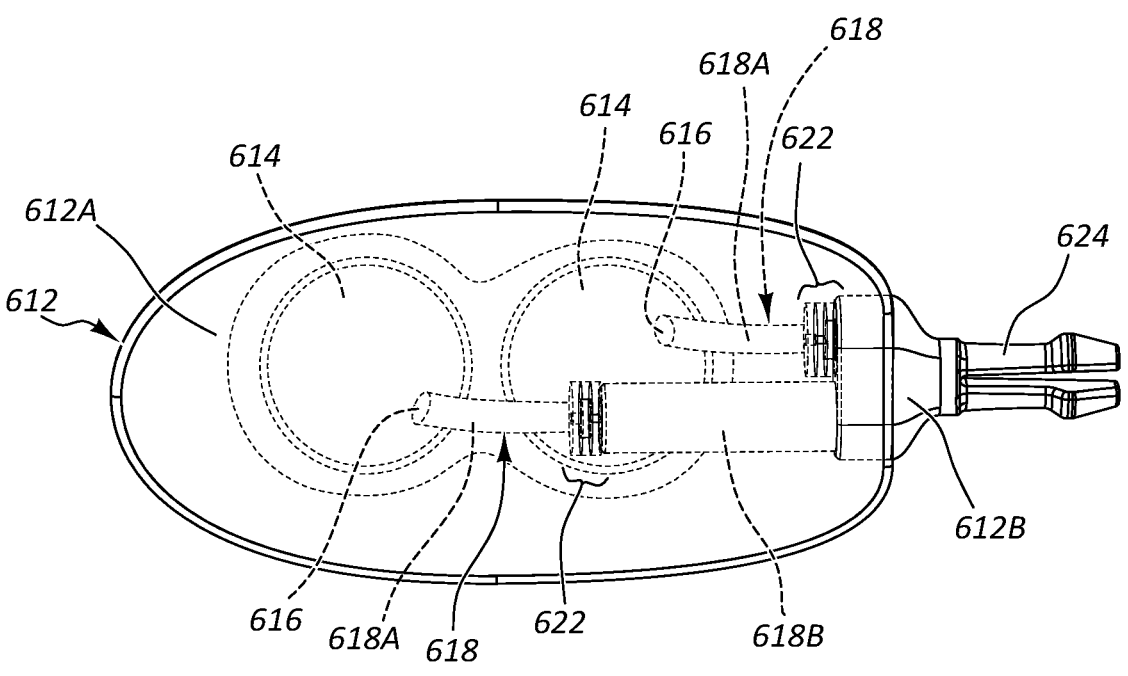
Figures 18, 19:
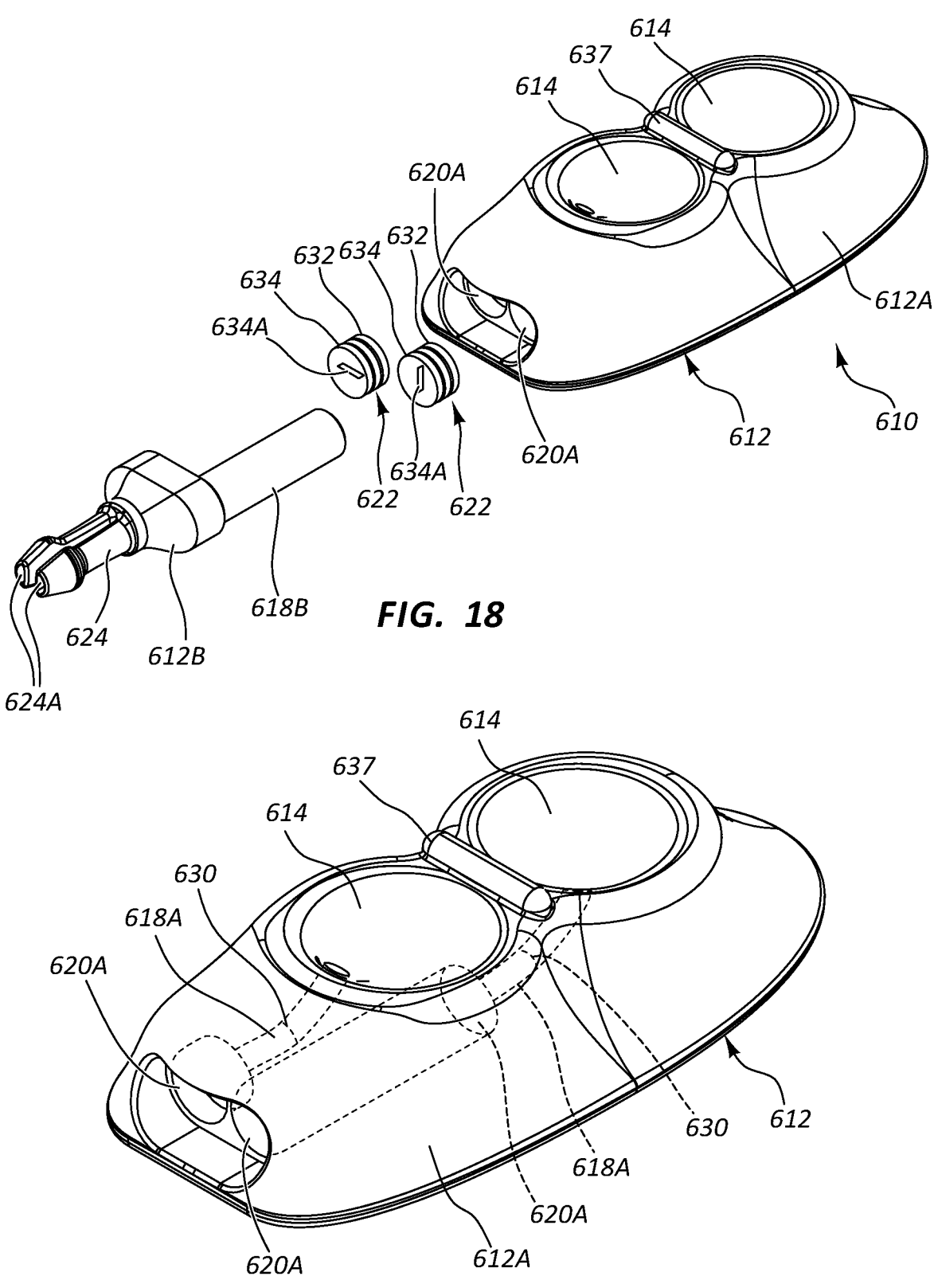
FIG. 18 is an exploded view of the vascular access device of FIGS. 16A-16G.
FIG. 19 is a partially transparent view of the vascular access device of FIGS. 16A-16G.

As best seen in FIGS. 17A, 17B, and 19, the port body
612 further defines the above-mentioned two conduits 618,
each conduit serving as a pathway into which a transcuta-
neously inserted catheter can be partially inserted so as to
place the catheter in fluid communication both with the port
610 and an indwelling dual-lumen catheter operably
attached to two fluid outlets 624A of a stem 624 of the port.
As shown, the two conduits 618 of the port body first portion
612A are in fluid communication with their respective
receiving cup 614 via the corresponding inlet port 616. A
first conduit portion 618A of each conduit 618 distally
extends from the respective inlet port 616 in an angled
downward direction from the perspective shown in FIG.
17A to a conduit bend 630 (FIG. 19), where the first conduit
portion extends distally at a predetermined angle with
respect to the first conduit portion proximal to the conduit
bend. The magnitude of the predetermined angle at the bend
630 depends in one embodiment on various factors, includ-
ing the size of the catheter and/or needle to be inserted into
the port conduit, the size of the port and the conduit itself,
etc. Note also that the conduit bend 630 serves as a needle-
stop feature, preventing the needle 42 from advancing along
the conduit 618 past the bend 630.

The first portion 618A of the relatively more distal of the
two receiving cups 614 extends to a cavity 620A defined by
and proximate to the distal portion of the first portion 612A
of the port body 612, as best seen in FIGS. 18 and 19. The
first portion 618A of the relatively more proximal of the two
receiving cups 614 also extends to a cavity 620A that is
defined by, but relatively more proximally distant from, the
distal portion of the first portion 612A of the port body 612
(FIGS. 18 and 19). A second conduit portion 618B is defined
for this latter conduit 618 by the second portion 612A of the
port body 612, as seen in FIGS. 17A and 17B and extends
distally from its respective cavity 620A until joining with a
third conduit portion 618C defined by the second portion
612A of the port body, which extends through the second
portion and the stem 624 until terminating at a respective
one of the fluid outlets 624A (FIG. 20).

Figure 20:
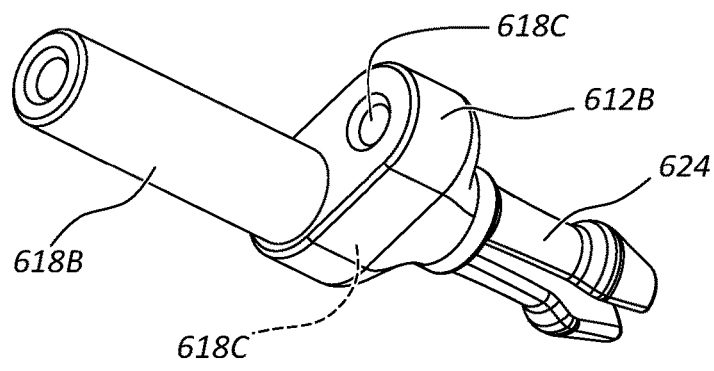
FIG. 20 is a perspective view of a portion of the vascular access device of FIGS. 16A-16G.
Figure 21A:
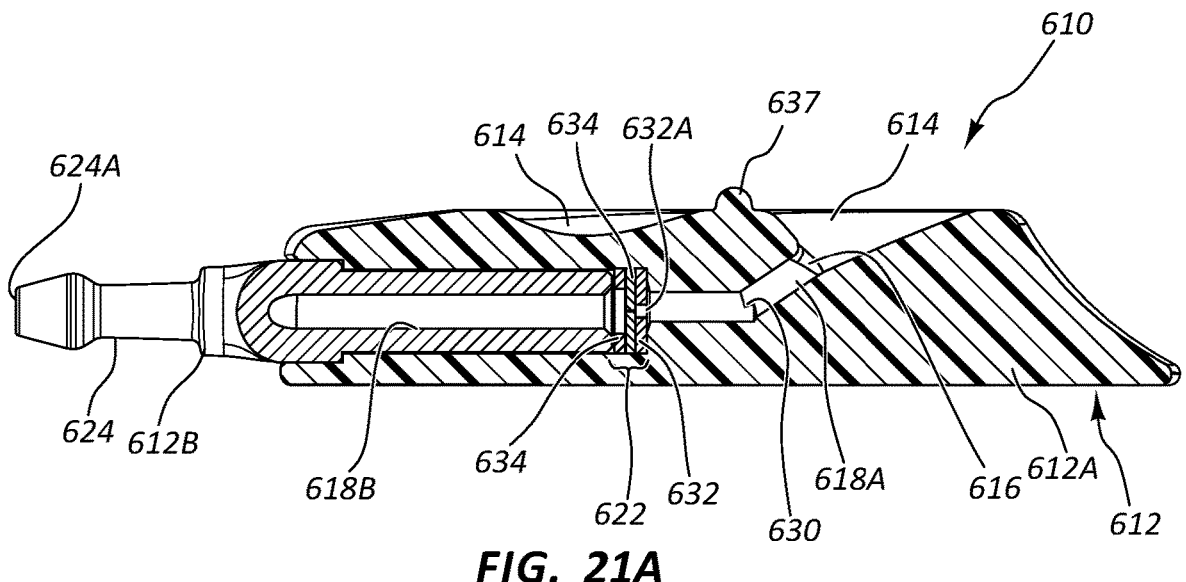
FIGS. 21A and 21B are cutaway views of the vascular access device of FIGS. 16A-16G.
Figure 21B:
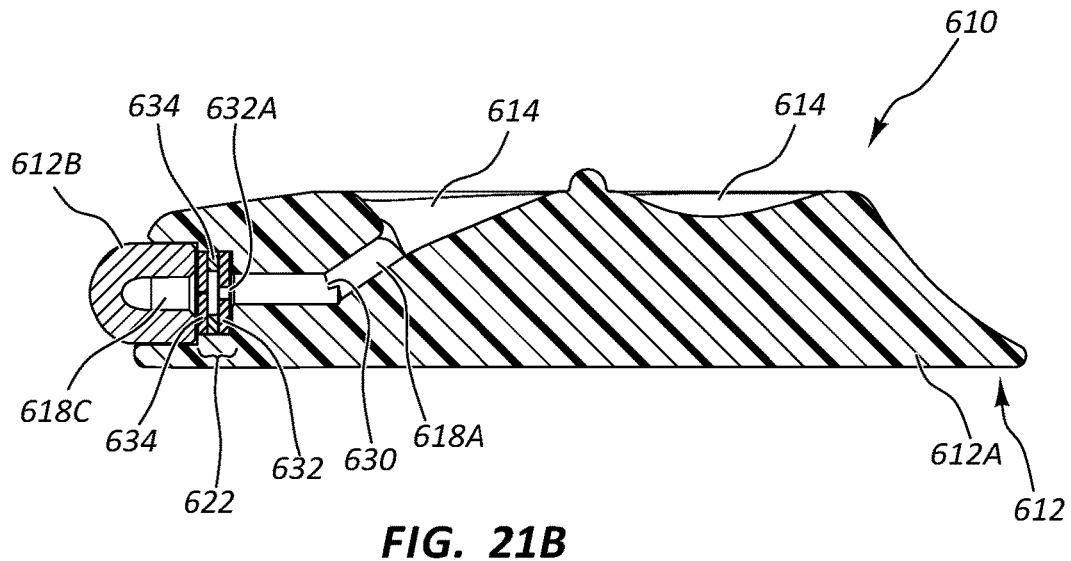

The conduit 618 for the relatively more distal receiving
cup 614 extends from the cavity 620A to a third conduit
portion 618C defined by the second portion 612A of the port
body 612, as seen in FIG. 20, which extends through the
second portion and the stem 624 until terminating at a
respective one of the fluid outlets 624A. In this way, fluid
pathways are defined for each receiving cup 614 from the
inlet port 616 to the stem fluid outlet 624A, as depicted in
FIGS. 21A and 21B. In the present embodiment the conduit
618 is sized so as to enable the catheter 40 (FIG. 14A) to
pass therethrough past the cavity 620A.

As mentioned, the cavities 620A, each disposed in the
fluid pathway defined by the various portions of the conduits
618, each define a space through which the conduit 618
passes and in which is housed a valve/seal assembly 622. In
the present embodiment and as best seen in FIGS. 17A-18,
each valve/seal assembly 622 includes a sealing element, or
seal 632, which defines a central hole 632A (FIG. 21B)
through which the catheter 40 (FIGS. 14A, 14D) can pass,
and two adjacently placed slit valves 634, each slit valve
including a single slit 634A (with the valves being arranged
such that the slits are orthogonal to one another), through
which the catheter also passes. The seal 632 and slit valves
634 are sandwiched together in one embodiment, with the
seal disposed proximal to the slit valve, and secured in place within the correspondingly sized cavity 620A as shown in FIGS. 17A and 17B. In another embodiment, the valve/seal assembly includes a single seal and a single, dual-slit valve, as in previous embodiments.

In the present embodiment, the seal 632 and valves 634 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 632 and valves 634 to enhance lubricity and extend component life. In another embodiment, the silicone oil is infused into the silicone. Also, and as has been mentioned with other embodiments, other seal/valve configurations can also be employed in the port 610.

Reference is now made to FIGS. 22A-24, which show various details of a dual-lumen vascular access device, generally designated at 710, in accordance with one embodiment. As shown, the port 710 includes a body 712 that is defined in the present embodiment by a first portion 712A defining the majority of the external portion of the port body and a second portion 712B that is matable to the first portion. In the present embodiment the port body first and second portions 712A, 712B include a metal such as titanium, and as such, the second portion is press fit into engagement with the first portion to define the body 212, though it is appreciated that the port body can include a variety of other materials, including metals, thermoplastics, ceramics, etc., and can include other joining methods including adhesive, ultrasonic or other welding, interference fit, etc.

The port body first portion 712A defines in the present embodiment two substantially concavely-shaped receiving cups 714, side-by-side in a spaced-apart arrangement, for receiving and directing the catheter-bearing needle 42 (FIG. 14A) to operably connect with the port 710 in a manner similar to that already described above. In particular, the substantially concave shape of each receiving cup 714 is configured to direct the catheter-bearing needle 42 impinging thereon toward an inlet port 716 that serves as an opening for a respective conduit 718 defined by the port body 712.

Figure 22A:
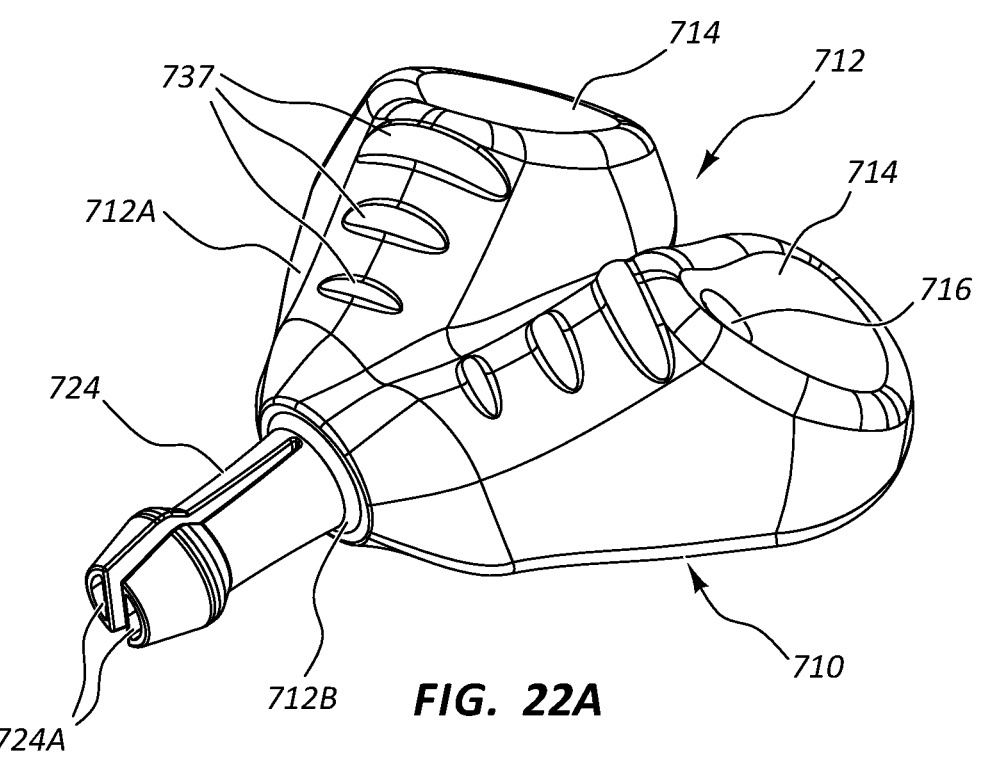
FIGS. 22A-22C depict various views of a low-profile vascular access device according to one embodiment.
Figure 22B:
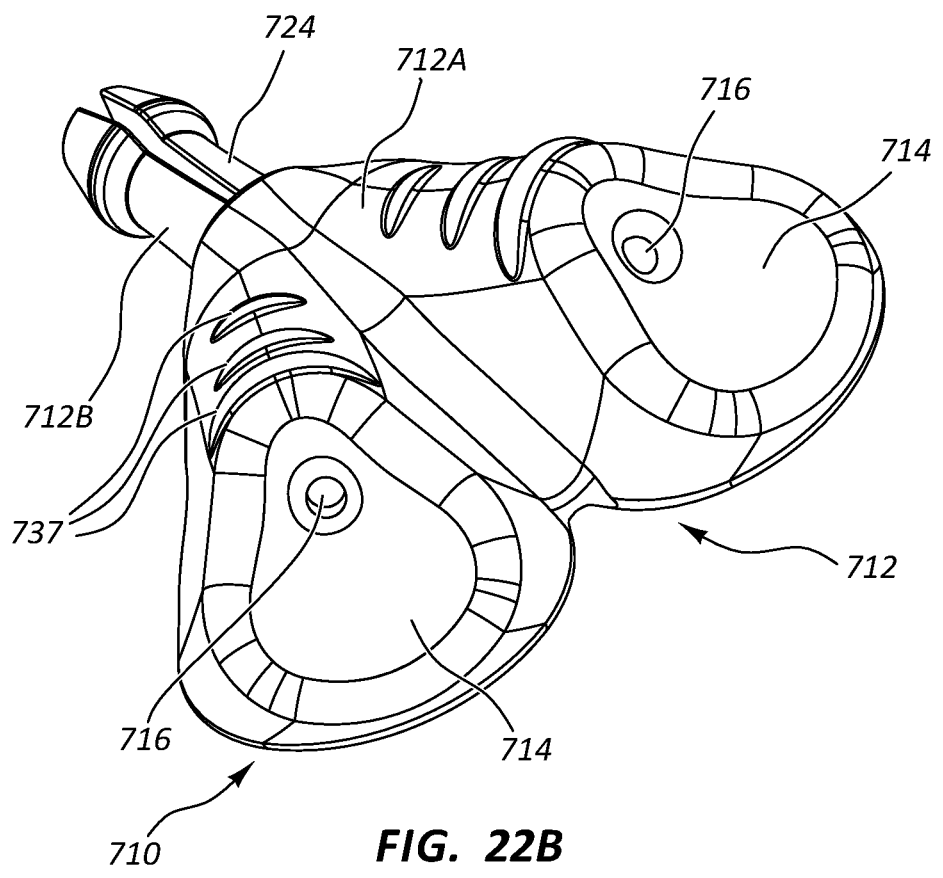
Figure 22C:
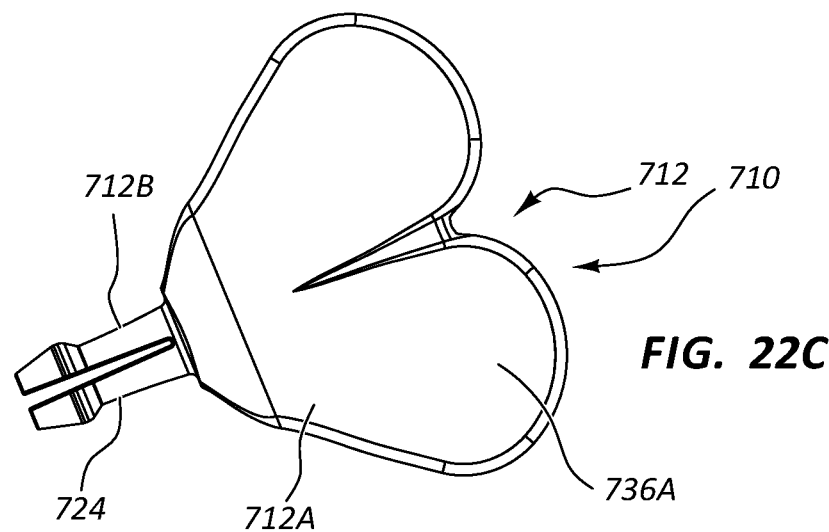

The open and shallow nature of each receiving cup 714, angled toward the skin surface of the patient enables the receiving cup to present a large, easily accessible target for the needle when introduced into the skin and directed toward the subcutaneously implanted access port 710. FIGS. 22A and 22B further show that the access port 710 defines a relatively low profile height, which enables relatively shorter needle lengths to be used for accessing the subcutaneous access port after implantation. FIG. 22C depicts details of a bottom portion of the port body 712. Note that in this and other embodiments, the receiving cups can define different surfaces, including funnel-shaped, concave-shaped, hemispherical, etc.

The port body 712 includes a plurality of palpation features 737, here implemented as ridges extending distally from the receiving cups 714, to assist a clinician to locate and/or identify the port 710 via finger palpation after implantation under the skin of the patient. Note that a variety of sizes, configurations, numbers, etc., of palpation features can be included on the port.

Figure 23:
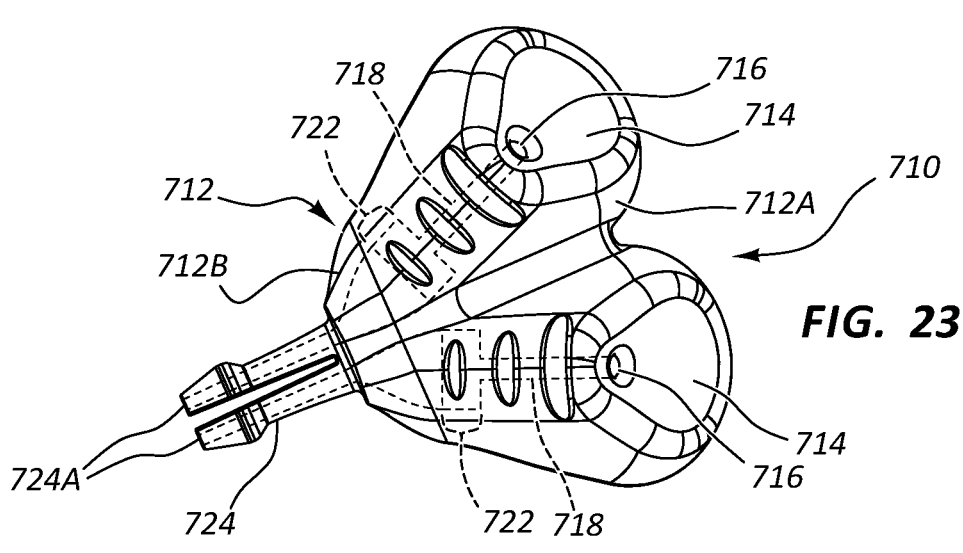
FIG. 23 is a partially transparent view of the vascular access device of FIGS. 22A-22C.
Figure 24:
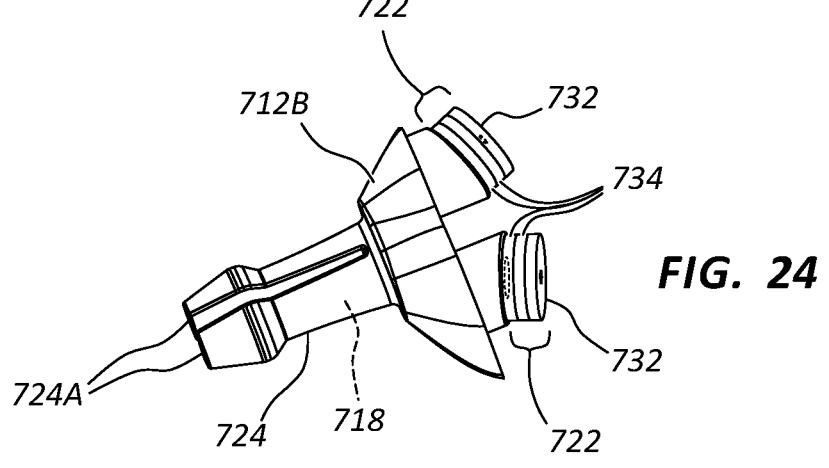
FIG. 24 is a partially transparent view of a portion of the vascular access port of FIGS. 22A-22C.

As best seen in FIGS. 23 and 24, the port body 712 further defines the two conduits 718, each conduit serving as a pathway into which a transcutaneously inserted catheter can be partially inserted so as to place the catheter in fluid communication both with the port 710 and an indwelling dual-lumen catheter operably attached to two fluid outlets 724A of a stem 724 of the port. As shown, each of the two conduits 718 of the port body first portion 712A is in fluid communication with its respective receiving cup 714 via the inlet port 716 and extends distally to a valve/seal assembly 722 disposed in a cavity cooperatively defined by the junction of the port body first portion 712A and the second portion 712B. As with other embodiments herein, each conduit 718 distally extends from the respective inlet port 716 in an angled downward direction from the perspective shown in FIG. 23 to a conduit bend before continuing to the cavity wherein is disposed the valve/seal assembly. Note that the conduit bend can desirably serve as a needle-stop feature, preventing the needle 42 from advancing along the conduit 718 past the bend. The conduits distally extend past the valve/seal assembly 722 and through the port body second portion 712B to the fluid outlets of the stem 724. In the present embodiment the conduit 718 is sized so as to enable the catheter 40 (FIG. 14A) to pass therethrough past the valve/seal assembly 722.

As mentioned, the cavities, each defined by the junction of the respective first portion 712A and the second portion 712B of the port body 712, each define a space through which the conduit 718 passes and in which is housed the valve/seal assembly 722. In the present embodiment and as best seen in FIGS. 23 and 24, each of the two valve/seal assemblies 722 includes a sealing element, or seal 732, which defines a central hole through which the catheter 40 (FIGS. 14A, 14D) can pass, and two slit valves 734, each including a single slit and positioned adjacent each other such that the slits are substantially orthogonal to one another, through which the catheter also passes. The seal 732 and the slit valves 734 are sandwiched together in one embodiment, with the seal disposed proximal to the slit valves, and secured in place within the correspondingly sized cavity as shown in FIGS. 23 and 24.

As mentioned, the slits of the slit valves 734 are orthogonally offset from one another by about 90 degrees in the present embodiment, though other relationships are possible, including the use of a single slit valve including two orthogonal slits. These and other modifications to this and the other valve/seal assembly embodiments herein are therefore contemplated.

As with previous embodiments, the seal 732 and slit valves 734 of the valve/seal assembly 722 cooperate to enable fluid-tight passage therethrough of the catheter 40 (see, e.g., FIG. 14A) while also preventing backflow of fluid through the valve/seal assembly. Indeed, in one embodiment the seals disclosed herein prevent fluid flow around the external portion of the catheter when the catheter is disposed through the seal 732, while the valve 734 is suitable for preventing fluid flow when no catheter passes through them. As such, when the catheter 40 is not inserted therethrough the valve/seal assembly 722 seals to prevent passage of air or fluid through the conduit 718. In the present embodiment, the seal 732 and valve 734 are composed of silicone, such as SILASTIC® Q7-4850 liquid silicone rubber available from Dow Corning Corporation, though other suitably compliant materials can be employed. In one embodiment, silicone oil, such as NuSil Technology Med 400 silicone oil, is included with the seal 732 and valve 734 to enhance lubricity and extend component life. In another embodiment, the silicone oil is infused into the silicone.

Though not explicitly shown here, the port 710, as with other embodiments herein, can include radiopaque indicia configured to enable the port to be radiographically identified after implantation into the patient body. In one embodiment, the indicia include the letters "IV" and "CT" to indicate suitability of the port 710 to receive peripheral IV catheters and that the port is capable of power injection of fluids therethrough. Of course, a variety of other indicia, including letters, numbers, symbols, etc., may be used.

Though single and dual-port configurations have been described herein, it is appreciated that ports including more than two receiving cups are contemplated. Note also that certain of the receiving cups described herein are described as funnel shaped, while other receiving cups are described herein as concavely shaped. It is noted that that the receiving cups can interchangeably include aspects of one or the other, or both, of these receiving cup shapes, according to a particular embodiment.

Figure 27:
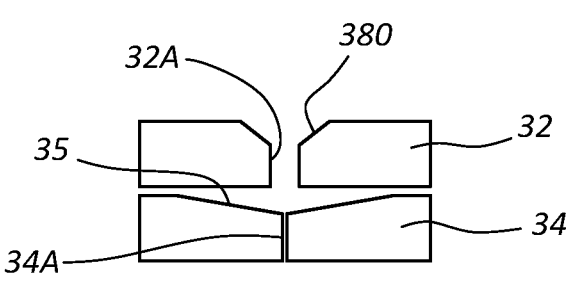
FIG. 27 is a cross-sectional view of a valve/seal configuration according to one embodiment.
Figure 28:
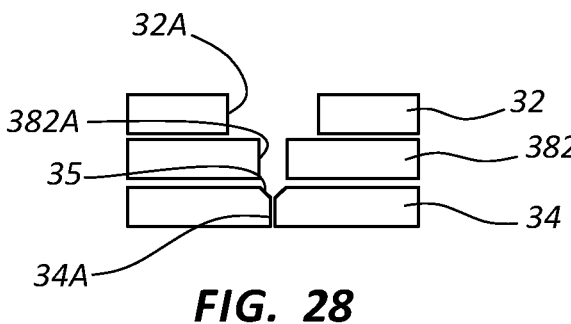
FIG. 28 is a cross-sectional view of a valve/seal configuration according to one embodiment.
Figure 29:
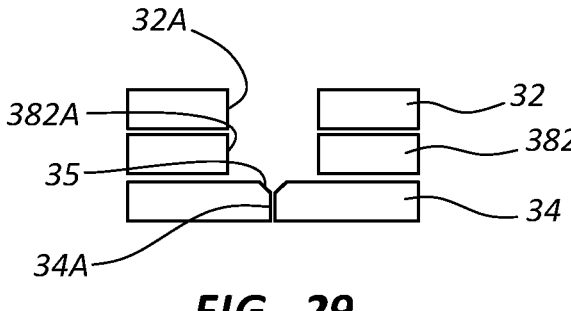
FIG. 29 is a cross-sectional view of a valve/seal configuration according to one embodiment.

FIGS. 27-30 depict details of various possible configurations for the valve/seal assembly, according to example embodiments. In FIG. 27, the seal 32 includes a central depression 380, similar but relatively steeper than the depression 35 of the valve 34. In FIG. 28, two seals are included—the seal 32 and a second seal 382 interposed between the seal 32 and the valve 34. The second seal 382 includes a central hole 382A that includes a diameter smaller relative to the hole 32A of the seal 32. FIG. 29 includes a similar configuration, but the hole 382A is similar in size to the hole 32A. A small central depression 35 is included on the valve 34 in both FIG. 28 and FIG. 29.

Figure 30:
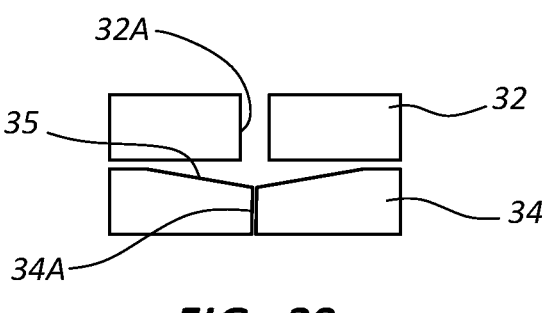
FIG. 30 is a cross-sectional view of a valve/seal configuration according to one embodiment.

In FIG. 30, the seal 32 includes a relatively small-diameter central hole 32A, and the valve 34 includes a relatively large central depression 35. Note that the valve/seal assemblies shown in FIGS. 27-30 are oriented in the figures such that the catheter pierces the seals and valves in a direction corresponding from the top of the page toward the bottom of the page.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A low-profile access port, comprising:
a first receiving body portion formed from a metal material, the first receiving body portion comprising:
a first receiving cup including a first inlet port;
a first conduit in communication with the first inlet port; and
a depression or recess forming an alphanumeric designation;
a second receiving body portion formed from a metal material, the second receiving body portion comprising:
a second receiving cup including a second inlet port; and
a second conduit in communication with the second inlet port;
an outlet body portion in fluid communication with the first receiving body portion and the second receiving body portion, the outlet body portion comprising:

a bifurcated proximal end having a first connection portion coupled to the first receiving body portion and a second connection portion coupled to the second receiving body portion; and
a stem having a first fluid outlet in fluid communication with the first connection portion and a second fluid outlet in fluid communication with the second connection portion;
a first valve assembly between the first connection portion and the first receiving body portion;
a second valve assembly between the second connection portion and the second receiving body portion; and
an overmolded portion surrounding at least the first receiving body portion and the second receiving body portion.

2. The access port according to claim 1, wherein the first valve assembly and the second valve assembly each includes a seal defining a central hole and a valve including one or more slits.

3. The access port according to claim 1, wherein the first receiving cup is configured to direct a catheter-bearing needle into the first inlet port, and wherein the second receiving cup is configured to direct the catheter bearing needle into the second inlet port.

4. The access port according to claim 1, wherein the alphanumeric designation is located in the first receiving cup.

5. The access port according to claim 1, wherein the second receiving body portion includes a depression or recess forming an alphanumeric designation.

6. The access port according to claim 5, wherein the alphanumeric designation is located in the second receiving cup.

7. The access port according to claim 1, wherein the first receiving body portion and the second receiving body portion are angularly positioned on opposite sides of a central longitudinal axis of the access port.

8. The access port according to claim 7, wherein the central longitudinal axis of the access port bisects the first fluid outlet and the second fluid outlet of the stem.

9. The access port according to claim 1, wherein the alphanumeric designation includes the letters "IV".

10. The access port according to claim 1, wherein a perimeter of the first receiving cup and a perimeter of the second receiving cup are disposed in a single imaginary plane.

11. The access port according to claim 1, wherein the first conduit and the second conduit each defines a conduit bend to prevent passage of a needle of a catheter-bearing needle while permitting passage of a catheter of the catheter-bearing needle.

12. The access port according to claim 11, wherein the first valve assembly and the second valve assembly are disposed distal to the conduit bend of the first conduit and the second conduit.

13. The access port according to claim 1, further comprising at least one palpation feature configured to enable a clinician to palpate a location of the access port following subcutaneously implantation.

* * * * *